(12) United States Patent
Butora

(10) Patent No.: US 9,884,886 B2
(45) Date of Patent: Feb. 6, 2018

(54) DISULFIDE MASKED PRODRUG COMPOSITIONS AND METHODS

(71) Applicant: Merck Sharp & Dohme Corp., Rahway, NJ (US)

(72) Inventor: Gabor Butora, Martinsville, NJ (US)

(73) Assignee: Merck Sharp & Dohme, Rahway, NJ (US)

( * ) Notice: Subject to any disclaimer, the term of this patent is extended or adjusted under 35 U.S.C. 154(b) by 150 days.

(21) Appl. No.: 14/648,716

(22) PCT Filed: Dec. 2, 2013

(86) PCT No.: PCT/US2013/072536
§ 371 (c)(1),
(2) Date: Jun. 1, 2015

(87) PCT Pub. No.: WO2014/088920
PCT Pub. Date: Jun. 12, 2014

(65) Prior Publication Data
US 2015/0315226 A1 Nov. 5, 2015

Related U.S. Application Data

(60) Provisional application No. 61/734,043, filed on Dec. 6, 2012.

(51) Int. Cl.
| | | |
|---|---|---|
| *C07H 19/20* | (2006.01) | |
| *C07H 19/10* | (2006.01) | |
| *C07H 21/04* | (2006.01) | |
| *A61K 38/14* | (2006.01) | |
| *C07H 9/00* | (2006.01) | |
| *A61K 38/00* | (2006.01) | |
| *A61K 47/00* | (2006.01) | |
| *C12N 15/11* | (2006.01) | |
| *A01N 43/04* | (2006.01) | |
| *A61K 31/70* | (2006.01) | |
| *C07K 9/00* | (2006.01) | |
| *C12N 15/113* | (2010.01) | |
| *C07D 339/08* | (2006.01) | |
| *C07F 9/6553* | (2006.01) | |

(Continued)

(52) U.S. Cl.
CPC ........... *C07H 19/10* (2013.01); *A61K 47/549* (2017.08); *C07D 339/08* (2013.01); *C07D 405/04* (2013.01); *C07D 409/14* (2013.01); *C07D 487/04* (2013.01); *C07F 9/65586* (2013.01); *C07F 9/65616* (2013.01); *C07F 9/655363* (2013.01); *C07H 19/20* (2013.01); *C07H 19/207* (2013.01); *C07H 21/00* (2013.01); *C07K 9/001* (2013.01); *C12N 15/113* (2013.01); *C12N 2310/14* (2013.01); *C12N 2310/351* (2013.01); *C12N 2320/30* (2013.01)

(58) Field of Classification Search
CPC ...... C07H 19/20; C07H 19/207; C07H 19/10; C07H 21/00; C07D 339/08; C07D 405/04; C07D 487/04; C07D 409/14; C07F 9/65586; C07F 9/65616; C07F 9/655363; A61K 47/48092; C07K 9/001; C12N 15/113; C12N 2310/14; C12N 2310/351; C12N 2320/30
See application file for complete search history.

(56) References Cited

U.S. PATENT DOCUMENTS 6,008,398 A 12/1999 Gentles et al.
7,601,848 B2 10/2009 Hartwich et al.
(Continued)

FOREIGN PATENT DOCUMENTS

WO WO9302093 2/1993
WO WO2008141289 A1 11/2008
(Continued)

OTHER PUBLICATIONS

Johnson, A Label-Free, Electrochemical SERS-Based Assay for Detection of DNA Hybridization and Discrimination of Mutations, J. of the American Chemical Society, 2012, 14099-14107, 134-34.
(Continued)

*Primary Examiner* — Lawrence E Crane
(74) *Attorney, Agent, or Firm* — Yong Zhao; John C. Todaro

(57) ABSTRACT

The present invention relates to disulfide masked prodrug compounds of formula I, compositions and methods that are amenable to bioactivation by a reducing agent such as glutathione:

W—P(V)LG (Formula I), wherein P(V)LG is a pentavalent phosphorus leaving group; and W is:

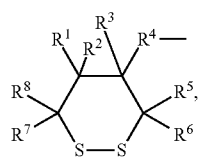

wherein $R^1$, $R^2$, $R^3$, $R^4$, $R^5$, $R^6$, $R^7$ and $R^8$ are as defined in the specification. Such disulfide based compounds, compositions, and methods can be useful, for example, in providing novel prodrugs for use as therapeutics. Once administered, the prodrug is metabolized in vivo into an active metabolite in a process termed bioactivation.

8 Claims, 13 Drawing Sheets

(51) Int. Cl.
- *C07F 9/6558* (2006.01)
- *C07F 9/6561* (2006.01)
- *C07D 405/04* (2006.01)
- *C07D 409/14* (2006.01)
- *C07D 487/04* (2006.01)
- *C07H 19/207* (2006.01)
- *C07H 21/00* (2006.01)
- *A61K 47/54* (2017.01)

(56) References Cited

U.S. PATENT DOCUMENTS

| | | | |
|---|---|---|---|
| 8,741,858 B2 * | 6/2014 | Ren | A61K 47/48215 514/42 |
| 9,365,604 B2 * | 6/2016 | Ren | A61K 47/48215 |
| 2006/0003952 A1 | 1/2006 | Ravikumar et al. | |
| 2007/0099211 A1 | 5/2007 | Aivazachvili et al. | |
| 2010/0286084 A1 | 11/2010 | Ren et al. | |

FOREIGN PATENT DOCUMENTS

| | | |
|---|---|---|
| WO | WO2010039543 | 4/2010 |
| WO | WO2014088923 | 6/2014 |

OTHER PUBLICATIONS

Liepold, Electrically detected displacement assay (EDDA): a practical approach to nucleic acid testing in clinical or medicial diagnosis, Analytical and bioanalytical chemistry, 2008, 1759-1772, 391-5.

Perigaud et al., Rational design for cytosolic delivery of nucleoside monphosphates: "SATE" and "DTE" as enzyme-labile transient phosphate protecting groups, Bioorganic Medical Chemistry Letters, 1993, 2521-2526, 3-12.

* cited by examiner

DISULFIDE MASKED PRODRUG COMPOSITIONS AND METHODS

CROSS REFERENCE TO RELATED APPLICATIONS

This application is a U.S. National Phase application under 35 U.S.C. § 371 of PCT Application No. PCT/US2013/072536 filed Dec. 2, 2013, which claims priority from U.S. Provisional Application Ser. No. 61/734,043, filed Dec. 6, 2012.

FIELD OF THE INVENTION

The present invention relates to disulfide masked prodrug compounds, compositions and methods that are amenable to bioactivation by a reducing agent such as glutathione. Such disulfide based compounds, compositions, and methods can be useful, for example, in providing novel prodrugs for use as therapeutics.

BACKGROUND OF THE INVENTION

The following is a discussion of relevant art pertaining to certain prodrug compositions. The discussion is provided only for understanding of the invention that follows. The summary is not an admission that any of the work described below is prior art to the claimed invention.

The fields of medicinal chemistry and biotechnology have yielded a multitude of biologically active compounds having well demonstrated in vitro activity. These compounds, however, need to be effectively delivered to target cells and tissues of interest in order to be useful as research tools or as therapeutic agents in vivo. Many biologically active molecules have in vivo activity profiles that are compromised by virtue of their net negative (anionic) charge, their size, or a combination of both anionic charge and size. Furthermore, the polyanionic backbone of oligonucleotide compounds is recognized by nucleases that rapidly degrade these molecules. Various strategies have been developed in an attempt to overcome these barriers. In the case of oligonucleotide delivery, both viral and non-viral delivery strategies have yielded mixed results, with most having dose limiting toxicity or other safety issues. Such safety issues are representative of the challenge faced in effectively delivering other charged molecules to cells and tissues of interest. These challenges have driven innovation in a divergent approach, that of the prodrug.

A prodrug is a pharmacological substance administered in an inactive or significantly less active form. Once administered, the prodrug is metabolised in vivo into an active metabolite in a process termed bioactivation. The rationale behind the use of a prodrug is generally for absorption, distribution, metabolism, and excretion (ADME) optimization. Anion masking produgs represent a new platform of compounds that provide the advantage of improving ADME properties through a variety of mechanisms. First, the anion masking prodrug neutralizes anionic charge, and therefore overcomes barriers of cellular adsorption and tissue distribution. Second, because certain nucleases rely upon anionic charge to identify their substrates, the anion masking prodrug can circumvent metabolism. Furthermore, the charge masking moiety of the prodrug can also serve as a scaffold for various chemical entities that can confer improved targeting, immunosuppression, or solubility profiles. All of these factors can lead to improved pharmacokinetic and pharmacodynamic properties of a compound or molecule of interest.

Examples of anion masking phosphotriester protecting groups have been disclosed, see for example Lebleu et al., (2000), Russ. J. Bioorg. Chem., 26, 174-182. However, this approach utilizes ultraviolet radiation for deprotection and thus is not amenable to use in vivo. Beaucage et al. (2007), J. Org. Chem., 72, 805-815 describes in vivo bioactivation of certain phosphotriester oligonucleotide prodrugs. However, this approach generates THF as a byproduct upon bioconversion. WO 2010/039543 describes certain anion masking disulfide phosphotriester oligonucleotide prodrugs. Nevertheless, cyclodeesterification of these disulfide prodrugs results in the release of a reactive thiirane species, which can limit the use of such prodrugs due to dose limiting toxicity.

Glutathione (GSH) is a tripeptide that contains an unusual peptide linkage between the amine group of cysteine, which is attached by normal peptide linkage, to a glycine and the carboxyl group of the glutamate side-chain. Glutathione is an important antioxidant, preventing damage to cellular components caused by reactive oxygen species such as free radicals and peroxides. Glutathione thiol groups are reducing agents, existing at a concentration of approximately 5 mM in cells. Glutathione reduces disulfide bonds formed within cytoplasmic proteins to cysteines by serving as an electron donor. In the process, glutathione is converted to its oxidized form glutathione disulfide (GSSG), which is also called L(−)-Glutathione. Once oxidized, glutathione can be reduced back by glutathione reductase, using NADPH as an electron donor. Glutathione is therefore an attractive bioconversion reducing agent for prodrugs.

Certain examples of glutathione activated prodrugs are disclosed in, for example, Gunnarsdottir et al., (2003), Drug Metabolism and Disposition, 32, 321-327 and Tirouvanziam et al., (2006), PNAS, 103, 12, 4628-4633. These glutathione activiated prodrugs, however, do not offer any anionic charge masking capabilities. Accordingly, there exists a need for improved anion masking prodrugs that are amenable to bioconversion in vivo.

SUMMARY OF THE INVENTION

The invention provides a solution to the problem of providing glutathione activated prodrug compositions and methods that are capable of masking anionic charge and that do not result in the formation of a reactive species upon bioconversion.

Disclosed herein are prodrug compounds and compositions and methods of making and using the same. The prodrug compounds, compositions and methods of the invention feature a conformationally restricted disulfide phosphotriester moiety to mask anionic charge. The conformationally restricted disulfide phosphotriester moiety can also serve as a scaffold to attach a helper molecule, such as targeting moieties, immunnosuppression moieties, solubility enhancing moieties etc. The conformationally restricted disulfide phosphotriester moiety undergoes charge dissipation driven cyclodeesterification via glutathione mediated reduction/bioconversion to release the active anionic molecule of interest and eject any helper moiety during the bioconversion process. During bioconversion, the reactive thiirane species is internally quenched via a intramolecular 1,5-exo-tet ring closure to produce stable tetrahydrothiophenes. The disulfide phosphotriester moiety of the invention can provide charge masked prodrug analogs of nucleic acids, polynucleotides, oligonucleotides, peptides, polypeptides, proteins, antibodies, hormones, small molecules, antivirals and other biologically active molecules as are known in the art.

DETAILED DESCRIPTION OF THE INVENTION

A. Terms and Definitions

Figure 1:
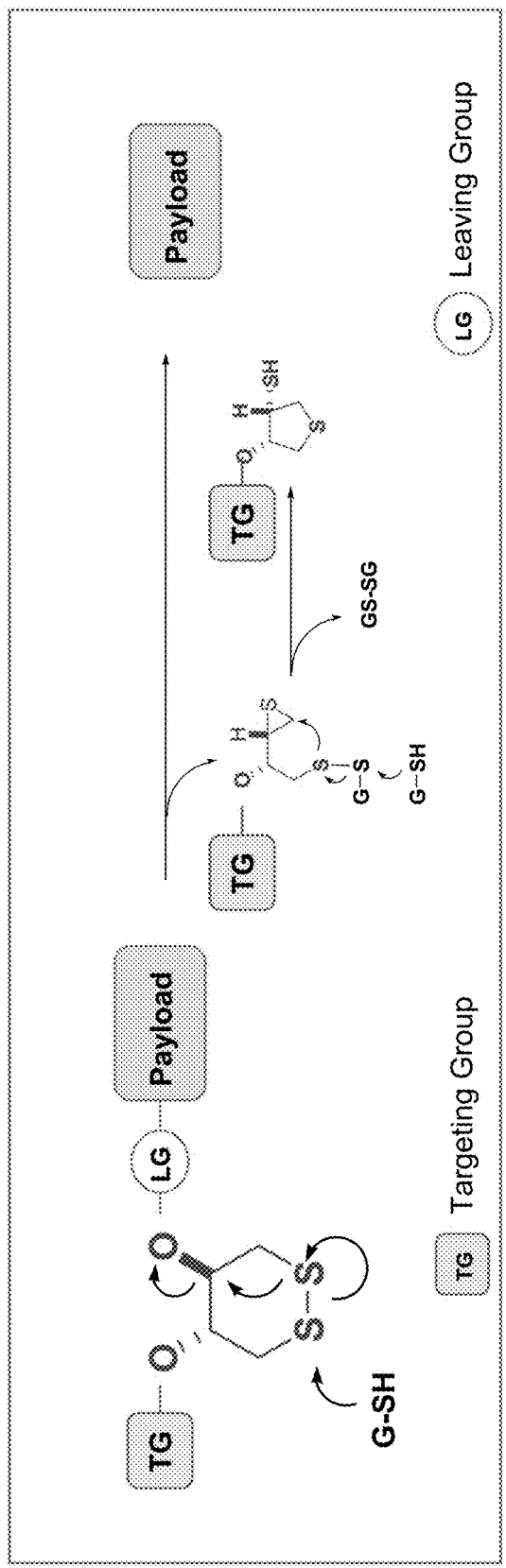
FIG. 1 shows a non-limiting example of a proposed mechanism comprising non-enzymatic, chemically driven release for disulfide masked prodrugs of the invention. While not wishing to be bound by theory, this mechanism comprises (1) pH-dependent disulfide reduction followed by (2) charge-dissipation driven cyclodeesterification followed by (3) intramolecular thiirane rearrangement. The Targeting Group (TG) can be any targeting group or moiety (e.g., a ligand, peptide, antibody, etc.) as is generally known in the art and is optionally present. The leaving group is preferably a pentavalent phosphorus leaving group as is generally known in the art, but can include other suitable leaving groups as are readily appreciated by one of skill in the art (e.g., triflates, flurosulphonates, tosylates, mesylates, carbonylates, nitrates, phosphates, etc.). The payload is a compound that is preferably to be administered to a subject, such as any therapeutic or prophylactic compound as is generally known in the art including nucleic acids, nucleotides, nucleosides, polynucleotides, oligonucleotides, peptides, polypeptides, proteins, antibodies, hormones, small molecules, antivirals and other biologically active molecules.

The following terminology and definitions apply as used in the present application.

As used in this specification and the appended claims, the singular forms "a," "an," and "the" include plural referents unless the content clearly dictates otherwise. Thus, for example, reference to "a cell" includes a combination of two or more cells, and the like.

Any concentration range, percentage range, ratio range or integer range is to be understood to include the value of any integer within the recited range, and when appropriate, fractions thereof (such as on tenth and one hundredth of an integer), unless otherwise indicated.

"About" or "approximately," as used herein, in reference to a number are generally taken to include numbers that fall within a range of 5% in either direction (greater than or less than) of the number unless otherwise stated or otherwise evident from the context (except where such number would exceed 100% of a possible value). Where ranges are stated, the endpoints are included within the range unless otherwise stated or otherwise evident from the context.

The term "alkyl" as used herein refers to its meaning as is generally accepted in the art. The term generally refers to a saturated or unsaturated hydrocarbon, including straight-chain, branched-chain, alkenyl, alkynyl groups and cyclic groups, but excludes aromatic groups. Notwithstanding the foregoing, alkyl also refers to non-aromatic heterocyclic groups. Preferably, the alkyl group has 1 to 12 carbons. More preferably, it is a lower alkyl of from 1 to 4 carbons, more preferably 1 to 4 carbons. The alkyl group can be substituted or unsubstituted. When substituted, the substituted group(s) is preferably, hydroxyl, halogen, cyano, C1-C4 alkoxy, =O, =S, $NO_2$, SH, $NH_2$, or $NR_1R_2$, where $R_1$ and $R_2$ independently are H or C1-C4 alkyl.

The term "aryl" as used herein refers to its meaning as is generally accepted in the art. The term generally refers to an aromatic group that has at least one ring having a conjugated pi electron system and includes carbocyclic aryl, heterocyclic aryl and biaryl groups, all of which can be optionally substituted. The preferred substituent(s) of aryl groups are halogen, trihalomethyl, hydroxyl, SH, OH, cyano, C1-C4 alkoxy, C1-C4 alkyl, C2-C4 alkenyl, C2-C4 alkynyl, $NH_2$, and $NR_1R_2$ groups, where $R_1$ and $R_2$ independently are H or C1-C4 alkyl.

The term "alkylaryl" as used herein refers to its meaning as is generally accepted in the art. The term generally refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and examples of heterocyclic aryl groups having such heteroatoms include furanyl, thienyl, pyridyl, pyrrolyl, N-lower alkyl pyrrolo, pyrimidyl, pyrazinyl, imidazolyl and the like, all optionally substituted. Preferably, the alkyl group is a C1-C4 alkyl group.

The term "amide" as used herein refers to its meaning as is generally accepted in the art. The term generally refers to an —C(O)—NH—R, where R is either alkyl, aryl, alkylaryl or hydrogen.

The phrase "biological system" as used herein refers to its meaning as is generally accepted in the art. The term generally refers to material, in a purified or unpurified form, from biological sources including, but not limited to, human or animal, wherein the system comprises the components required for RNAi activity. Thus, the phrase includes, for example, a cell, tissue, subject, or organism, or extract thereof. The term also includes reconstituted material from a biological source.

The term "cell" as used herein refers to its meaning as is generally accepted in the art. With reference to exemplary nucleic acid molecules of the invention, the term is used in its usual biological sense, and does not refer to an entire multicellular organism, e.g., specifically does not refer to a human being. The cell can be present in an organism, e.g., birds, plants and mammals, such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell.

The terms "composition" or "formulation" as used herein refer to their generally accepted meaning in the art. These terms generally refer to a composition or formulation, such as in a pharmaceutically acceptable carrier or diluent, in a form suitable for administration, e.g., systemic or local administration, into a cell or subject, including, for example, a human. Suitable forms, in part, depend upon the use or the route of entry, for example oral, transdermal, inhalation, or by injection. Such forms should not prevent the composition or formulation from reaching a target cell. For example, compositions injected into the blood stream should be soluble. Other factors are known in the art, and include considerations such as toxicity and forms that prevent the composition or formulation from exerting its effect. As used herein, pharmaceutical formulations include formulations for human and veterinary use.

The term "folate moiety" as used herein refers to its meaning as is generally accepted in the art. The term generally refers to a moiety comprising the following chemical group:

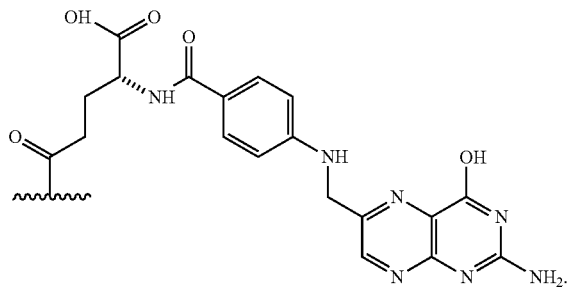 [SMILES: *C(=O)CC[C@@H](NC(=O)c1ccc(NCc2cnc3nc(N)nc(O)c3n2)cc1)C(=O)O]

The term "including" (and any form thereof, such as "includes" and "include"), "comprising" (and any form thereof, such as "has" or "have") or "containing" (and any form thereof such as "contains" or "contain") are inclusive and open-ended and do not exclude additional, unrecited elements or method steps.

The term "ligand" or refers to such compounds and compositions as are generally known in the art. Non-limiting examples of such ligands are described herein including in the documents specifically incorporated by reference herein. Non-limiting, examples of such ligands are described in U.S. Publication Nos. US2008/0152661 A1 and US 2004/0162260 A1 (e.g., CDM-LBA, CDM-Pip-LBA, CDM-PEG, CDM-NAG, etc.) and U.S. patent application Ser. Nos. 10/427,160 10/201,394, 61/322,422, 61/378,609, and 61/315,223; and U.S. Pat. Nos. 6,528,631; 6,335,434; 6,235,886; 6,153,737; 5,214,136; and 5,138,045. See also Manoharan, ANTISENSE & NUCLEIC ACID DRUG DEVELOPMENT 12:103-128 (2002). A prodrug molecule of the invention can be formulated or administered with any covalently linked ligand as described herein or otherwise known in the art.

The term "linker" as used herein refers to its meaning as is generally known in the art. Non-limiting examples of linkers are described herein, for example in Table 1 and including in the documents specifically incorporated by reference herein.

The terms "mammalian" or "mammal" as used herein refers to its meaning as is generally accepted in the art. The term generally refers to any warm blooded vertebrate species, such as a human, mouse, rat, dog, cat, hamster, guinea pig, rabbit, livestock, and the like.

The term "N-Acetyl Galactosamine moiety" as used herein refers to its meaning as is generally accepted in the art. The term generally refers to a moiety comprising the following chemical group:

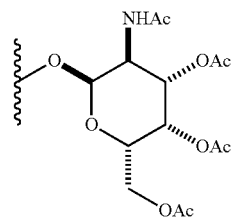 [SMILES: *O[C@@H]1O[C@@H](COC(C)=O)[C@@H](OC(C)=O)[C@@H](OC(C)=O)[C@@H]1NC(C)=O]

The term "peptide moiety" as used herein refers to its meaning as is generally accepted in the art. The term generally refers to a moiety having one or more peptide functionalities.

The term "polymer" refers to polymeric compounds, compositions and formulations as are generally known in the art. Non-limiting examples of such polymers, including polymeric delivery systems are described herein including in the documents specifically incorporated by reference herein. A molecule or compound of the invention can be formulated or administered with any polymer as described herein or otherwise known in the art.

The term "steroid moiety" as used herein refers to its meaning as is generally accepted in the art. The term generally refers to a moiety having one or more steroid functionalities, such as cholesterol.

The term "subject" as used herein refers to its meaning as is generally accepted in the art. The term generally refers an organism to which the nucleic acid molecules of the invention can be administered. A subject can be a mammal or mammalian cells, including a human or human cells. The term also refers to an organism, which is a donor or recipient of explanted cells or the cells themselves.

The phrase "systemic administration" as used herein refers to its meaning as is generally accepted in the art. The phrase generally refers in vivo systemic absorption or accumulation of drugs in the blood stream followed by distribution throughout the entire body.

The term "targeting agent" as used herein refers to its meaning as is generally accepted in the art. The term generally refers to a moiety that confers some degree of target specificity to one or more cells, tissues, or organs, such as in a subject or organism and thus the ability to target such cells, tissues, or organs with a compound or composition of interest.

The phrase "therapeutically effective amount" as used herein refers to its meaning as is generally accepted in the art. The term generally refers to the amount of the compound or composition that will elicit the biological or medical response of a cell, tissue, system, animal or human that is be sought by the researcher, veterinarian, medical doctor or other clinician. For example, if a given clinical treatment is considered effective when there is at least a 25% reduction in a measurable parameter associated with a disease or disorder, a therapeutically effective amount of a drug for the treatment of that disease or disorder is that amount necessary to effect at least a 25% reduction in that parameter.

The term "vitamin moiety" as used herein refers to its meaning as is generally accepted in the art. The term generally refers to a moiety having one or more vitamin functionalities, such as folic acid, vitamin C, vitamin E, vitamin D, vitamin B5, vitamin B12 and the like.

B. Compounds

Provided herein are compounds having Formula I:

W—P(V)LG   (Formula I), wherein,
P(V)LG is a pentavalent phosphorus leaving group;
W is:

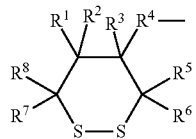

$R^1$ is H, OH, $C_{1-6}$ alkyl, $C_{1-6}$ alkyl substituted with one or more hydroxyl groups, $C_{1-6}$ alkyl substituted with one or more halo groups, $C_{1-6}$ alkenyl, $C_{1-6}$ alkenyl substituted with one or more hydroxyl groups, $C_{1-6}$ alkenyl substituted with one or more halo groups, $C_{1-6}$ alkynyl, $C_{1-6}$ alkynyl substituted with one or more hydroxyl groups, $C_{1-6}$ alkynyl substituted with one or more halo groups, $C_{1-6}$ alkoxyl, $C_{1-6}$ alkoxyl substituted with one or more hydroxyl groups, $C_{1-6}$ alkoxyl substituted with one or more halo groups, aryl, heteroaryl, heterocyclyl, —NH$C_{1-6}$ alkyl, aryl$C_{1-6}$ alkyl, heteroaryl$C_{1-6}$ alkyl, heterocyclyl$C_{1-6}$ alkyl, guanidinyl, $C_{1-6}$alkylC(O)O—, arylC(O)O—, heterocyclylC(O)O—, O-propargyl, S-propargyl, O-allyl, S-allyl, or X-L-Y; wherein X is O, S, NH, C(O), S(O), $C_{1-6}$ alkyl, $C_{1-6}$ alkyl substituted with one or more hydroxyl groups, $C_{1-6}$ alkyl substituted with one or more halo groups, $C_{1-6}$ alkenyl, $C_{1-6}$ alkenyl substituted with one or more hydroxyl groups, $C_{1-6}$ alkenyl substituted with one or more halo groups, $C_{1-6}$ alkynyl, $C_{1-6}$ alkynyl substituted with one or more hydroxyl groups, $C_{1-6}$ alkynyl substituted with one or more halo groups, $C_{1-6}$ alkoxyl, $C_{1-6}$ alkoxyl substituted with one or more hydroxyl groups, $C_{1-6}$ alkoxyl substituted with one or more halo groups, aryl, heteroaryl, heterocyclyl, —NH$C_{1-6}$ alkyl, aryl$C_{1-6}$ alkyl, heteroaryl$C_{1-6}$ alkyl, heterocyclyl$C_{1-6}$ alkyl, guanidinyl, $C_{1-6}$alkylC(O)O—, arylC(O)O—, heterocyclylC(O)O—, O-propargyl, S-propargyl, O-allyl, S-allyl; L is a linker that is optionally present; and Y is a targeting agent, ligand and/or polymer that is optionally present;

$R^4$ is S or O and is covalently linked to P(V)LG; and each $R^2$, $R^3$, $R^5$, $R^6$, $R^7$ and $R^8$ is independently halo or $R^1$ as above.

In some embodiments, with respect to a compound having Formula I, P(V)LG comprises a nucleic acid such as a nucleotide, polynucleotide, or oligonucleotide.

In some embodiments, with respect to a compound having Formula I, W is racemic with respect to $R^1$ and $R^4$.

In some embodiments, with respect to a compound having Formula I, $R^1$ and $R^4$ of W are in trans as shown in Formula Wt:

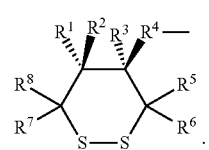

(Formula Wt)

In some embodiments, with respect to a compound having Formula I, $R^1$ and $R^4$ of W are in cis as shown in Formula Wc:

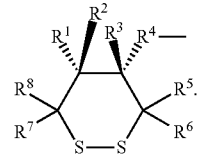

(Formula Wc)

In some embodiments, a compound having Formula I is:

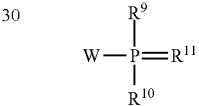

wherein,
each $R^9$ and $R^{10}$ are independently OH, SH, C(O)H, S(O)H, $C_{1-6}$ alkyl, $C_{1-6}$ alkyl substituted with one or more hydroxyl groups, $C_{1-6}$ alkyl substituted with one or more halo groups, OBn, NHBn, or Z-Q, wherein each Z is independently O, S, N, NH, $C_{1-6}$ alkyl, $C_{1-6}$ alkyl substituted with one or more halo groups, and each Q is independently aryl, any nucleotide, non-nucleotide, or polynucleotide which can be naturally-occurring or chemically-modified; and
$R^{11}$ is S or O.

In some embodiments, a compound having Formula I is:

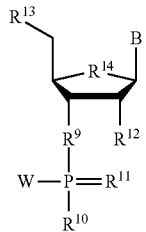

wherein,
$R^9$ is O, S, C(O), S(O), $C_{1-6}$ alkyl, $C_{1-6}$ alkyl substituted with one or more hydroxyl groups, $C_{1-6}$ alkyl substituted with one or more halo groups;
$R^{10}$ is OH, SH, C(O)H, S(O)H, $C_{1-6}$ alkyl, $C_{1-6}$ alkyl substituted with one or more hydroxyl groups, $C_{1-6}$ alkyl substituted with one or more halo groups, OBn, NHBn, or Z-Q, wherein Z is O, S, N, NH, $C_{1-6}$ alkyl, $C_{1-6}$ alkyl substituted with one or more halo groups, and Q is aryl, any nucleotide, non-nucleotide, or polynucleotide which can be naturally-occurring or chemically-modified;

$R^{11}$ is S or O;

$R^{12}$ is H, halo, $C_{1-6}$alkoxyl, $C_{1-6}$ alkenyl, $C_{1-6}$ alkenyl substituted with one or more hydroxyl groups, $C_{1-6}$ alkenyl substituted with one or more halo groups, or —$OR^{15}$;

$R^{13}$ is H, —OH—O-trityl, substituted —O-trityl, —O-pixyl (9-phenylxanthenyl), substituted-O-pixyl (9-phenylxanthenyl), S-pixyl (9-phenylxanthenyl), substituted S-pixyl (9-phenylxanthenyl), halo, $C_{1-6}$alkoxyl, $C_{1-6}$ alkenyl, $C_{1-6}$ alkenyl substituted with one or more hydroxyl groups, $C_{1-6}$ alkenyl substituted with one or more halo groups, a phosphate group, a phosphodiester, or —$OR^{15}$;

$R^{14}$ is O, S, $CH_2$, S=O, CHF, or $CF_2$;

$R^{15}$ is H, triisopropylsilyl$OCH_2$—, tert-butyldimethylsilyl$OCH_2$—, triethylsilyl$OCH_2$—, trimethylsilylethyl$OCH_2$—, triisopropylsilyl-, tert-butyldimethylsilyl-, trimethylsilylethyl-, triethylsilyl-, optionally substituted trimethylsilyl-, and optionally substituted trimethylsilyl$OCH_2$—; and B is H, a pyrimidine base, a purine base, a heterocyclic base, adenine, guanine, uracil, cytosine, thymine, inosine, xanthine, hypoxanthine, isocytosine, isoguanine, 2-aminoadenosine, 5-methylcytosine, 2,6-diaminopurine, phenyl, naphthyl, 3-nitropyrrole, 5-nitroindole, nebularine, pyridone, pyridinone, diflurotolyl, or any other naturally occurring or non-naturally occurring base with or without suitable protecting groups.

In some embodiments, a compound having Formula I is:

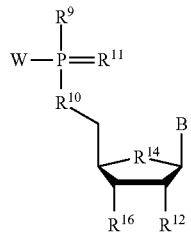

wherein, $R^9$ is OH, SH, C(O)H, S(O)H, $C_{1-6}$ alkyl, $C_{1-6}$ alkyl substituted with one or more hydroxyl groups, $C_{1-6}$ alkyl substituted with one or more halo groups, OBn, NHBn, or Z-Q, wherein Z is O, S, N, NH, $C_{1-6}$ alkyl, $C_{1-6}$ alkyl substituted with one or more halo groups, and Q is aryl, any nucleotide, non-nucleotide, or polynucleotide which can be naturally-occurring or chemically-modified;

$R^{10}$ is O, S, C(O), S(O), $C_{1-6}$ alkyl, $C_{1-6}$ alkyl substituted with one or more hydroxyl groups, $C_{1-6}$ alkyl substituted with one or more halo groups; $R^{11}$ is S or O;

$R^{12}$ is H, halo, $C_{1-6}$alkoxyl, $C_{1-6}$ alkenyl, $C_{1-6}$ alkenyl substituted with one or more hydroxyl groups, $C_{1-6}$ alkenyl substituted with one or more halo groups, or —$OR^{15}$;

$R^{14}$ is O, S, $CH_2$, S=O, CHF, or $CF_2$;

$R^{15}$ is H, triisopropylsilyl$OCH_2$—, tert-butyldimethylsilyl$OCH_2$—, triethylsilyl$OCH_2$—, trimethylsilylethyl$OCH_2$—, triisopropylsilyl-, tert-butyldimethylsilyl-, trimethylsilylethyl-, triethylsilyl-, optionally substituted trimethylsilyl-, and optionally substituted trimethylsilyl$OCH_2$—;

$R^{16}$ is H, OH or azide; and

B is H, a pyrimidine base, a purine base, a heterocyclic base, adenine, guanine, uracil, cytosine, thymine, inosine, xanthine, hypoxanthine, isocytosine, isoguanine, 2-aminoadenosine, 5-methylcytosine, 2,6-diaminopurine, phenyl, naphthyl, 3-nitropyrrole, 5-nitroindole, nebularine, pyridone, pyridinone, diflurotolyl, or any other naturally occurring or non-naturally occurring base with or without suitable protecting groups.

In some embodiments, a compound having Formula I is:

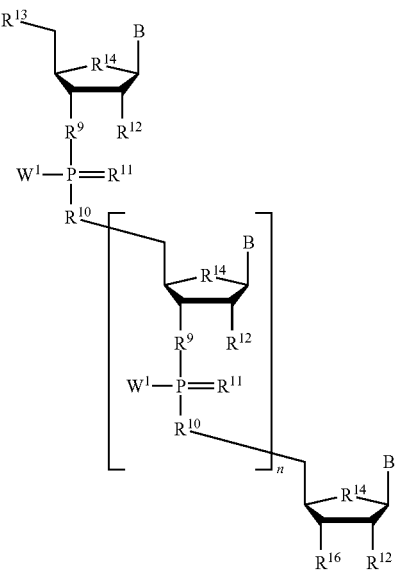

wherein, n is an integer from 0 to about 10,000;

each $W^1$ is independently OH, SH, $C_{1-6}$ alkyl, cyanoethyl, or W according to Formula I, with at least one $W^1$ being W of Formula I;

each $R^9$ and $R^{10}$ is independently O, S, C(O), S(O), $C_{1-6}$ alkyl, $C_{1-6}$ alkyl substituted with one or more hydroxyl groups, $C_{1-6}$ alkyl substituted with one or more halo groups;

each $R^{11}$ is independently S or O;

each $R^{12}$ is independently H, halo, $C_{1-6}$alkoxyl, $C_{1-6}$ alkenyl, $C_{1-6}$ alkenyl substituted with one or more hydroxyl groups, $C_{1-6}$ alkenyl substituted with one or more halo groups, or —$OR^{15}$;

$R^{13}$ is H, —OH, —O-trityl, substituted —O-trityl, —O-pixyl (9-phenylxanthenyl), substituted-O-pixyl (9-phenylxanthenyl), S-pixyl (9-phenylxanthenyl), substituted S-pixyl (9-phenylxanthenyl), halo, $C_{1-6}$alkoxyl, $C_{1-6}$ alkenyl, $C_{1-6}$ alkenyl substituted with one or more hydroxyl groups, $C_{1-6}$ alkenyl substituted with one or more halo groups, a phosphate group, a phosphodiester, or —$OR^{15}$;

each $R^{14}$ is independently O, S, $CH_2$, S=O, CHF, or $CF_2$;

each $R^{15}$ is independently H, triisopropylsilyl$OCH_2$—, tert-butyldimethylsilyl$OCH_2$—, triethylsilyl$OCH_2$—, trimethylsilylethyl$OCH_2$—, triisopropylsilyl-, tert-butyldimethylsilyl-, trimethylsilylethyl-, triethylsilyl-, optionally substituted trimethylsilyl-, or optionally substituted trimethylsilyl$OCH_2$—;

$R^{16}$ is H, OH or a capping moiety; wherein the capping moiety is selected from one or more abasic nucleotides, one or more inverted nucleotides, one or more PNAs, one or more LNAs, X-L-Y and O-Y-T where L is a linker and T is a solid support; and each B is independently H, a pyrimidine base, a purine base, a heterocyclic base, adenine, guanine, uracil, cytosine, thymine, inosine, xanthine, hypoxanthine, isocytosine, isoguanine, 2-aminoadenosine, 5-methylcytosine, 2,6-diaminopurine, phenyl, naphthyl, 3-nitropyrrole, 5-nitroindole, nebularine, pyridone, pyridinone, diflurotolyl, or any other naturally occurring or non-naturally occurring base with or without suitable protecting groups.

In some embodiments, a compound having Formula I is:

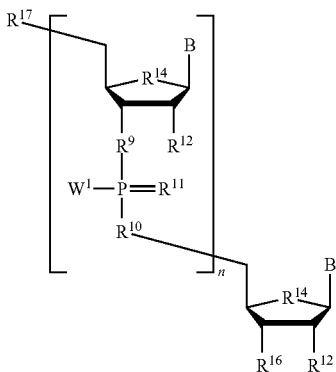

wherein, n is an integer from 1 to about 10,000;

each $W^1$ is independently OH, SH, $C_{1-6}$ alkyl, cyanoethyl, or W according to Formula I, with at least one $W^1$ being W of Formula I;

each $R^9$ and $R^{10}$ is independently O, S, C(O), S(O), $C_{1-6}$ alkyl, $C_{1-6}$ alkyl substituted with one or more hydroxyl groups, $C_{1-6}$ alkyl substituted with one or more halo groups;

each $R^{11}$ is independently S or O;

each $R^{12}$ is independently H, halo, $C_{1-6}$alkoxyl, $C_{1-6}$ alkenyl, $C_{1-6}$ alkenyl substituted with one or more hydroxyl groups, $C_{1-6}$ alkenyl substituted with one or more halo groups, or —$OR^{15}$;

each $R^{14}$ is independently O, S, $CH_2$, S=O, CHF, or $CF_2$;

each $R^{15}$ is independently H, triisopropylsilyl$OCH_2$—, tert-butyldimethylsilyl$OCH_2$—, triethylsilyl$OCH_2$—, trimethylsilylethyl$OCH_2$—, triisopropylsilyl-, tert-butyldimethylsilyl-, trimethylsilylethyl-, triethylsilyl-, optionally substituted trimethylsilyl-, and optionally substituted trimethylsilyl$OCH_2$—;

$R^{16}$ is H, OH, or a capping moiety; wherein the capping moiety is selected from one or more abasic nucleotides, one or more inverted nucleotides, one or more PNAs, one or more LNAs, X-L-Y and O-Y-T where L is a linker and T is a solid support;

$R^{17}$ is H, OH, $C_{1-6}$ alkyl, $C_{1-6}$ alkyl substituted with one or more hydroxyl groups, $C_{1-6}$ alkyl substituted with one or more halo groups, $C_{1-6}$ alkenyl, $C_{1-6}$ alkenyl substituted with one or more hydroxyl groups, $C_{1-6}$ alkenyl substituted with one or more halo groups, $C_{1-6}$ alkynyl, $C_{1-6}$ alkynyl substituted with one or more hydroxyl groups, $C_{1-6}$ alkynyl substituted with one or more halo groups, $C_{1-6}$ alkoxyl, $C_{1-6}$ alkoxyl substituted with one or more hydroxyl groups, $C_{1-6}$ alkoxyl substituted with one or more halo groups, aryl, heteroaryl, heterocyclyl, —$NHC_{1-6}$ alkyl, aryl$C_{1-6}$ alkyl, heteroaryl$C_{1-6}$ alkyl, heterocyclyl$C_{1-6}$ alkyl, guanidinyl, $C_{1-6}$alkylC(O)O—, arylC(O)O—, heterocyclylC(O)O—, O-propargyl, S-propargyl, O-allyl, S-allyl, a capping moiety such as one or more abasic nucleotide(s), inverted nucleotide(s), PNA(s), or LNA(s), or X-L-Y;

wherein X is O, S, NH, C(O), S(O), $C_{1-6}$ alkyl, $C_{1-6}$ alkyl substituted with one or more hydroxyl groups, $C_{1-6}$ alkyl substituted with one or more halo groups, $C_{1-6}$ alkenyl, $C_{1-6}$ alkenyl substituted with one or more hydroxyl groups, $C_{1-6}$ alkenyl substituted with one or more halo groups, $C_{1-6}$ alkynyl, $C_{1-6}$ alkynyl substituted with one or more hydroxyl groups, $C_{1-6}$ alkynyl substituted with one or more halo groups, $C_{1-6}$ alkoxyl, $C_{1-6}$ alkoxyl substituted with one or more hydroxyl groups, $C_{1-6}$ alkoxyl substituted with one or more halo groups, aryl, heteroaryl, heterocyclyl, —$NHC_{1-6}$ alkyl, aryl$C_{1-6}$ alkyl, heteroaryl$C_{1-6}$ alkyl, heterocyclyl$C_{1-6}$ alkyl, guanidinyl, $C_{1-6}$alkylC(O)O—, arylC(O)O—, heterocyclylC(O)O—, O-propargyl, S-propargyl, O-allyl, S-allyl; L is a linker that is optionally present; and Y is a targeting agent, ligand and/or polymer that is optionally present; and each B is independently H, a pyrimidine base, a purine base, a heterocyclic base, adenine, guanine, uracil, cytosine, thymine, inosine, xanthine, hypoxanthine, isocytosine, isoguanine, 2-aminoadenosine, 5-methylcytosine, 2,6-diaminopurine, phenyl, naphthyl, 3-nitropyrrole, 5-nitroindole, nebularine, pyridone, pyridinone, diflurotolyl, or any other naturally occurring or non-naturally occurring base with or without suitable protecting groups.

In some embodiments, a compound having Formula I is:

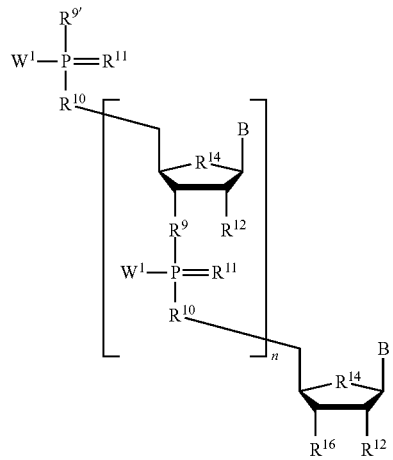

wherein, n is an integer from 1 to about 10,000;

each $W^1$ is independently OH, SH, $C_{1-6}$ alkyl, cyanoethyl, or W according to Formula I, with at least one $W^1$ being W of Formula I;

each $R^9$ and $R^{10}$ is independently O, S, C(O), S(O), $C_{1-6}$ alkyl, $C_{1-6}$ alkyl substituted with one or more hydroxyl groups, $C_{1-6}$ alkyl substituted with one or more halo groups;

$R^{9'}$ is OH, SH, $C_{1-6}$ alkyl, $C_{1-6}$ alkyl substituted with one or more hydroxyl groups, $C_{1-6}$ alkyl substituted with one or more halo groups;

each $R^{11}$ is independently S or O;

each $R^{12}$ is independently H, halo, $C_{1-6}$alkoxyl, $C_{1-6}$ alkenyl, $C_{1-6}$ alkenyl substituted with one or more hydroxyl groups, $C_{1-6}$ alkenyl substituted with one or more halo groups, or —$OR^{15}$;

each $R^{14}$ is independently O, S, $CH_2$, S=O, CHF, or $CF_2$;

each $R^{15}$ is independently H, triisopropylsilyl$OCH_2$—, tert-butyldimethylsilyl$OCH_2$—, triethylsilyl$OCH_2$—, trimethylsilylethyl$OCH_2$—, triisopropylsilyl-, tert-butyldimethylsilyl-, trimethylsilylethyl-, triethylsilyl-, optionally substituted trimethylsilyl-, and optionally substituted trimethylsilyl$OCH_2$—;

$R^{16}$ is H, OH, or a capping moiety; wherein the capping moiety is selected from one or more abasic nucleotides, one or more inverted nucleotides, one or more PNAs, one or more LNAs, X-L-Y and O-Y-T;

wherein X is O, S, NH, C(O), S(O), $C_{1-6}$ alkyl, $C_{1-6}$ alkyl substituted with one or more hydroxyl groups, $C_{1-6}$ alkyl substituted with one or more halo groups, $C_{1-6}$ alkenyl, $C_{1-6}$ alkenyl substituted with one or more hydroxyl groups, $C_{1-6}$ alkenyl substituted with one or more halo groups, $C_{1-6}$ alkynyl, $C_{1-6}$ alkynyl substituted with one or more hydroxyl groups, $C_{1-6}$ alkynyl substituted with one or more halo groups, $C_{1-6}$ alkoxyl, $C_{1-6}$ alkoxyl substituted with one or more hydroxyl groups, $C_{1-6}$ alkoxyl substituted with one or more halo groups, aryl, heteroaryl, heterocyclyl, —$NHC_{1-6}$ alkyl, aryl$C_{1-6}$ alkyl, heteroaryl$C_{1-6}$ alkyl, heterocyclyl$C_{1-6}$ alkyl, guanidinyl, $C_{1-6}$alkylC(O)O—, arylC(O)O—, heterocyclylC(O)O—, O-propargyl, S-propargyl, O-allyl, S-allyl; L is a linker that is optionally present; and Y is a targeting agent, ligand and/or polymer that is optionally present; T is a solid support; and each B is independently H, a pyrimidine base, a purine base, a heterocyclic base, adenine, guanine, uracil, cytosine, thymine, inosine, xanthine, hypoxanthine, isocytosine, isoguanine, 2-aminoadenosine, 5-methylcytosine, 2,6-diaminopurine, phenyl, naphthyl, 3-nitropyrrole, 5-nitroindole, nebularine, pyridone, pyridinone, diflurotolyl, or any other naturally occurring or non-naturally occurring base with or without suitable protecting groups.

In some embodiments, a compound having Formula I is:

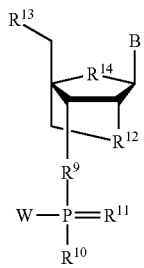

wherein, $R^9$ is O, S, C(O), S(O), $C_{1-6}$ alkyl, $C_{1-6}$ alkyl substituted with one or more hydroxyl groups, $C_{1-6}$ alkyl substituted with one or more halo groups;

$R^{10}$ is OH, SH, C(O), S(O), $C_{1-6}$ alkyl, $C_{1-6}$ alkyl substituted with one or more hydroxyl groups, $C_{1-6}$ alkyl substituted with one or more halo groups, or Z-Q, wherein each Z is independently O, S, $C_{1-6}$ alkyl, $C_{1-6}$ alkyl substituted with one or more halo groups, and each Q is independently any nucleotide, non-nucleotide, or polynucleotide which can be naturally-occurring or chemically-modified;

$R^{11}$ is S or O;

$R^{12}$ is O, S, $C_{1-6}$alkyl, $CH_2$, substituted $C_{1-6}$alkyl, NH or substituted N;

$R^{13}$ is H, —OH—O-trityl, substituted —O-trityl, —O-pixyl (9-phenylxanthenyl), substituted-O-pixyl (9-phenylxanthenyl), S-pixyl (9-phenylxanthenyl), substituted S-pixyl (9-phenylxanthenyl), halo, $C_{1-6}$alkoxyl, $C_{1-6}$ alkenyl, $C_{1-6}$ alkenyl substituted with one or more hydroxyl groups, $C_{1-6}$ alkenyl substituted with one or more halo groups, a phosphate group, a phosphodiester, or —$OR^{15}$;

$R^{14}$ is O, S, $CH_2$, S=O, CHF, or $CF_2$;

$R^{15}$ is H, triisopropylsilylOCH$_2$—, tert-butyldimethylsilylOCH$_2$—, triethylsilylOCH$_2$—, trimethylsilylethylOCH$_2$—, triisopropylsilyl-, tert-butyldimethylsilyl-, trimethylsilylethyl-, triethylsilyl-, optionally substituted trimethylsilyl-, and optionally substituted trimethylsilylOCH$_2$—; and B is H, a pyrimidine base, a purine base, a heterocyclic base, adenine, guanine, uracil, cytosine, thymine, inosine, xanthine, hypoxanthine, isocytosine, isoguanine, 2-aminoadenosine, 5-methylcytosine, 2,6-diaminopurine, phenyl, naphthyl, 3-nitropyrrole, 5-nitroindole, nebularine, pyridone, pyridinone, diflurotolyl, or any other naturally occurring or non-naturally occurring base with or without suitable protecting groups.

In some embodiments, a compound having Formula I is:

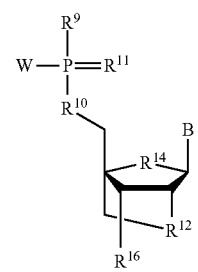

wherein, each $R^9$ is independently OH, SH, C(O)H, S(O)H, $C_{1-6}$ alkyl, $C_{1-6}$ alkyl substituted with one or more hydroxyl groups, $C_{1-6}$ alkyl substituted with one or more halo groups;

each $R^{10}$ is independently O, S, C(O), S(O), $C_{1-6}$ alkyl, $C_{1-6}$ alkyl substituted with one or more hydroxyl groups, $C_{1-6}$ alkyl substituted with one or more halo groups;

$R^{11}$ is S or O;

$R^{12}$ is O, S, $C_{1-6}$alkyl, $CH_2$, substituted $C_{1-6}$alkyl, NH or substituted N;

$R^{14}$ is O, S, $CH_2$, S=O, CHF, or $CF_2$; and $R^{16}$ is H, OH or azide; and B is H, a pyrimidine base, a purine base, a heterocyclic base, adenine, guanine, uracil, cytosine, thymine, inosine, xanthine, hypoxanthine, isocytosine, isoguanine, 2-aminoadenosine, 5-methylcytosine, 2,6-diaminopurine, phenyl, naphthyl, 3-nitropyrrole, 5-nitroindole, nebularine, pyridone, pyridinone, diflurotolyl, or any other naturally occurring or non-naturally occurring base with or without suitable protecting groups.

In some embodiments, a compound having Formula I is:

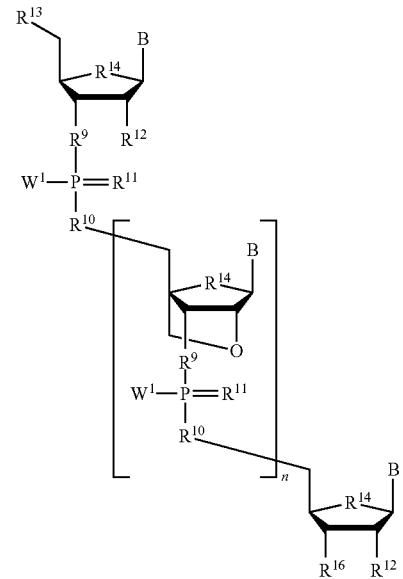

wherein, n is an integer from 0 to about 10,000;

each $W^1$ is independently OH, SH, $C_{1-6}$ alkyl, cyanoethyl, or W according to Formula I, with at least one $W^1$ being W of Formula I;

each $R^9$ and $R^{10}$ is independently O, S, C(O), S(O), $C_{1-6}$ alkyl, $C_{1-6}$ alkyl substituted with one or more hydroxyl groups, $C_{1-6}$ alkyl substituted with one or more halo groups;

each $R^{11}$ is independently S or O;

each $R^{12}$ is independently H, halo, $C_{1-6}$alkoxyl, $C_{1-6}$ alkenyl, $C_{1-6}$ alkenyl substituted with one or more hydroxyl groups, $C_{1-6}$ alkenyl substituted with one or more halo groups, or $-OR^{15}$;

$R^{13}$ is H, $-OH$, $-O$-trityl, substituted $-O$-trityl, $-O$-pixyl (9-phenylxanthenyl), substituted-O-pixyl (9-phenylxanthenyl), S-pixyl (9-phenylxanthenyl), substituted S-pixyl (9-phenylxanthenyl), halo, $C_{1-6}$alkoxyl, $C_{1-6}$ alkenyl, $C_{1-6}$ alkenyl substituted with one or more hydroxyl groups, $C_{1-6}$ alkenyl substituted with one or more halo groups, a phosphate group, a phosphodiester, or $-OR^{15}$;

each $R^{14}$ is independently O, S, $CH_2$, S=O, CHF, or $CF_2$;

each $R^{15}$ is independently H, triisopropylsilylOCH$_2$—, tert-butyldimethylsilylOCH$_2$—, triethylsilylOCH$_2$—, trimethylsilylethylOCH$_2$—, triisopropylsilyl-, tert-butyldimethylsilyl-, trimethylsilylethyl-, triethylsilyl-, optionally substituted trimethylsilyl-, and optionally substituted trimethylsilylOCH$_2$—;

$R^{16}$ is H, OH, or a capping moiety; wherein the capping moiety is selected from one or more abasic nucleotides, one or more inverted nucleotides, one or more PNAs, one or more LNAs, L-Y-X and O-Y-T; and each B is independently H, a pyrimidine base, a purine base, a heterocyclic base, adenine, guanine, uracil, cytosine, thymine, inosine, xanthine, hypoxanthine, isocytosine, isoguanine, 2-aminoadenosine, 5-methylcytosine, 2,6-diaminopurine, phenyl, naphthyl, 3-nitropyrrole, 5-nitroindole, nebularine, pyridone, pyridinone, diflurotolyl, or any other naturally occurring or non-naturally occurring base with or without suitable protecting groups.

In some embodiments, a compound having Formula I is:

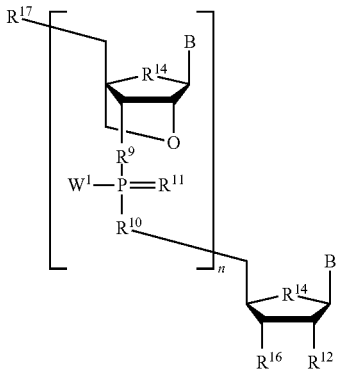

wherein, n is an integer from 1 to about 10,000;

each $W^1$ is independently OH, SH, $C_{1-6}$ alkyl, cyanoethyl, or W according to Formula I, with at least one $W^1$ being W of Formula I;

each $R^9$ and $R^{10}$ is independently O, S, C(O), S(O), $C_{1-6}$ alkyl, $C_{1-6}$ alkyl substituted with one or more hydroxyl groups, $C_{1-6}$ alkyl substituted with one or more halo groups;

each $R^{11}$ is independently S or O;

$R^{12}$ is H, halo, $C_{1-6}$alkoxyl, $C_{1-6}$ alkenyl, $C_{1-6}$ alkenyl substituted with one or more hydroxyl groups, $C_{1-6}$ alkenyl substituted with one or more halo groups, or $-OR^{15}$; each $R^{14}$ is independently O, S, $CH_2$, S=O, CHF, or $CF_2$;

$R^{15}$ is H, triisopropylsilylOCH$_2$—, tert-butyldimethylsilylOCH$_2$—, triethylsilylOCH$_2$—, trimethylsilylethylOCH$_2$—, triisopropylsilyl-, tert-butyldimethylsilyl-, trimethylsilylethyl-, triethylsilyl-, optionally substituted trimethylsilyl-, and optionally substituted trimethylsilylOCH$_2$—;

$R^{16}$ is H, OH, or a capping moiety; wherein the capping moiety is selected from one or more abasic nucleotides, one or more inverted nucleotides, one or more PNAs, one or more LNAs, X-L-Y and O-Y-T; where L is a linker and T is a solid support;

$R^{17}$ is H, OH, $C_{1-6}$ alkyl, $C_{1-6}$ alkyl substituted with one or more hydroxyl groups, $C_{1-6}$ alkyl substituted with one or more halo groups, $C_{1-6}$ alkenyl, $C_{1-6}$ alkenyl substituted with one or more hydroxyl groups, $C_{1-6}$ alkenyl substituted with one or more halo groups, $C_{1-6}$ alkynyl, $C_{1-6}$ alkynyl substituted with one or more hydroxyl groups, $C_{1-6}$ alkynyl substituted with one or more halo groups, $C_{1-6}$ alkoxyl, $C_{1-6}$ alkoxyl substituted with one or more hydroxyl groups, $C_{1-6}$ alkoxyl substituted with one or more halo groups, aryl, heteroaryl, heterocyclyl, —NHC$_{1-6}$ alkyl, aryl$C_{1-6}$ alkyl, heteroaryl$C_{1-6}$ alkyl, heterocyclyl$C_{1-6}$ alkyl, guanidinyl, $C_{1-6}$alkylC(O)O—, arylC(O)O—, heterocyclylC(O)O—, O-propargyl, S-propargyl, O-allyl, S-allyl, a capping moiety; wherein the capping moiety is selected from one or more abasic nucleotides, one or more inverted nucleotides, one or more PNAs, one or more LNAs, and X-L-Y;

wherein X is O, S, NH, C(O), S(O), $C_{1-6}$ alkyl, $C_{1-6}$ alkyl substituted with one or more hydroxyl groups, $C_{1-6}$ alkyl substituted with one or more halo groups, $C_{1-6}$ alkenyl, $C_{1-6}$ alkenyl substituted with one or more hydroxyl groups, $C_{1-6}$ alkenyl substituted with one or more halo groups, $C_{1-6}$ alkynyl, $C_{1-6}$ alkynyl substituted with one or more hydroxyl groups, $C_{1-6}$ alkynyl substituted with one or more halo groups, $C_{1-6}$ alkoxyl, $C_{1-6}$ alkoxyl substituted with one or more hydroxyl groups, $C_{1-6}$ alkoxyl substituted with one or more halo groups, aryl, heteroaryl, heterocyclyl, —NHC$_{1-6}$ alkyl, aryl$C_{1-6}$ alkyl, heteroaryl$C_{1-6}$ alkyl, heterocyclyl$C_{1-6}$ alkyl, guanidinyl, $C_{1-6}$alkylC(O)O—, arylC(O)O—, heterocyclylC(O)O—, O-propargyl, S-propargyl, O-allyl, S-allyl; L is a linker that is optionally present; Y is a targeting agent, ligand and/or polymer that is optionally present; and T is a solid support and each B is independently H, a pyrimidine base, a purine base, a heterocyclic base, adenine, guanine, uracil, cytosine, thymine, inosine, xanthine, hypoxanthine, isocytosine, isoguanine, 2-aminoadenosine, 5-methylcytosine, 2,6-diaminopurine, phenyl, naphthyl, 3-nitropyrrole, 5-nitroindole, nebularine, pyridone, pyridinone, diflurotolyl, or any other naturally occurring or non-naturally occurring base with or without suitable protecting groups.

In some embodiments, with respect to any compound having Formula I, W is:

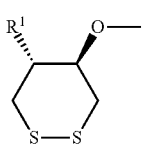

wherein R$^1$ is H, OH, C$_{1-6}$ alkyl, C$_{1-6}$ alkyl substituted with one or more hydroxyl groups, C$_{1-6}$ alkyl substituted with one or more halo groups, C$_{1-6}$ alkenyl, C$_{1-6}$ alkenyl substituted with one or more hydroxyl groups, C$_{1-6}$ alkenyl substituted with one or more halo groups, C$_{1-6}$ alkynyl, C$_{1-6}$ alkynyl substituted with one or more hydroxyl groups, C$_{1-6}$ alkynyl substituted with one or more halo groups, C$_{1-6}$ alkoxyl, C$_{1-6}$ alkoxyl substituted with one or more hydroxyl groups, C$_{1-6}$ alkoxyl substituted with one or more halo groups, aryl, heteroaryl, heterocyclyl, —NHC$_{1-6}$ alkyl, arylC$_{1-6}$ alkyl, heteroarylC$_{1-6}$ alkyl, heterocyclylC$_{1-6}$ alkyl, guanidinyl, C$_{1-6}$alkylC(O)O—, arylC(O)O—, heterocyclylC(O)O—, O-propargyl, S-propargyl, O-allyl, S-allyl, or X-L-Y; wherein X is O, S, NH, C(O), S(O), C$_{1-6}$ alkyl, C$_{1-6}$ alkyl substituted with one or more hydroxyl groups, C$_{1-6}$ alkyl substituted with one or more halo groups, C$_{1-6}$ alkenyl, C$_{1-6}$ alkenyl substituted with one or more hydroxyl groups, C$_{1-6}$ alkenyl substituted with one or more halo groups, C$_{1-6}$ alkynyl, C$_{1-6}$ alkynyl substituted with one or more hydroxyl groups, C$_{1-6}$ alkynyl substituted with one or more halo groups, C$_{1-6}$ alkoxyl, C$_{1-6}$ alkoxyl substituted with one or more hydroxyl groups, C$_{1-6}$ alkoxyl substituted with one or more halo groups, aryl, heteroaryl, heterocyclyl, —NHC$_{1-6}$ alkyl, arylC$_{1-6}$ alkyl, heteroarylC$_{1-6}$ alkyl, heterocyclylC$_{1-6}$ alkyl, guanidinyl, C$_{1-6}$alkylC(O)O—, arylC(O)O—, heterocyclylC(O)O—, O-propargyl, S-propargyl, O-allyl, S-allyl; L is a linker that is optionally present; and Y is a targeting agent, ligand and/or polymer that is optionally present.

In some embodiments, with respect to any compound having Formula I, W is:

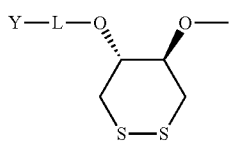

wherein L is a linker that is optionally present; and Y is a targeting agent, ligand and/or polymer.

In some embodiments, with respect to any compound having Formula I, W is:

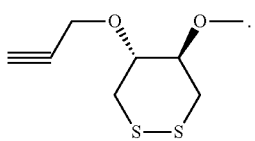

Also provided herein are compounds having Formula II:

(Formula II)

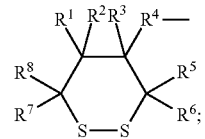

wherein,
W is:

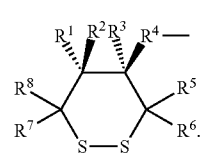

R$^1$ is H, OH, C$_{1-6}$ alkyl, C$_{1-6}$ alkyl substituted with one or more hydroxyl groups, C$_{1-6}$ alkyl substituted with one or more halo groups, C$_{1-6}$ alkenyl, C$_{1-6}$ alkenyl substituted with one or more hydroxyl groups, C$_{1-6}$ alkenyl substituted with one or more halo groups, C$_{1-6}$ alkynyl, C$_{1-6}$ alkynyl substituted with one or more hydroxyl groups, C$_{1-6}$ alkynyl substituted with one or more halo groups, C$_{1-6}$ alkoxyl, C$_{1-6}$ alkoxyl substituted with one or more hydroxyl groups, C$_{1-6}$ alkoxyl substituted with one or more halo groups, aryl, heteroaryl, heterocyclyl, —NHC$_{1-6}$ alkyl, arylC$_{1-6}$ alkyl, heteroarylC$_{1-6}$ alkyl, heterocyclylC$_{1-6}$ alkyl, guanidinyl, C$_{1-6}$alkylC(O)O—, arylC(O)O—, heterocyclylC(O)O—, O-propargyl, S-propargyl, O-allyl, S-allyl, or X-L-Y; wherein X is O, S, NH, C(O), S(O), C$_{1-6}$ alkyl, C$_{1-6}$ alkyl substituted with one or more hydroxyl groups, C$_{1-6}$ alkyl substituted with one or more halo groups, C$_{1-6}$ alkenyl, C$_{1-6}$ alkenyl substituted with one or more hydroxyl groups, C$_{1-6}$ alkenyl substituted with one or more halo groups, C$_{1-6}$ alkynyl, C$_{1-6}$ alkynyl substituted with one or more hydroxyl groups, C$_{1-6}$ alkynyl substituted with one or more halo groups, C$_{1-6}$ alkoxyl, C$_{1-6}$ alkoxyl substituted with one or more hydroxyl groups, C$_{1-6}$ alkoxyl substituted with one or more halo groups, aryl, heteroaryl, heterocyclyl, —NHC$_{1-6}$ alkyl, arylC$_{1-6}$ alkyl, heteroarylC$_{1-6}$ alkyl, heterocyclylC$_{1-6}$ alkyl, guanidinyl, C$_{1-6}$alkylC(O)O—, arylC(O)O—, heterocyclylC(O)O—, O-propargyl, S-propargyl, O-allyl, S-allyl; L is a linker that is optionally present; and Y is a targeting agent, ligand and/or polymer that is optionally present;
R$^4$ is S or O covalently attached to P;
each R$^2$, R$^3$, R$^5$, R$^6$, R$^7$ and R$^8$ is independently halo or R$^1$ as above; and
each R$^9$ is individually C$_{1-6}$ alkyl.

In some embodiments, with respect to a compound having Formula II, W is racemic with respect to R$^1$ and R$^4$.

In some embodiments, with respect to a compound having Formula II, R$^1$ and R$^4$ of W are in trans as shown in Formula Wt:

(Formula Wt)

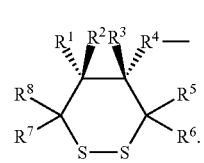

In some embodiments, with respect to a compound having Formula II, R$^1$ and R$^4$ of W are in cis as shown in Formula Wc:

(Formula Wc)

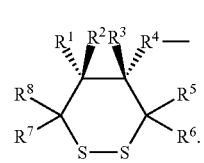

In some embodiments, a compound having Formula II is:

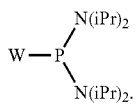

In some embodiments, a compound having Formula II is:

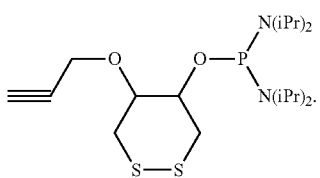

In some embodiments, a compound having Formula II is:

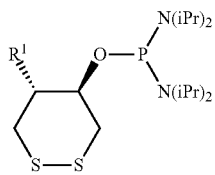

wherein,
$R^1$ is $C_{1-6}$ alkyl, $C_{1-6}$ alkyl substituted with one or more hydroxyl groups, $C_{1-6}$ alkyl substituted with one or more halo groups, $C_{1-6}$ alkenyl, $C_{1-6}$ alkenyl substituted with one or more hydroxyl groups, $C_{1-6}$ alkenyl substituted with one or more halo groups, $C_{1-6}$ alkynyl, $C_{1-6}$ alkynyl substituted with one or more hydroxyl groups, $C_{1-6}$ alkynyl substituted with one or more halo groups, $C_{1-6}$ alkoxyl, $C_{1-6}$ alkoxyl substituted with one or more hydroxyl groups, $C_{1-6}$ alkoxyl substituted with one or more halo groups, aryl, heteroaryl, heterocyclyl, —NH$C_{1-6}$ alkyl, aryl$C_{1-6}$ alkyl, heteroaryl$C_{1-6}$ alkyl, heterocyclyl$C_{1-6}$ alkyl, guanidinyl, $C_{1-6}$alkylC(O)O—, arylC(O)O—, heterocyclylC(O)O—, O-propargyl, S-propargyl, O-allyl, S-allyl, or X-L-Y; and
X is O, S, NH, C(O), S(O), $C_{1-6}$ alkyl, $C_{1-6}$ alkyl substituted with one or more hydroxyl groups, $C_{1-6}$ alkyl substituted with one or more halo groups, $C_{1-6}$ alkenyl, $C_{1-6}$ alkenyl substituted with one or more hydroxyl groups, $C_{1-6}$ alkenyl substituted with one or more halo groups, $C_{1-6}$ alkynyl, $C_{1-6}$ alkynyl substituted with one or more hydroxyl groups, $C_{1-6}$ alkynyl substituted with one or more halo groups, $C_{1-6}$ alkoxyl, $C_{1-6}$ alkoxyl substituted with one or more hydroxyl groups, $C_{1-6}$ alkoxyl substituted with one or more halo groups, aryl, heteroaryl, heterocyclyl, —NH$C_{1-6}$ alkyl, aryl$C_{1-6}$ alkyl, heteroaryl$C_{1-6}$ alkyl, heterocyclyl$C_{1-6}$ alkyl, guanidinyl, $C_{1-6}$alkylC(O)O—, arylC(O)O—, heterocyclylC(O)O—, O-propargyl, S-propargyl, O-allyl, S-allyl; L is a linker that is optionally present; and Y is a targeting agent, ligand and/or polymer that is optionally present.

In some embodiments, a compound having Formula II is:

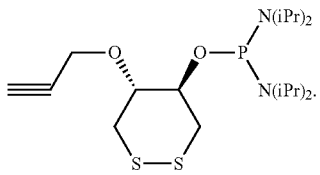

Also provided herein are compounds having Formula III:

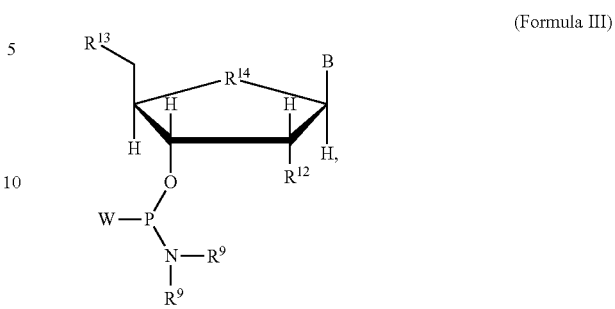

(Formula III)

wherein,
W is:

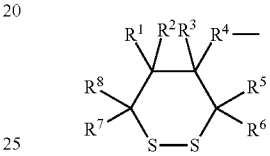

$R^1$ is H, OH, $C_{1-6}$ alkyl, $C_{1-6}$ alkyl substituted with one or more hydroxyl groups, $C_{1-6}$ alkyl substituted with one or more halo groups, $C_{1-6}$ alkenyl, $C_{1-6}$ alkenyl substituted with one or more hydroxyl groups, $C_{1-6}$ alkenyl substituted with one or more halo groups, $C_{1-6}$ alkynyl, $C_{1-6}$ alkynyl substituted with one or more hydroxyl groups, $C_{1-6}$ alkynyl substituted with one or more halo groups, $C_{1-6}$ alkoxyl, $C_{1-6}$ alkoxyl substituted with one or more hydroxyl groups, $C_{1-6}$ alkoxyl substituted with one or more halo groups, aryl, heteroaryl, heterocyclyl, —NH$C_{1-6}$ alkyl, aryl$C_{1-6}$ alkyl, heteroaryl$C_{1-6}$ alkyl, heterocyclyl$C_{1-6}$ alkyl, guanidinyl, $C_{1-6}$alkylC(O)O—, arylC(O)O—, heterocyclylC(O)O—, O-propargyl, S-propargyl, O-allyl, S-allyl, or X-L-Y;
wherein X is O, S, NH, C(O), S(O), $C_{1-6}$ alkyl, $C_{1-6}$ alkyl substituted with one or more hydroxyl groups, $C_{1-6}$ alkyl substituted with one or more halo groups, $C_{1-6}$ alkenyl, $C_{1-6}$ alkenyl substituted with one or more hydroxyl groups, $C_{1-6}$ alkenyl substituted with one or more halo groups, $C_{1-6}$ alkynyl, $C_{1-6}$ alkynyl substituted with one or more hydroxyl groups, $C_{1-6}$ alkynyl substituted with one or more halo groups, $C_{1-6}$ alkoxyl, $C_{1-6}$ alkoxyl substituted with one or more hydroxyl groups, $C_{1-6}$ alkoxyl substituted with one or more halo groups, aryl, heteroaryl, heterocyclyl, —NH$C_{1-6}$ alkyl, aryl$C_{1-6}$ alkyl, heteroaryl$C_{1-6}$ alkyl, heterocyclyl$C_{1-6}$ alkyl, guanidinyl, $C_{1-6}$alkylC(O)O—, arylC(O)O—, heterocyclylC(O)O—, O-propargyl, S-propargyl, O-allyl, S-allyl;
L is a linker that is optionally present; and Y is a targeting agent, ligand and/or polymer that is optionally present;
$R^4$ is S or O covalently attached to P;
each $R^2$, $R^3$, $R^5$, $R^6$, $R^7$ and $R^8$ is independently halo or $R^1$ as above;
$R^{12}$ is H, halo, $C_{1-6}$alkoxyl, $C_{1-6}$ alkenyl, $C_{1-6}$ alkenyl substituted with one or more hydroxyl groups, $C_{1-6}$ alkenyl substituted with one or more halo groups, or —OR$^{15}$;
$R^{13}$ is H, —O-trityl, substituted —O-trityl, —O-pixyl (9-phenylxanthenyl), substituted-O-pixyl (9-phenylxanthenyl), S-pixyl (9-phenylxanthenyl), substituted S-pixyl (9-phenylxanthenyl), halo, $C_{1-6}$alkoxyl, $C_{1-6}$ alkenyl, $C_{1-6}$ alkenyl substituted with one or more hydroxyl groups, $C_{1-6}$ alkenyl substituted with one or more halo groups, a phosphate group, a phosphodiester, or —OR$^{15}$;

R$^{14}$ is O, S, CH$_2$, S=O, CHF, or CF$_2$;

R$^{15}$ is H, triisopropylsilylOCH$_2$—, tert-butyldimethylsilylOCH$_2$—, triethylsilylOCH$_2$—, trimethylsilylethylOCH$_2$—, triisopropylsilyl-, tert-butyldimethylsilyl-, trimethylsilylethyl-, triethylsilyl-, optionally substituted trimethylsilyl-, and optionally substituted trimethylsilylOCH$_2$—; and B is H, a pyrimidine base, a purine base, a heterocyclic base, adenine, guanine, uracil, cytosine, thymine, inosine, xanthine, hypoxanthine, isocytosine, isoguanine, 2-aminoadenosine, 5-methylcytosine, 2,6-diaminopurine, phenyl, naphthyl, 3-nitropyrrole, 5-nitroindole, nebularine, pyridone, pyridinone, diflurotolyl, or any other naturally occurring or non-naturally occurring base with or without suitable protecting groups.

In some embodiments, with respect to a compound having Formula III, W is racemic with respect to R$^1$ and R$^4$.

In some embodiments, with respect to a compound having Formula III, R$^1$ and R$^4$ of W are in trans as shown in Formula Wt:

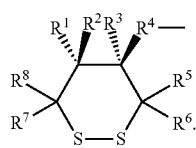

(Formula Wt)

In some embodiments, with respect to a compound having Formula III, R$^1$ and R$^4$ of W are in cis as shown in Formula Wc:

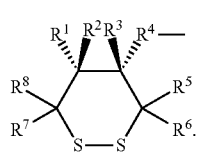

(Formula Wc)

In some embodiments, a compound having Formula III is:

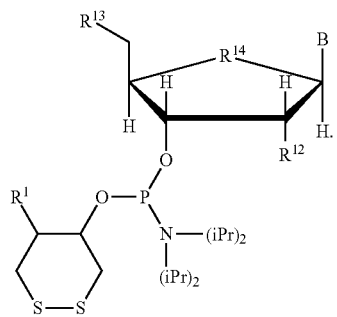

In some embodiments, a compound having Formula III is:

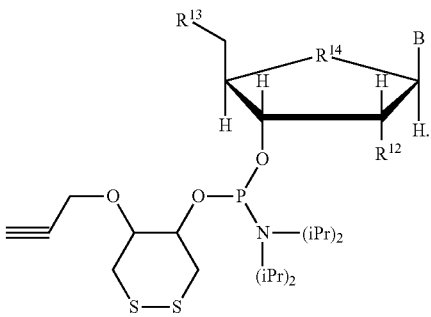

In some embodiments, a compound having Formula III is:

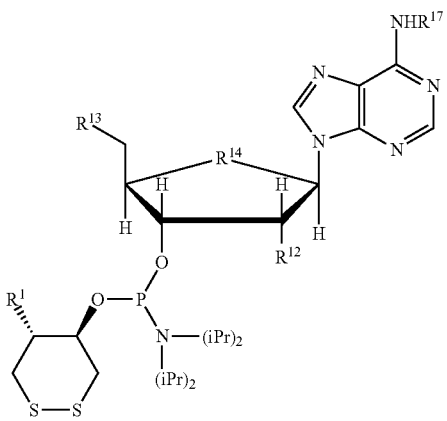

wherein R$^{17}$ is H, acetyl, benzoyl, phenoxyacetyl (PAC), or any other adenosine protecting group.

In some embodiments, a compound having Formula III is:

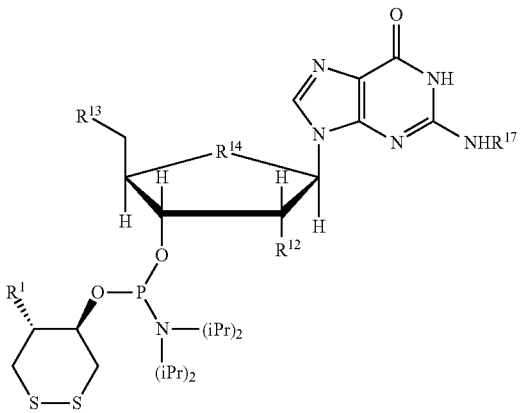

wherein R$^{17}$ is H, isobutyryl, isopropylphenoxyacetyl, phenoxyacetyl (PAC), or any other guanosine protecting group.

In some embodiments, a compound having Formula III is:

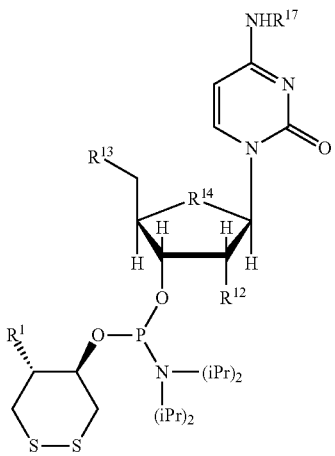

wherein R$^{17}$ is H, benzoyl or any other cytidine protecting group.

In some embodiments, a compound having Formula III is:

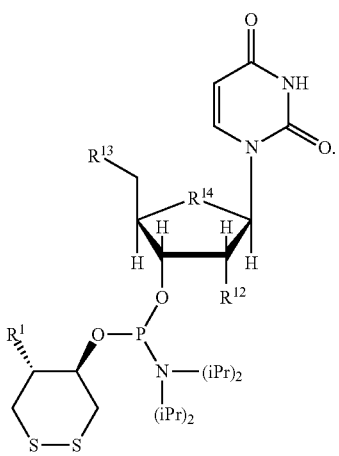

In some embodiments, a compound having Formula III is:

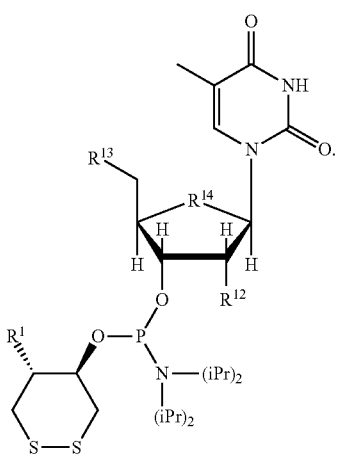

Also provided herein are compounds having Formula IV:

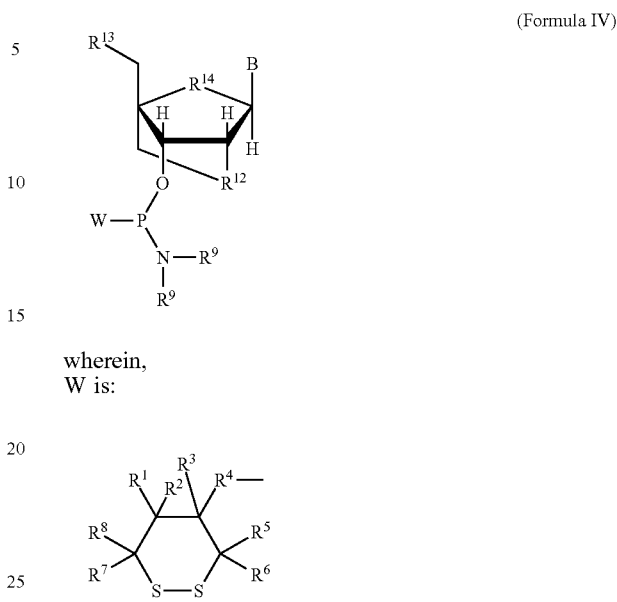

(Formula IV)

wherein,
W is:

R$^1$ is H, OH, C$_{1-6}$ alkyl, C$_{1-6}$ alkyl substituted with one or more hydroxyl groups, C$_{1-6}$ alkyl substituted with one or more halo groups, C$_{1-6}$ alkenyl, C$_{1-6}$ alkenyl substituted with one or more hydroxyl groups, C$_{1-6}$ alkenyl substituted with one or more halo groups, C$_{1-6}$ alkynyl, C$_{1-6}$ alkynyl substituted with one or more hydroxyl groups, C$_{1-6}$ alkynyl substituted with one or more halo groups, C$_{1-6}$ alkoxyl, C$_{1-6}$ alkoxyl substituted with one or more hydroxyl groups, C$_{1-6}$ alkoxyl substituted with one or more halo groups, aryl, heteroaryl, heterocyclyl, —NHC$_{1-6}$ alkyl, arylC$_{1-6}$ alkyl, heteroarylC$_{1-6}$ alkyl, heterocyclylC$_{1-6}$ alkyl, guanidinyl, C$_{1-6}$alkylC(O)O—, arylC(O)O—, heterocyclylC(O)O—, O-propargyl, S-propargyl, O-allyl, S-allyl, or X-L-Y;
wherein X is O, S, NH, C(O), S(O), C$_{1-6}$ alkyl, C$_{1-6}$ alkyl substituted with one or more hydroxyl groups, C$_{1-6}$ alkyl substituted with one or more halo groups, C$_{1-6}$ alkenyl, C$_{1-6}$ alkenyl substituted with one or more hydroxyl groups, C$_{1-6}$ alkenyl substituted with one or more halo groups, C$_{1-6}$ alkynyl, C$_{1-6}$ alkynyl substituted with one or more hydroxyl groups, C$_{1-6}$ alkynyl substituted with one or more halo groups, C$_{1-6}$ alkoxyl, C$_{1-6}$ alkoxyl substituted with one or more hydroxyl groups, C$_{1-6}$ alkoxyl substituted with one or more halo groups, aryl, heteroaryl, heterocyclyl, —NHC$_{1-6}$ alkyl, arylC$_{1-6}$ alkyl, heteroarylC$_{1-6}$ alkyl, heterocyclylC$_{1-6}$ alkyl, guanidinyl, C$_{1-6}$alkylC(O)O—, arylC(O)O—, heterocyclylC(O)O—, O-propargyl, S-propargyl, O-allyl, S-allyl; L is a linker that is optionally present; and Y is a targeting agent, ligand and/or polymer that is optionally present;
R$^4$ is S or O covalently attached to P;
each R$^2$, R$^3$, R$^5$, R$^6$, R$^7$ and R$^8$ is independently halo or R$^1$ as above;
each R$^9$ is individually C$_{1-6}$ alkyl;
R$^{12}$ is O, S, C$_{1-6}$alkyl, CH$_2$, substituted C$_{1-6}$alkyl, NH or substituted N;
R$^{13}$ is H, —O-trityl, substituted —O-trityl, —O-pixyl (9-phenylxanthenyl), substituted-O-pixyl (9-phenylxanthenyl), S-pixyl (9-phenylxanthenyl), substituted S-pixyl (9-phenylxanthenyl), halo, C$_{1-6}$alkoxyl, C$_{1-6}$ alkenyl, C$_{1-6}$ alkenyl substituted with one or more hydroxyl groups, C$_{1-6}$ alkenyl substituted with one or more halo groups, a phosphate group, a phosphodiester, or —OR$^{15}$;
R$^{14}$ is O, S, CH$_2$, S=O, CHF, or CF$_2$;

$R^{15}$ is H, triisopropylsilylOCH$_2$—, tert-butyldimethylsilylOCH$_2$—, triethylsilylOCH$_2$—, trimethylsilylethylOCH$_2$—, triisopropylsilyl-, tert-butyldimethylsilyl-, trimethylsilylethyl-, triethylsilyl-, optionally substituted trimethylsilyl-, and optionally substituted trimethylsilylOCH$_2$—; and B is independently H, a pyrimidine base, a purine base, a heterocyclic base, adenine, guanine, uracil, cytosine, thymine, inosine, xanthine, hypoxanthine, isocytosine, isoguanine, 2-aminoadenosine, 5-methylcytosine, 2,6-diaminopurine, phenyl, naphthyl, 3-nitropyrrole, 5-nitroindole, nebularine, pyridone, pyridinone, diflurotolyl, or any other naturally occurring or non-naturally occurring base with or without suitable protecting groups.

In some embodiments, with respect to a compound having Formula IV, W is racemic with respect to R' and $R^4$.

In some embodiments, with respect to a compound having Formula IV, $R^1$ and $R^4$ of W are in trans as shown in Formula Wt:

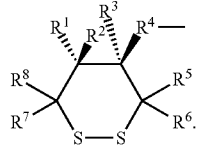

(Formula Wt)

In some embodiments, with respect to a compound having Formula IV, $R^1$ and $R^4$ of W are in cis as shown in Formula Wc:

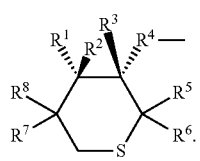

(Formula Wc)

In some embodiments, a compound having Formula IV is:

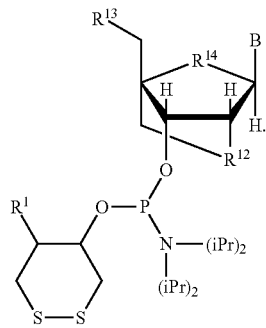

In some embodiments, a compound having Formula IV is:

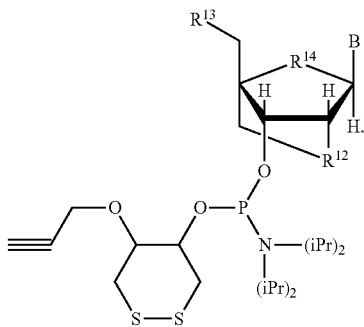

In some embodiments, a compound having Formula IV is:

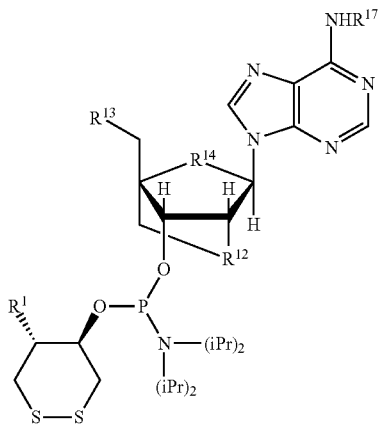

wherein $R^{17}$ is H, acetyl, benzoyl, phenoxyacetyl (PAC), or any other adenosine protecting group.

In some embodiments, a compound having Formula IV is:

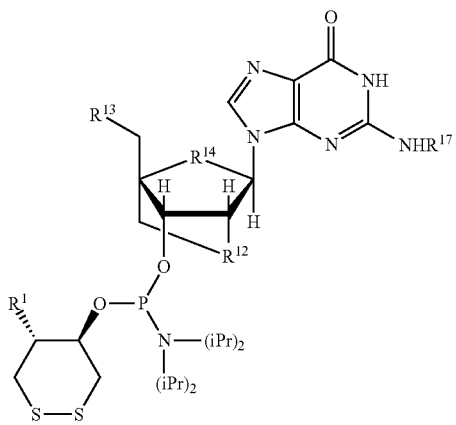

wherein $R^{17}$ is H, isobutyryl, isopropylphenoxyacetyl, phenoxyacetyl (PAC), or any other guanosine protecting group.

In some embodiments, a compound having Formula IV is:

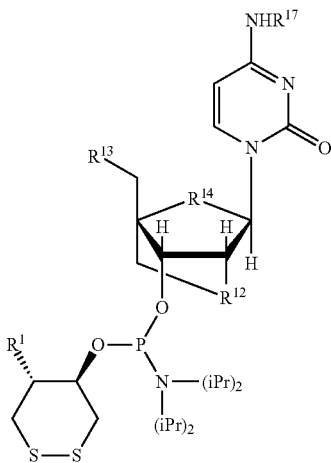

wherein $R^{17}$ is H, benzoyl or any other cytidine protecting group.

In some embodiments, a compound having Formula IV is:

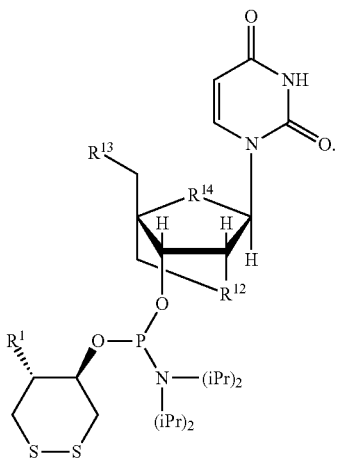

In some embodiments, a compound having Formula IV is:

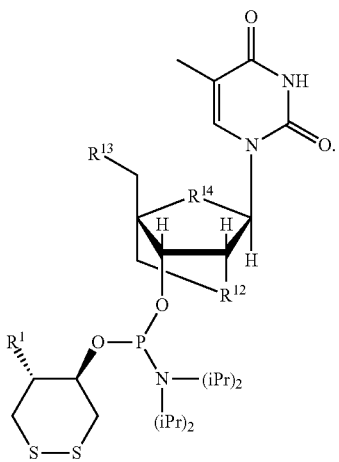

In certain embodiments, with reference to any compound having Formula I, II, III or IV above when Y is present, Y comprises one or more N-Acetyl Galactosamine moieties.

In certain embodiments, with reference to any compound having Formula I, II, III or IV above when Y is present, Y comprises one or more folate moieties.

In certain embodiments, with reference to any compound having Formula I, II, III or IV above when Y is present, Y comprises one or more peptide moieties.

In certain embodiments, with reference to any compound having Formula I, II, III or IV above when Y is present, Y comprises one or more steroid moieties.

In certain embodiments, with reference to any compound having Formula I, II, III or IV above when Y is present, Y comprises one or more vitamin or co-factor moieties.

In certain embodiments, with reference to any compound having Formula I, II, III or IV above when Y is present, Y comprises:

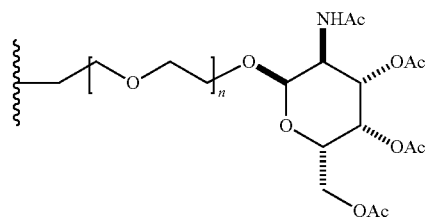

wherein n is an integer between 1 and 100.

In certain embodiments, with reference to any compound having Formula I, II, III or IV above when Y is present, Y comprises:

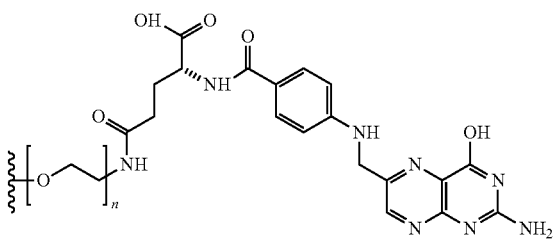

wherein n is an integer between 1 and 100.

In certain embodiments, with reference to any compound having Formula I, II, III or IV above when Y is present, Y comprises:

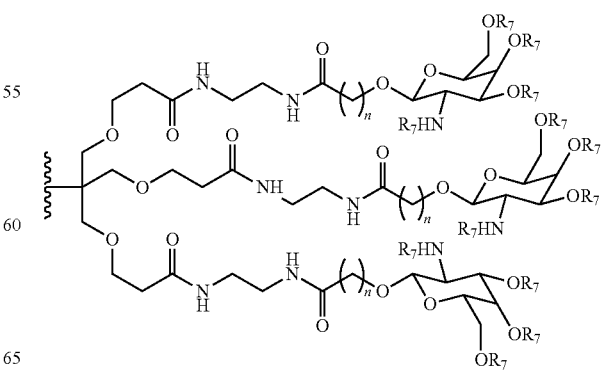

wherein each R₇ independently comprises an acetyl group, and each n is independently an integer from 1 to 20.

In certain embodiments, with reference to any compound having Formula I, II, III or IV above when Y is present, Y comprises:

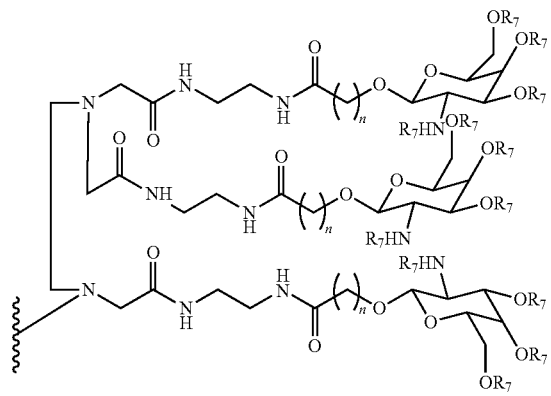

wherein each R₇ independently comprises an acetyl group, and each n is independently an integer from 1 to 20.

In certain embodiments, with reference to any compound having Formula I, II, III or IV above when Y is present, Y comprises:

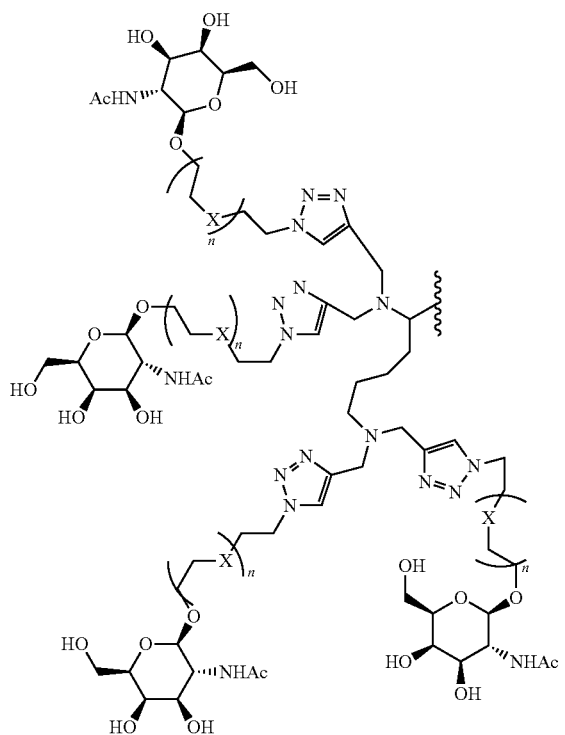

wherein X is —O—, —S—, —CR¹R²— or —NR¹—, wherein R¹ and R² are each independently selected from the group consisting of hydrogen and $C_1$-$C_6$ alkyl; n is 1, 2, 3, or 4.

In certain embodiments, with reference to any compound having Formula I, II, III or IV above when Y is present, Y comprises:

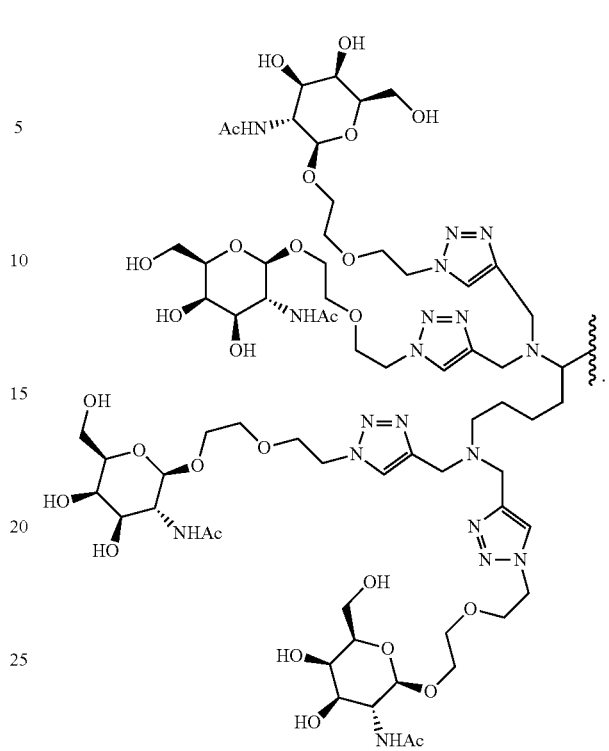

In certain embodiments, with reference to any compound having Formula I, II, III or IV above when L is present, L is a linker comprising an alkyl, carbonyl, amide, phosphate, phosphate ester, phosphoramidate, thiophosphate ester, disulfide, or polyalklene glycol linkage.

In certain embodiments, the invention features a composition comprising any compound having Formula I, II, III or IV above or a pharmaceutically acceptable salt, solvate, ester, or prodrug thereof.

In certain embodiments, the invention features a composition comprising any compound having Formula I, II, III or IV above and a pharmaceutically acceptable carrier or diluent.

C. Therapeutic Applications

In certain applications, the compounds and compositions of the invention are applied for therapeutic use.

Thus, one aspect of the invention comprises a method of treating a subject including, but not limited to, a human suffering from a disease or a condition, which method comprises administering to said subject an effective amount of a compound or composition of the invention. In one embodiment of this aspect, the compound comprises any of Formula I, II, III or IV herein.

In certain embodiments, the invention features the use of a therapeutically effective amount of at least one compound having Formula I, II, III or IV above, or a pharmaceutically acceptable salt, solvate, ester or prodrug thereof, for the manufacture of a medicament for treatment of a patient in need thereof.

In certain embodiments, the invention features the use of a therapeutically effective amount of at least one compound having Formula I, II, III or IV above, or a pharmaceutically acceptable salt, solvate, ester or prodrug thereof, for the treatment of a patient in need thereof.

In certain embodiments, the invention features the use of a therapeutically effective amount of at least one compound having Formula I, II, III or IV above, or a pharmaceutically acceptable salt, solvate, ester or prodrug thereof, for the treatment of viral infection in a patient in need thereof. Non-limiting examples of such viral infections include HCV, HBV, HPV, HSV or HIV infection.

In certain embodiments, the invention features the use of a therapeutically effective amount of at least one compound having Formula I, II, III or IV above, or a pharmaceutically acceptable salt, solvate, ester or prodrug thereof, for the treatment of cancer in a patient in need thereof. Non-limiting examples of such cancers include bilary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, wilms tumor, leukemia, acute lymocytic leukemia (ALL), acute myeloid leukemia (AML), chronic lymphocytic (CLL), chronic myeloid (CML), chronic myelomonocytic (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T-cell lymphomas, non-Hodgkin lymphoma, precursor T-lymphoblastic lymphoma/leukemia, peripheral T-cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas, Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma.

In some embodiments of this aspect, the disease or condition may be cancer, a proliferative, inflammatory, autoimmune, neurologic, ocular, respiratory, metabolic, dermatological, auditory, liver, kidney, or infectious disease as described herein or otherwise known in the art. Thus, in certain embodiments the compounds and compositions of the instant invention may be useful in a method for treating cancer, proliferative, inflammatory, autoimmune, neurologic, ocular, respiratory, metabolic, dermatological, auditory, liver, kidney, or infectious diseases.

In certain embodiments, the administration of the compound or composition may be via local administration or systemic administration. In other embodiments, the invention features contacting the subject or organism with a compound or composition of the invention via local administration to relevant tissues or cells, such as lung cells and tissues, such as via pulmonary delivery. In yet other embodiments, the invention features contacting the subject or organism with a compound or composition of the invention via systemic administration (such as via intravenous or subcutaneous administration) to relevant tissues or cells in a subject or organism.

Compounds and compositions of the invention may also used as reagents in ex vivo applications. For example, a compound or composition may be introduced into tissue or cells that are transplanted into a subject for therapeutic effect. The cells and/or tissue may be derived from an organism or subject that later receives the explant, or may be derived from another organism or subject prior to transplantation. The compound or composition may be used to modulate the expression of one or more genes in the cells or tissue, such that the cells or tissue obtain a desired phenotype or are able to perform a function when transplanted in vivo. In one embodiment, certain target cells from a patient are extracted. These extracted cells are contacted with compounds of the invention targeting a specific nucleotide sequence within the cells under conditions suitable for uptake of the compounds by these cells (e.g., using delivery reagents such as cationic lipids, liposomes and the like or using techniques such as electroporation to facilitate the delivery of compounds into cells). The cells are then reintroduced back into the same patient or other patients.

For therapeutic applications, a pharmaceutically effective dose of the compound or pharmaceutical composition of the invention is administered to the subject. A pharmaceutically effective dose is that dose required to prevent, inhibit the occurrence, or treat (alleviate a symptom to some extent, preferably all of the symptoms) a disease state. One skilled in the art may readily determine a therapeutically effective dose of the compound or composition of the invention to be administered to a given subject, by taking into account factors, such as the size and weight of the subject, the extent of the disease progression or penetration, the age, health, and sex of the subject, the route of administration, and whether the administration is regional or systemic. Generally, an amount between 0.1 µg/kg and 140 mg/kg body weight/day of active ingredients is administered dependent upon potency of the compounds of the disclosure. The amount of active ingredient that may be combined with the carrier materials to produce a single dosage form varies depending upon the host treated and the particular mode of administration. Optimal dosing schedules may be calculated from measurements of drug accumulation in the body of the patient. The a compounds and compositions of the invention may be administered in a single dose or in multiple doses.

A compound or composition of the instant invention may be administered once monthly, once weekly, once daily (QD), or divided into multiple monthly, weekly, or daily doses, such as, for example, but not limitation, twice daily (BID), three times daily (TID), once every two weeks. Persons of ordinary skill in the art may easily estimate repetition rates for dosing based on measured residence times and concentrations of the drug in bodily fluids or tissues.

In addition, the administration may be continuous, i.e., every day, or intermittently. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

D. Administration

Compositions or formulations of the invention may be administered in a variety of ways. Non-limiting examples of administration methods of the invention include oral, buccal, sublingual, parenteral (i.e., intraarticularly, intravenously, intraperitoneally, subcutaneously, or intramuscularly), local rectal administration or other local administration. In one embodiment, the composition of the invention may be administered by insufflation and inhalation. Administration may be accomplished via single or divided doses. In some embodiments, the pharmaceutical compositions are administered intravenously or intraperitoneally by a bolus injection (see, e.g., U.S. Pat. No. 5,286,634).

A composition of the invention with or without a vehicle may be locally delivered by direct injection or by use of an infusion pump. Direct injection of the compounds and compositions of this disclosure, whether subcutaneous, intramuscular, or intradermal, may take place using standard needle and syringe methodologies, or by needle free technologies, such as those described in Conroy et al, (1999, Clin. Cancer Res. 5:2330) and PCT Publication No. WO 99/31262. For example, but not by limitation, lipid particles comprising the compounds of the invention may be administered by direct injection at the site of disease or by injection at a site distal from the site of disease (see, e.g., Culver, HUMAN GENE THERAPY, MaryAnn Liebert, Inc., Publishers, New York. pp. 70-71 (1994)). In one embodiment, the compounds of the invention and formulations or compositions thereof are administered to a cell, subject, or organism as is described herein and as is generally known in the art.

In Vivo Administration

In any of the methods of treatment of the invention, the compounds may be administered to the subject systemically as described herein or otherwise known in the art, either alone as a monotherapy or in combination with additional therapies described herein or as are known in the art. Systemic administration may include, for example, pulmonary (inhalation, nebulization etc.) intravenous, subcutaneous, intramuscular, catheterization, nasopharyngeal, transdermal, or oral/gastrointestinal administration as is generally known in the art.

In any of the methods of treatment or prevention of the invention, the compounds may be administered to the subject locally or to local tissues as described herein or otherwise known in the art, either alone as a monotherapy or in combination with additional therapies as are known in the art. Local administration may include, for example, inhalation, nebulization, catheterization, implantation, direct injection, dermal/transdermal application, patches, stenting, ear/eye drops, or portal vein administration to relevant tissues, or any other local administration technique, method or procedure, as is generally known in the art.

In one embodiment, the compounds of the invention and formulations or compositions thereof are administered to the liver as is generally known in the art (see for example Wen et al., 2004, World J Gastroenterol., 10, 244-9; Murao et al., 2002, Pharm Res., 19, 1808-14; Liu et al., 2003, gene Ther., 10, 180-7; Hong et al., 2003, J Pharm Pharmacol., 54, 51-8; Herrmann et al., 2004, Arch Virol., 149, 1611-7; and Matsuno et al., 2003, gene Ther., 10, 1559-66).

In one embodiment, the invention features the use of methods to deliver the compounds of the instant invention to hematopoietic cells, including monocytes and lymphocytes. These methods are described in detail by Hartmann et al., 1998, J. Phamacol. Exp. Ther., 285(2), 920-928; Kronenwett et al., 1998, Blood, 91(3), 852-862; Filion and Phillips, 1997, Biochim. Biophys. Acta., 1329(2), 345-356; Ma and Wei, 1996, Leuk. Res., 20(11/12), 925-930; and Bongartz et al., 1994, Nucleic Acids Research, 22(22), 4681-8.

In one embodiment, the compounds of the invention and formulations or compositions thereof are administered directly or topically (e.g., locally) to the dermis or follicles as is generally known in the art (see for example Brand, 2001, Curr. Opin. Mol. Ther., 3, 244-8; Regnier et al., 1998, J. Drug Target, 5, 275-89; Kanikkannan, 2002, BioDrugs, 16, 339-47; Wraight et al., 2001, Pharmacol. Ther., 90, 89-104; and Preat and Dujardin, 2001, STP PharmaSciences, 11, 57-68). In one embodiment, the compounds of the invention and formulations or compositions thereof are administered directly or topically using a hydroalcoholic gel formulation comprising an alcohol (e.g., ethanol or isopropanol), water, and optionally including additional agents such isopropyl myristate and carbomer 980. In other embodiments, the compounds are formulated to be administered topically to the nasal cavity. Topical preparations may be administered by one or more applications per day to the affected area; over skin areas occlusive dressings may advantageously be used. Continuous or prolonged delivery may be achieved by an adhesive reservoir system.

In one embodiment, compounds of the invention are administered iontophoretically, for example to a particular organ or compartment (e.g., the eye, back of the eye, heart, liver, kidney, bladder, prostate, tumor, CNS etc.). Non-limiting examples of iontophoretic delivery are described in, for example, WO 03/043689 and WO 03/030989, which are incorporated by reference in their entireties herein.

In one embodiment, the compounds of the invention and formulations or compositions thereof are administered to the lung as is described herein and as is generally known in the art. In another embodiment, the siNA molecules of the invention and formulations or compositions thereof are administered to lung tissues and cells as is described in U.S. Patent Publication Nos. 2006/0062758; 2006/0014289; and 2004/0077540. *Aerosols and Delivery Devices* a. Aerosol Formulations

The compounds of the present invention, either alone or in combination with other suitable components, may be made into aerosol formulations (i.e., they may be "nebulized") to be administered via inhalation (e.g., intranasally or intratracheally) (see, Brigham et al., Am. J. Sci., 298:278 (1989)). Aerosol formulations may be placed into pressurized acceptable propellants, such as dichlorodifluoromethane, propane, nitrogen, and the like.

In one embodiment, the compounds of the invention and formulations thereof are administered via pulmonary delivery, such as by inhalation of an aerosol or spray dried formulation administered by an inhalation device or nebulizer, providing rapid local uptake of the nucleic acid molecules into relevant pulmonary tissues. Solid particulate compositions containing respirable dry particles of micronized compounds may be prepared by grinding dried or lyophilized compositions, and then passing the micronized composition through, for example, a 400 mesh screen to break up or separate out large agglomerates. A solid particulate composition comprising the compounds of the invention may optionally contain a dispersant which serves to facilitate the formation of an aerosol as well as other therapeutic compounds. A suitable dispersant is lactose, which may be blended with the compound in any suitable ratio, such as a 1 to 1 ratio by weight.

Spray compositions comprising compounds or compositions of the invention may, for example, be formulated as aqueous solutions or suspensions or as aerosols delivered from pressurized packs, such as a metered dose inhaler, with the use of a suitable liquefied propellant. In one embodiment, aerosol compositions of the invention suitable for inhalation may be either a suspension or a solution and generally contain an compound of the invention and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants. Non-limiting examples include oleic acid, lecithin or an oligolactic acid or derivative such as those described in WO94/21229 and WO98/34596 and co-solvents for example ethanol. In one embodiment a pharmaceutical aerosol formulation of the invention comprising a compound of the invention and a fluorocarbon or hydrogen-containing chlorofluorocarbon or mixtures thereof as propellant, optionally in combination with a surfactant and/or a co-solvent.

The aerosol formulations of the invention may be buffered by the addition of suitable buffering agents.

Aerosol formulations may include optional additives including preservatives if the formulation is not prepared sterile. Non-limiting examples include, methyl hydroxybenzoate, anti-oxidants, flavorings, volatile oils, buffering agents and emulsifiers and other formulation surfactants. In one embodiment, fluorocarbon or perfluorocarbon carriers are used to reduce degradation and provide safer biocompatible non-liquid particulate suspension compositions of the invention. In another embodiment, a device comprising a nebulizer delivers a composition of the invention comprising fluorochemicals that are bacteriostatic thereby decreasing the potential for microbial growth in compatible devices. Capsules and cartridges comprising the composition of the invention for use in an inhaler or insufflator, of for example gelatin, may be formulated containing a powder mix for inhalation of a compound of the invention and a suitable powder base such as lactose or starch. In one embodiment, each capsule or cartridge contains a compound of the invention and one or more excipients. In another embodiment, the compound of the invention may be presented without excipients such as lactose The aerosol compositions of the present invention may be administered into the respiratory system as a formulation including particles of respirable size, e.g. particles of a size sufficiently small to pass through the nose, mouth and larynx upon inhalation and through the bronchi and alveoli of the lungs. In general, respirable particles range from about 0.5 to 10 microns in size. In one embodiment, the particulate range may be from 1 to 5 microns. In another embodiment, the particulate range may be from 2 to 3 microns. Particles of non-respirable size which are included in the aerosol tend to deposit in the throat and be swallowed, and the quantity of non-respirable particles in the aerosol is thus minimized. For nasal administration, a particle size in the range of 10-500 um is preferred to ensure retention in the nasal cavity.

In some embodiments, compounds of the invention are administered topically to the nose for example, for the treatment of rhinitis, via pressurized aerosol formulations, aqueous formulations administered to the nose by pressurized pump or by nebulization. Suitable formulations may contain water as the diluent or carrier for this purpose. In certain embodiments, the aqueous formulations for administration of the composition of the invention to the lung or nose may be provided with conventional excipients such as buffering agents, tonicity modifying agents and the like.

b. Devices

The compounds of the invention may be formulated and delivered as particles and/or aerosols as discussed above and dispensed from various aerosolization devices known by those of skill in the art.

Aerosols of liquid or non-liquid particles comprising a compound or formulation of the invention may be produced by any suitable means, such as with a device comprising a nebulizer (see for example U.S. Pat. No. 4,501,729) such as ultrasonic or air jet nebulizers.

Solid particle aerosols comprising a compound or formulation of the invention and surfactant may be produced with any solid particulate aerosol generator. One type of solid particle aerosol generator used with the compounds of the invention is an insufflator. A second type of illustrative aerosol generator comprises a metered dose inhaler ("MDI"). MDIs containing compounds or formulations taught herein may be prepared by methods of the art (for example, see Byron, above and WO96/32099).

The compounds may also be formulated as a fluid formulation for delivery from a fluid dispenser, such as those described and illustrated in WO05/044354.

In certain embodiments of the invention, nebulizer devices are used in applications for conscious, spontaneously breathing subjects, and for controlled ventilated subjects of all ages. The nebulizer devices may be used for targeted topical and systemic drug delivery to the lung. In one embodiment, a device comprising a nebulizer is used to deliver a compound or formulation of the invention locally to lung or pulmonary tissues. In another embodiment, a device comprising a nebulizer is used to deliver a compound or formulation of the invention systemically.

E. Examples

The invention will now be illustrated with the following non-limiting examples. Those of skill in the art will readily recognize a variety of non-critical parameters which can be changed or modified to yield essentially the same results.

Oligonucleotide based medicines have the opportunity to provide several new treatment platforms to address a variety of diseases and conditions that currently have unmet medical need. By conferring the ability to selectively modulate gene expression, i.e. by directly down-regulating or up-regulating genes of interest, oligonucleotide medicines are uniquely poised for changing the face of modern medicine. However, because oligonucleotides are labile polyanionic macromolecules with only limited capability to cross cell membranes, their development into successful drugs has been contingent on safe and effective delivery approaches. Moreover, oligonucleotides are readily metabolized into shorter oligonucleotides and ultimately nucleotides by the action of naturally occurring enzymes (endo- and exo-nucleases). To address this shortcoming, the phosphodiester backbone is often modified by inclusion of phosphothiotes, or with modification of the nucleotide sugar or base portion(s). Also, unmodified oligonucleotides can posses strong immunogenic properties, and extensive chemical modification of the sugar/phosphodiester backbone may be needed to abbrogate this action. However, these chemical alterations can often alter the inherent potency of oligonucleotide based therapeutics.

Conversion of the naturally occurring phosphodiester linkage to a biolabile phosphotriester offers an elegant solution to the problems described above. According to this approach, the oligonucleotide prodrug remains protected against nuclease induced cleavage while in transit to the target cell/tissue. After entering the target cells, the biolabile bond contained within the phosphotriester group is broken via a site-specific mechanism releasing the biologically active oligonucleotide molecule.

The naturally reductive environment of the cytoplasm can serve as a suitable release trigger, and a disulfide moiety present within the phosphotriester can serve as a biolabile linker. Moreover, since the disulfide moiety is readily reduced only in alkaline pH (such as that of the cytoplasm), these constructs are expected to be stable in endosomes/lysosomes as the pH of these compartments is typically mildly acidic.

The principle of the oligomer release is exemplified in Scheme 1. According to this example, the initial cleavage of a disulfide bond contained within a phosphotriester group of a oligonucleotide (1-1) can produce the unstable intermediate 1-2, which is expected to undergo a spontaneous, charge-dissipation driven cyclodeesterification to produce the bioactive nucleic acid molecule/oligonucleotide (1-4) and thiirane (1-3).

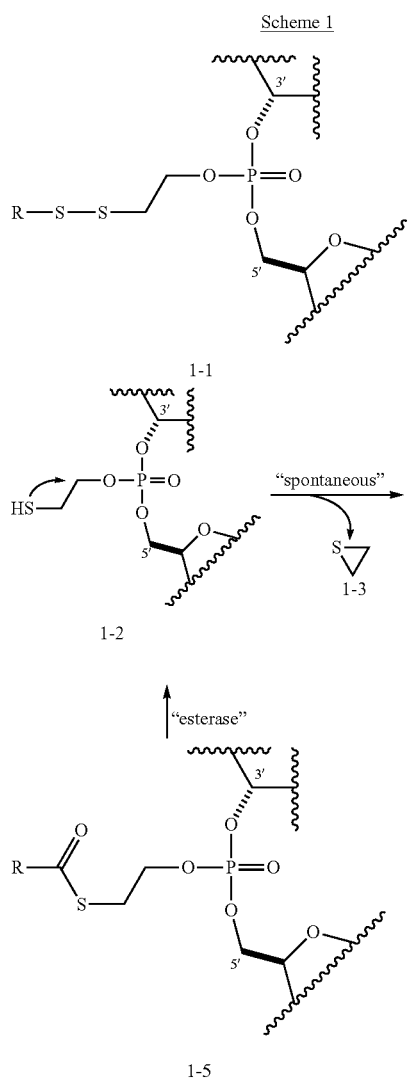

Scheme 1

The cyclodeesterification of 1-2 described in Scheme 1 is a spontaneous process and is expected to take place irrespective of the manner in which species 1-2 was produced. For example, S-acyl-2-thioethyl (SATE) prodrugs of oligonucleotides described by Petersen (WO 2010039543 A2, 2010, Traversa Therapeutics) are capable of producing the unstable intermediate 1-2 via an esterase-mediated hydrolysis of triesters such as 1-5, Scheme 1.

In spite of its elegance, the mechanism as described in Scheme 1 has inherent limitations. For example, linear disulfides are rather reactive and can readily react with the P(III) phosphorus usually present in these nucleoside building blocks. Similarly problematic is the use of esters such as 1-5, as these are easily decomposed with nucleophiles such as methylamine routinely used to to remove amide protecting groups present on nucleosides during oligonucleotide synthesis. However, perhaps the most problematic aspect of these thioethyl-based olignucleotide prodrugs is production of a reactive thiirane species. Besides deleterious acute effects, this reactive alkylating agent can, inter alia, readily react with nucleobases present naturally in DNA/RNA.

An effective solution to the above limitations, and the subject of the present invention, is described in Scheme 2. According to this approach, a cyclic disulfide moiety such as present in 2-1 can undergo a reduction analogous to that described in Scheme 1, producing intermediate 2-2. The nucleic acid/oligonucleotide of interest is released in a similar cyclodeesterification as in the case of the linear disulfides, however, the formed substituted thiirane (2-3) undergoes a rapid 1,5-exo-tet ring closure to produce a stable tetrahydrothiophene ring (2-5).

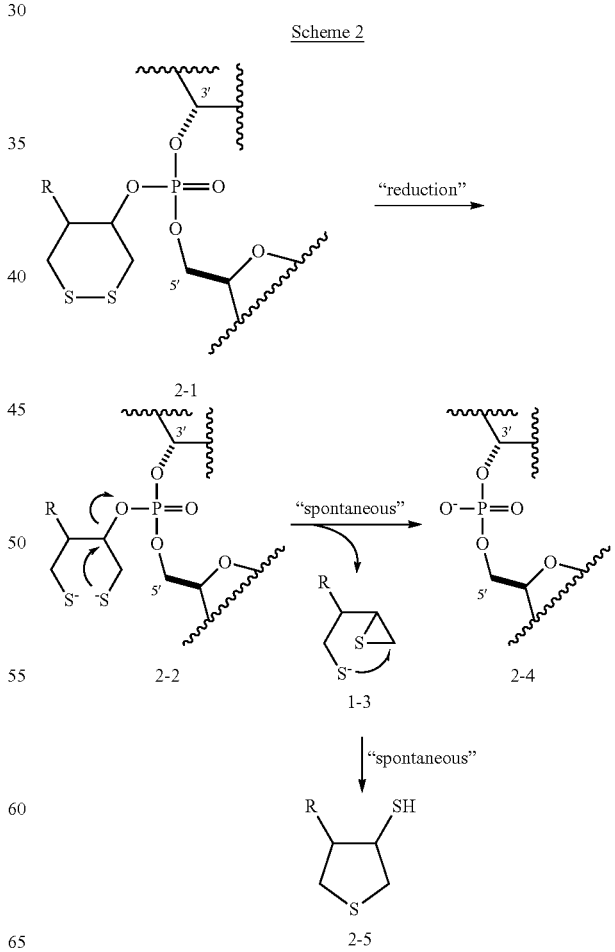

Scheme 2

To demonstrate the feasibility of this approach, a simple model oligomer was synthesized consisting of only two nucleosides UpU (5-2). The key intermediate, phosphoramidite 3-3 was prepared using either one of synthetic routes described in Scheme 3a. The commercially available 5'-dimethoxytrityl-2'-O-methyl-uridine (3-1) was reacted with bis(diisopropylamino)chlorophosphine to produce intermediate 3-2, which was without isolation reacted with O-propargyl dithiothreitol (3-5) without addition of an auxiliary catalyst. Alternatively, 3-5 can be reacted with bis(diisopropylamino)chlorophosphine to yield intermediate 3-6, which again, without isolation was reacted with nucleoside 3-1 to produce the phosphoramidite 3-3. This compound was purified by silica gel column chromatography typically applied to purification of standard cyanoethyl group containing phosphoramidites and exhibited similar physicochemical behavior, including stability. The O-substituted dithiothreitol 3-5 was prepared from commercially available racemic dithiothreitol and propargyl bromide under phase transfer conditions, Scheme 3a. Similar phase transfer O-alkylations with suitable alkylating agents such as halides or sulfonates were used to access other substituted threitols (DTT) or erythritols (DTE).

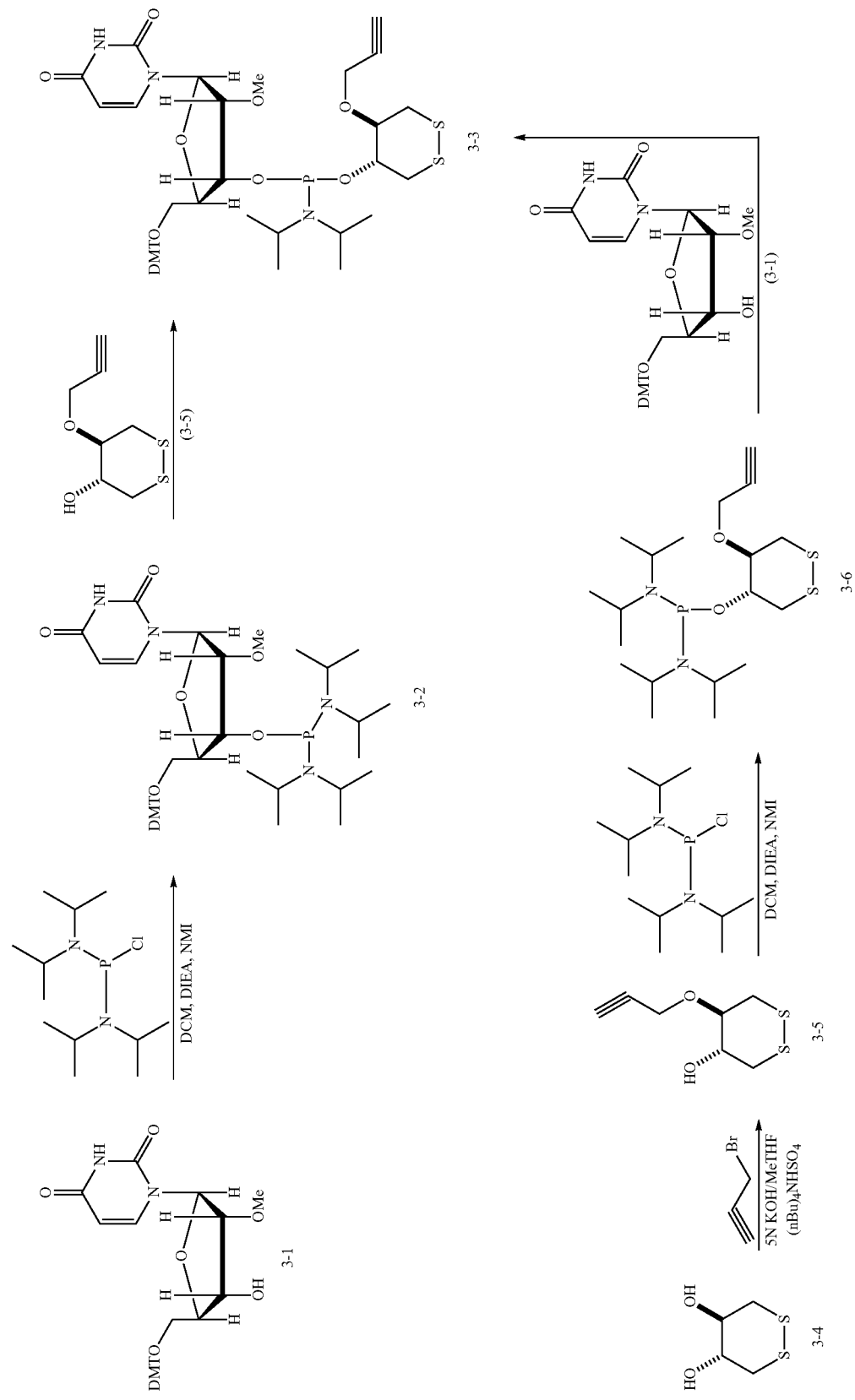

In analogous procedures, replacement of uracil in 3-1 with heterocycles such as guanine, adenine or cytosine led to preparation of phosphoramidites derived from guanosine, adenosine or cytidine. Similarly, other 2'-substituted nucleoside phosphoramidites, carrying for example 2'-deoxy-2'-fluoro or a suitably protected 2'-OH groups can be prepared (see for example Scheme 3b).

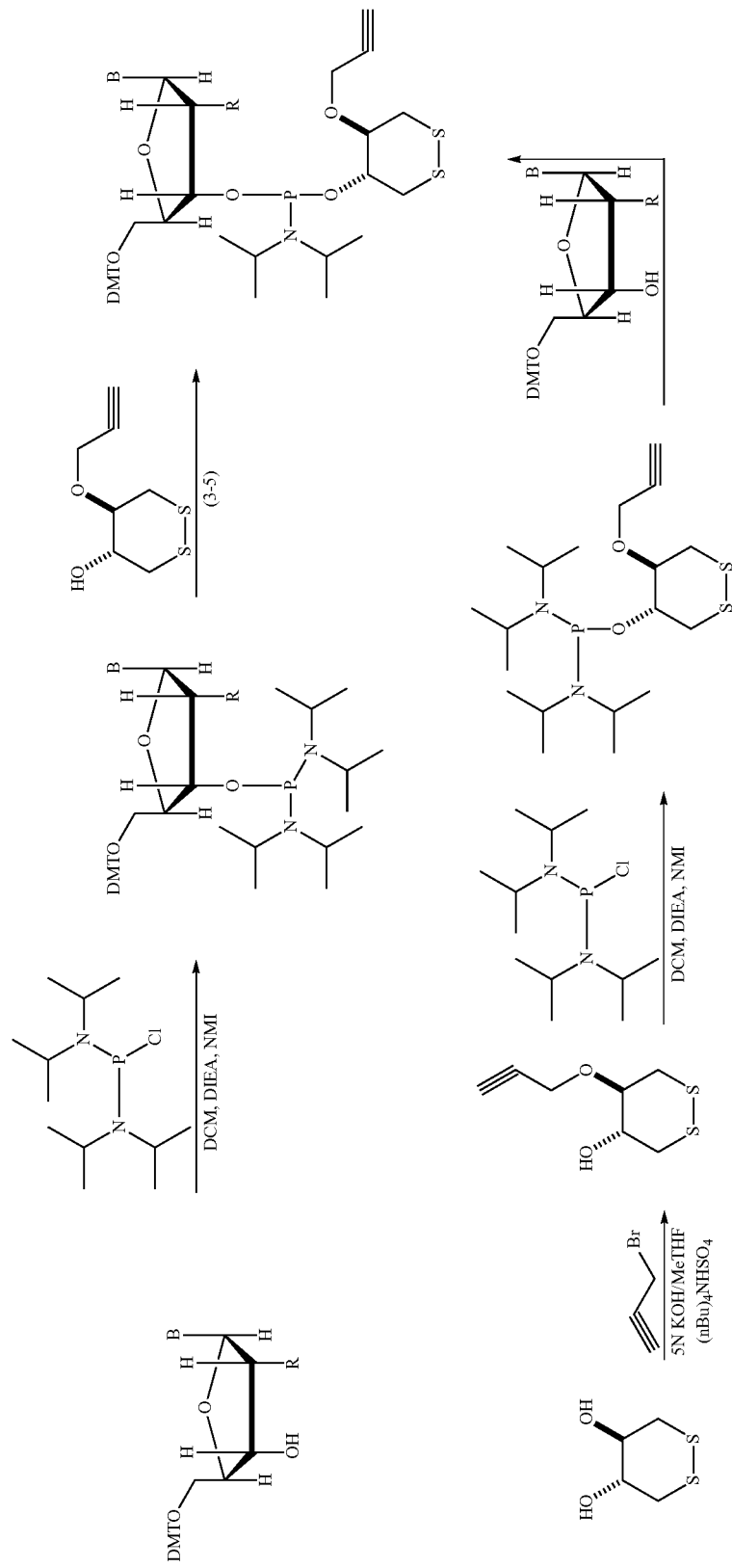

The 5'-unprotected coupling partner in preparation of dimer 5-2 was prepared as described in Scheme 4. 5-Dimethoxytrityl-2'-O-methyl uridine (3-1) was condensed with levulinic acid to yield the ester 4-1, and the acid-labile dimethoxytrityl group was removed using dichloroacetic acid in the presence of dodecanethiol.

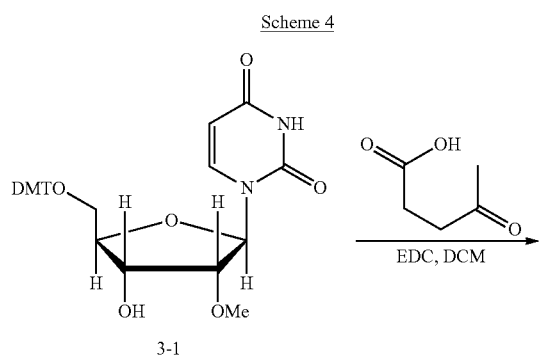

Scheme 4

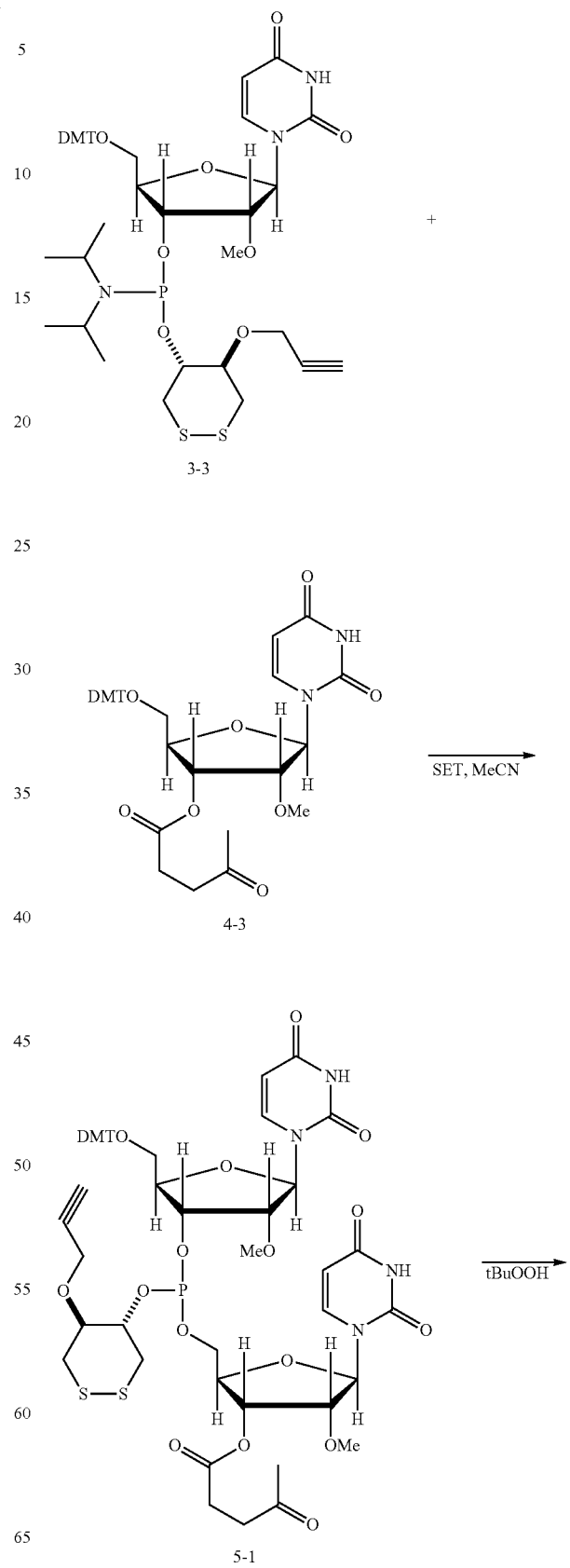

Scheme 5

The desired UpU 5-2 dimer was then prepared by usual coupling of phosphoramidite 3-3 and alcohol 4-2, as shown in Scheme 5. The oxidation of the P(III) intermediate to the P(V) dimer took place using tert-butyl hydroperoxide.

-continued

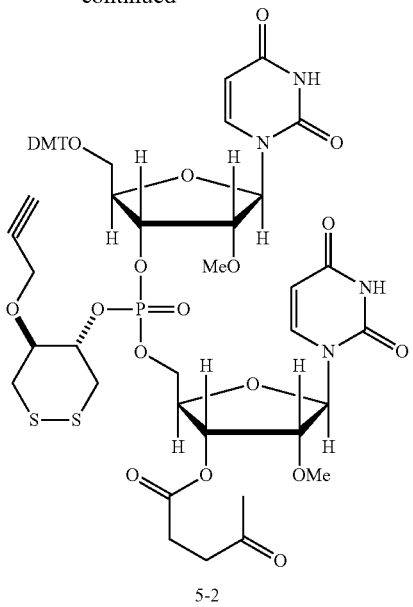

5-2

Since the dithiothreitol employed to make 3-3 consisted of a racemic mixture of trans-isomeres and the P(III) to P(V) oxidation proceeded without stereo control, the dimer 5-2 was obtained as a mixture of four diastereosimeres. To facilitate kinetic studies, these isomeres were separated using preparative HPLC. To gain further mechanistic insights, the single isomeres of 5-2 were extensively analyzed by NMR to provide information regarding preferred conformations within the DTT ring. These studies have confirmed that the relative stereochemistry of the two oxygen atoms (at position 1 and 6 on the DTT ring) is indeed trans, and their absolute orientation is, as expected, di-equatorial.

Figure 2:
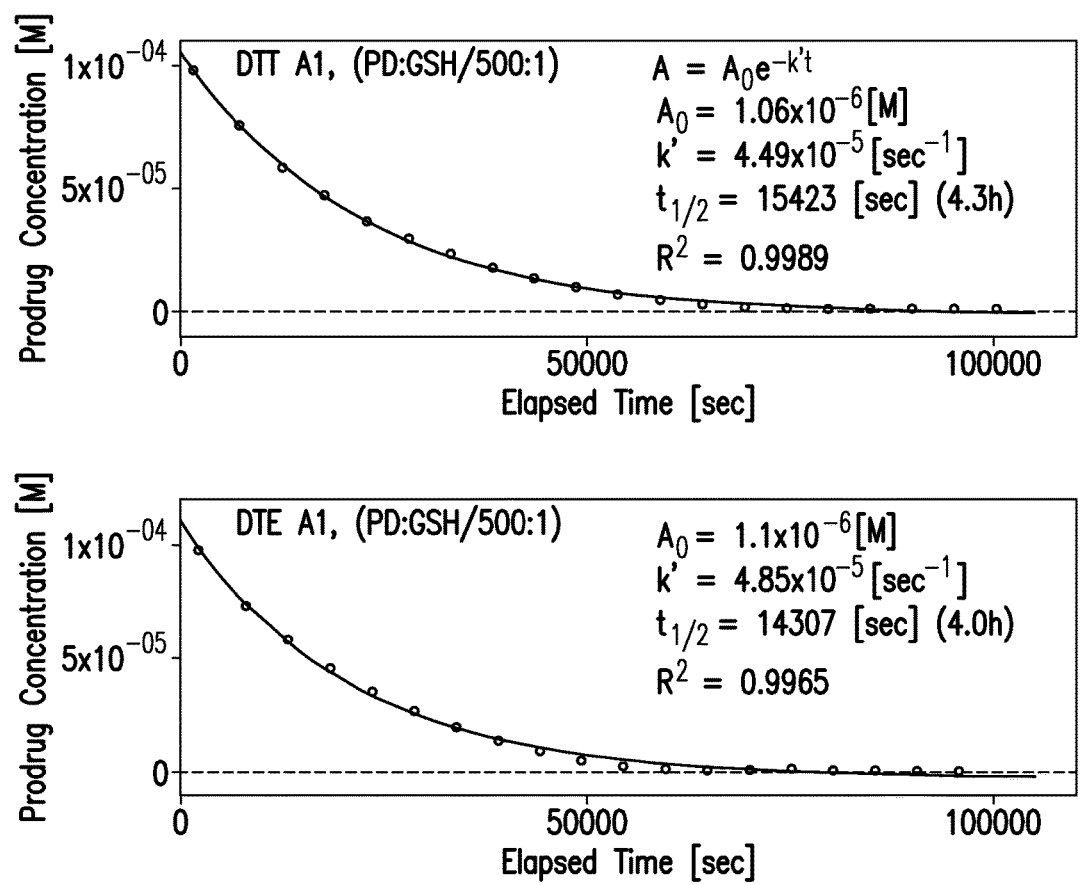
FIG. 2 shows the kinetic behavior of DTT-based dimers upon exposure to glutathione.

Exposure of DTE- or DTT-based dimers (5-2) to glutathione (GSH) resulted in rapid cleavage of the disulfide bond and the envisioned cyclodeesterification effected the release of the dimer phosphodiester, FIG. 2. The kinetic behavior of this model system was found to be consistent with a pseudo-first order reaction kinetics. The half life of prodrug-dimer 5-2 was dependent on the character and excess of the reducing reagent (500:1/Prodrug:GSH), in this instance approximately 4 hours. The kinetics of the release was also dependent on pH and 1M TRIS hydrochloride buffers of pH values varied between 5.0 and 7.8 were used. As expected, the release was considerably slower at acidic conditions (data shown in FIG. 2 were recorded at pH of 7.30). The dithioerythritol (DTE) derivative with cis-stereochemistry (axial/equatorial orientation) showed similar kinetic behavior.

In order to verify that the cleaved dithiothreitol based linker undergoes the envisioned 1,5-exo-tet ring closure to neutralize the transient thiirane, the propargyl group of dimer 5-2 was modified, Scheme 6. It is known that 7-hydroxycoumarin can be easily traced by its strong UV absorbance at 340 nM, and it would make the identification of linker-related products facile. Accordingly, 3-azido-7-hydroxycoumarin was reacted with a single isomer of dimer 5-2 (B1 isomer was used) and the product (6-1) showed strong absorption at both 220 nm (dimethoxytrityl-) as well as 340 nm (coumarin). Exposure to glutathione (or other reducing agent, e.g. TCEP) lead to release of the dimer 6-2 (UV at 220 nm, not at 340 nm) and a product which showed strong UV absorbance at 340 nm, but not at 220 nm. LCMS analysis suggested a molecular weight of 378, which corresponds well for either structure 6-3, or 6-4.

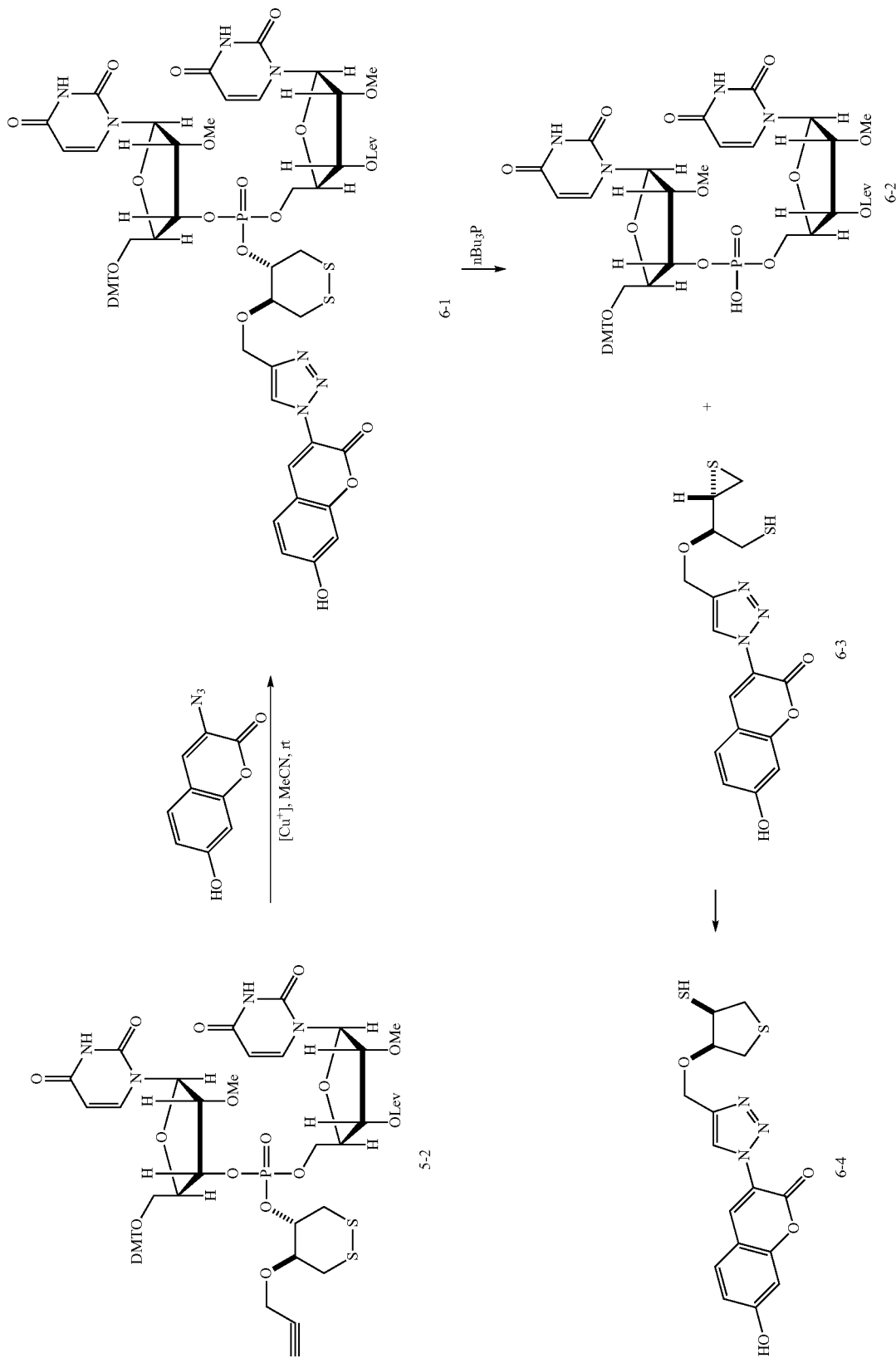

In order to differentiate between thiirane 6-3 and tetrahydrothiophen 6-4, a substantial quantity of this material was needed. The independent synthesis is described in Scheme 7. The commercially available phosphormidite 7-1 was condensed with propargyl dithiothreitol (3-5) under typical reaction conditions (thioethyltetrazole, DCM) and oxidized (tert-butyl hydroperoxide). The UV marker was attached by a click reaction to produce the P(V)-triester 7-3. Exposure of this material to reducing conditions (tributylphosphine) led to rapid ejection of the diester 6-2 and formation of a 340 nm UV active product, which was identical (HPLC/MS, UV) to that obtained from dimer 6-1.

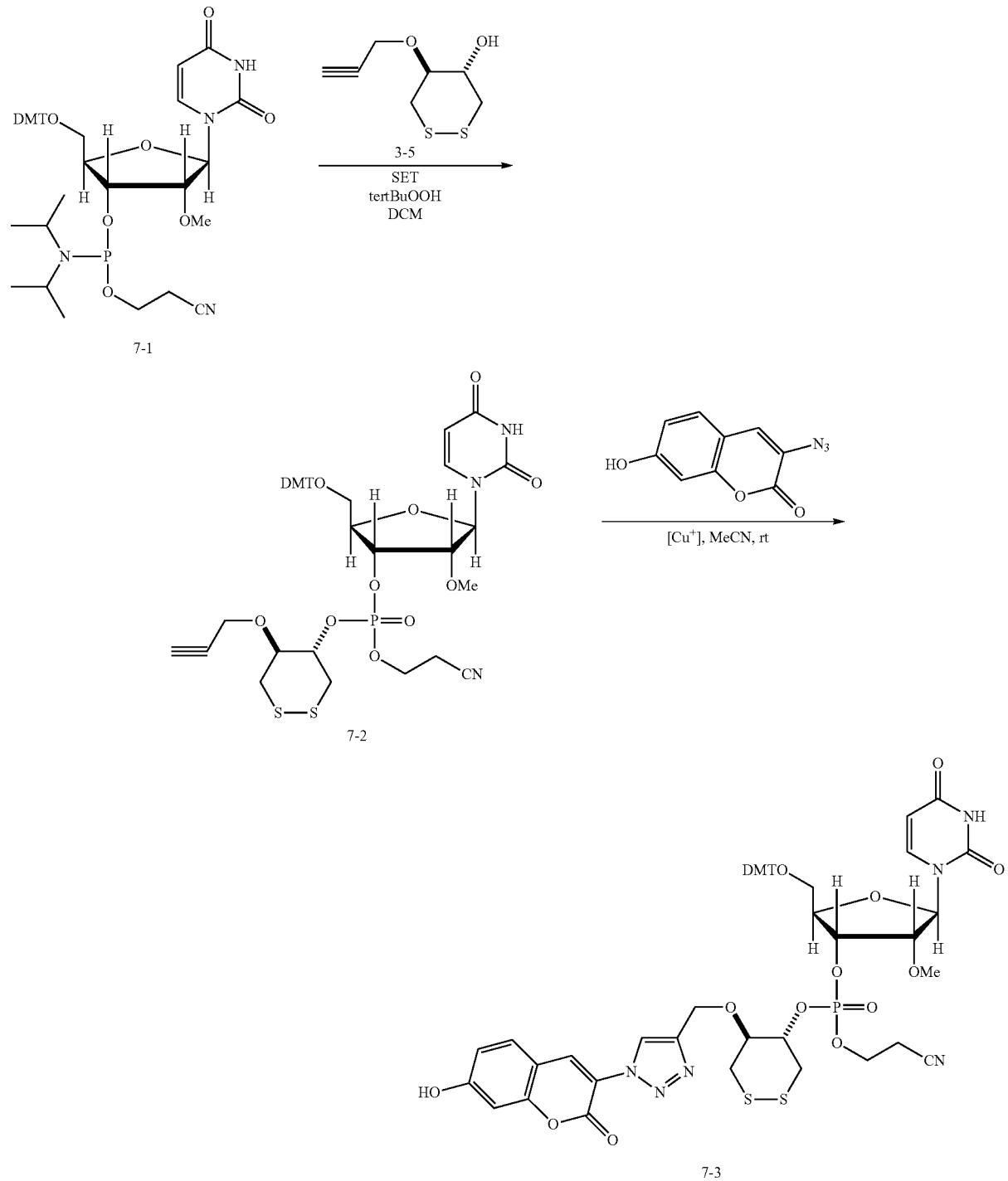

Scheme 7

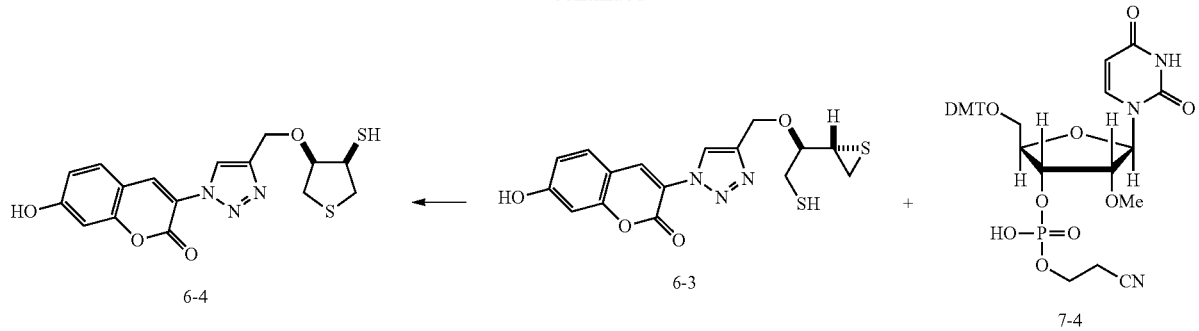

Figure 3:
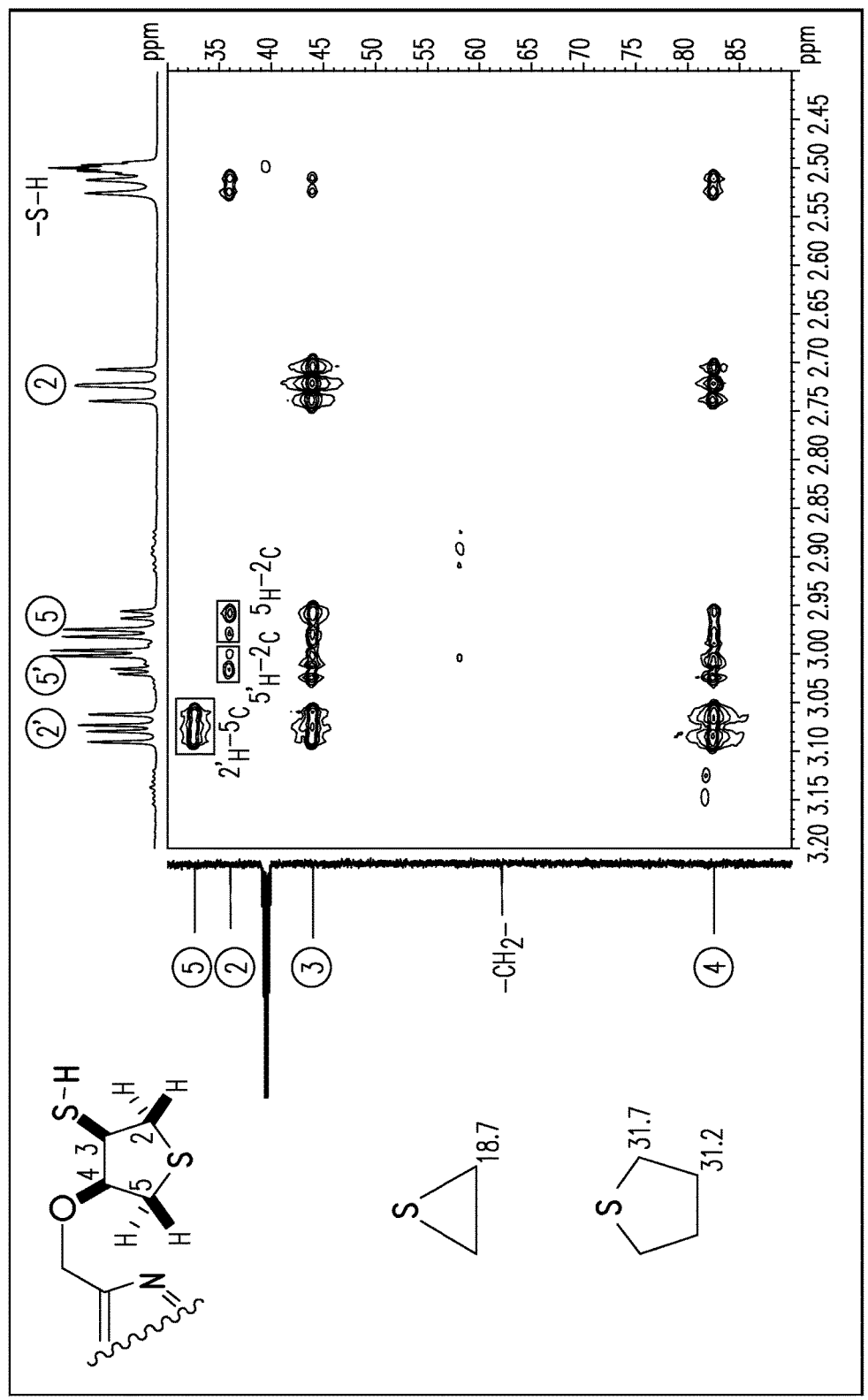
FIG. 3 shows NMR results confirming the formation of a tetrahydrothiophen product.

Extensive NMR analysis of this product confirmed, that its structure corresponds to 6-4 and not 6-3, FIG. 3.

To verify that the release mechanism operates properly when part of an oligomer, the DTT-triester was incorporated into siRNAs targeting β-catenin (CTNNB1 1767). This sequence contained nucleosides with alternating 2'-fluoro and 2'-methyl modification and the triester was incorporated between the first and second nucleoside of the guide strand. The synthesis of the oligomer was performed under standard conditions, as the sterically hindered phosphotriester was quite resistant to methylamine mediated hydrolysis. The P(III) to P(V) oxidation can be performed either by iodine, or tert-butyl hydroperoxide.

Figure 4:
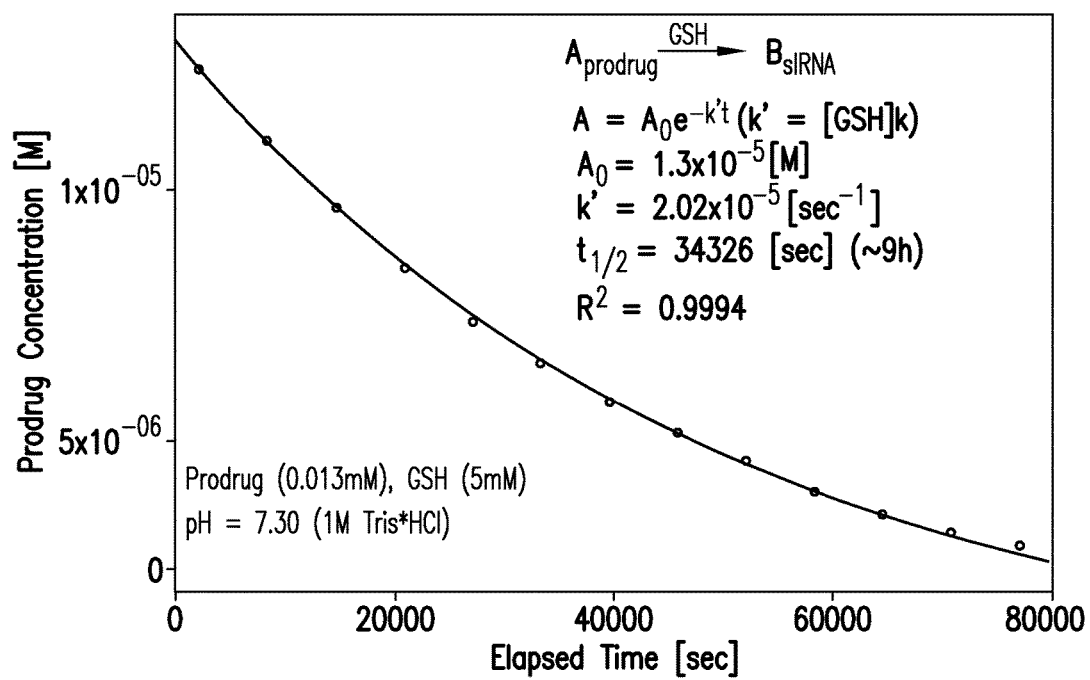
FIG. 4 shows the kinetic behavior of an siRNA oligomer upon exposure to glutathione.

Exposure of this RNA oligomer to glutathione (GSH) at concentrations similar to those found in cytoplasm (~5 mM) lead to release of the RNA oligomer, FIG. 4. The kinetic behavior was found to be dependent on an excess of the reducing agent (GSH) and pH. The observed half life of the siRNA prodrug (GSH:PD/500:1, pH 7.30) was found to be approximately 9 hours.

Figure 5:
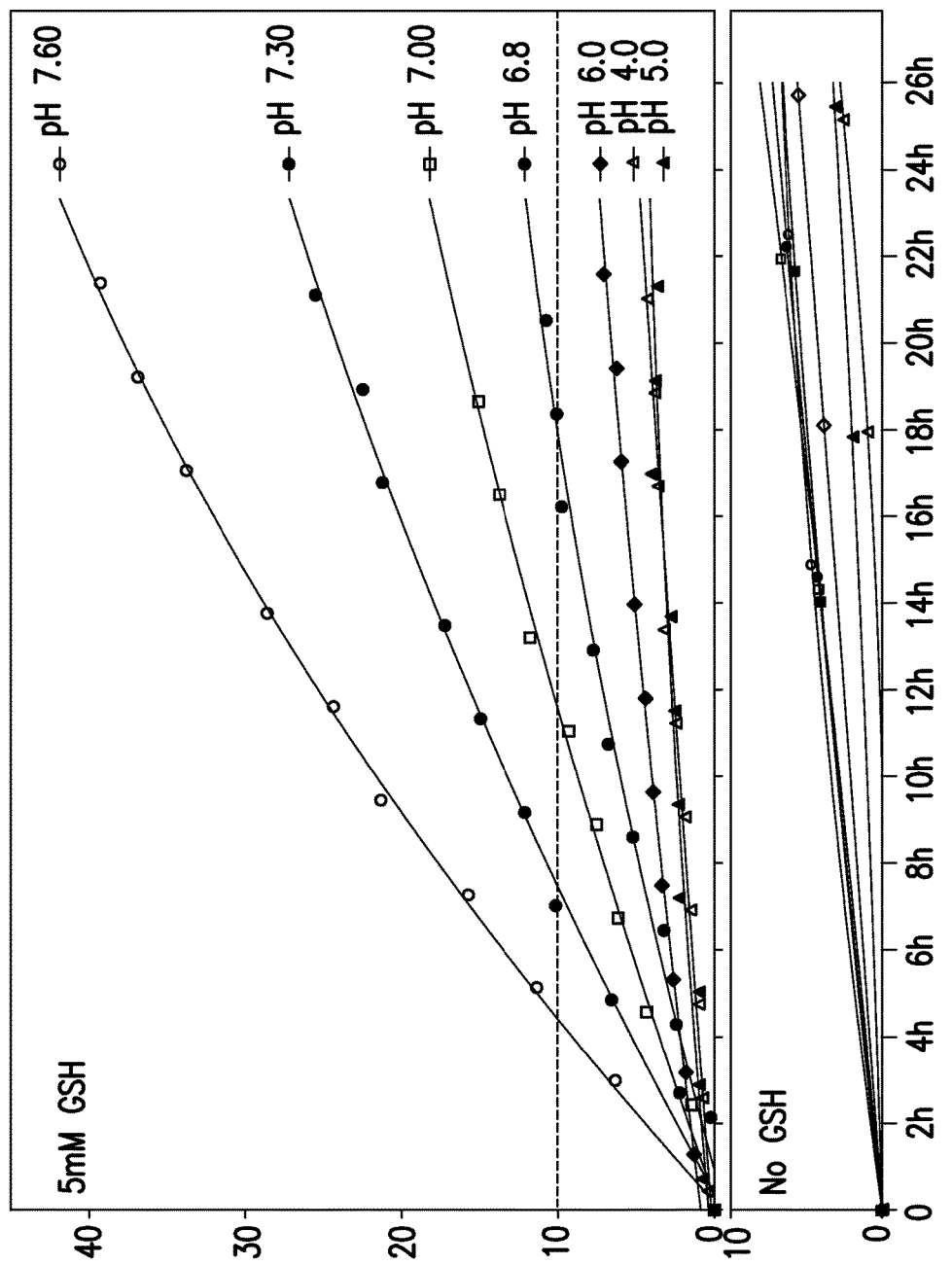
FIG. 5 shows the influence of pH on the siRNA release from RNA prodrug.

The siRNA release is influenced by pH, FIG. 5, main panel. The reduction is slow at acidic pH values (<10% within 24 hours). To demonstrate that the RNA release is glutathione dependent, the RNA prodrug was exposed to the used buffers at their respective pH values, except that no glutathione was added. Under these conditions no more than 10 percent of RNA release was observed within 24 hours which resulted from passive aqueous hydrolysis of the oligomers (FIG. 5, bottom panel).

Figure 6:
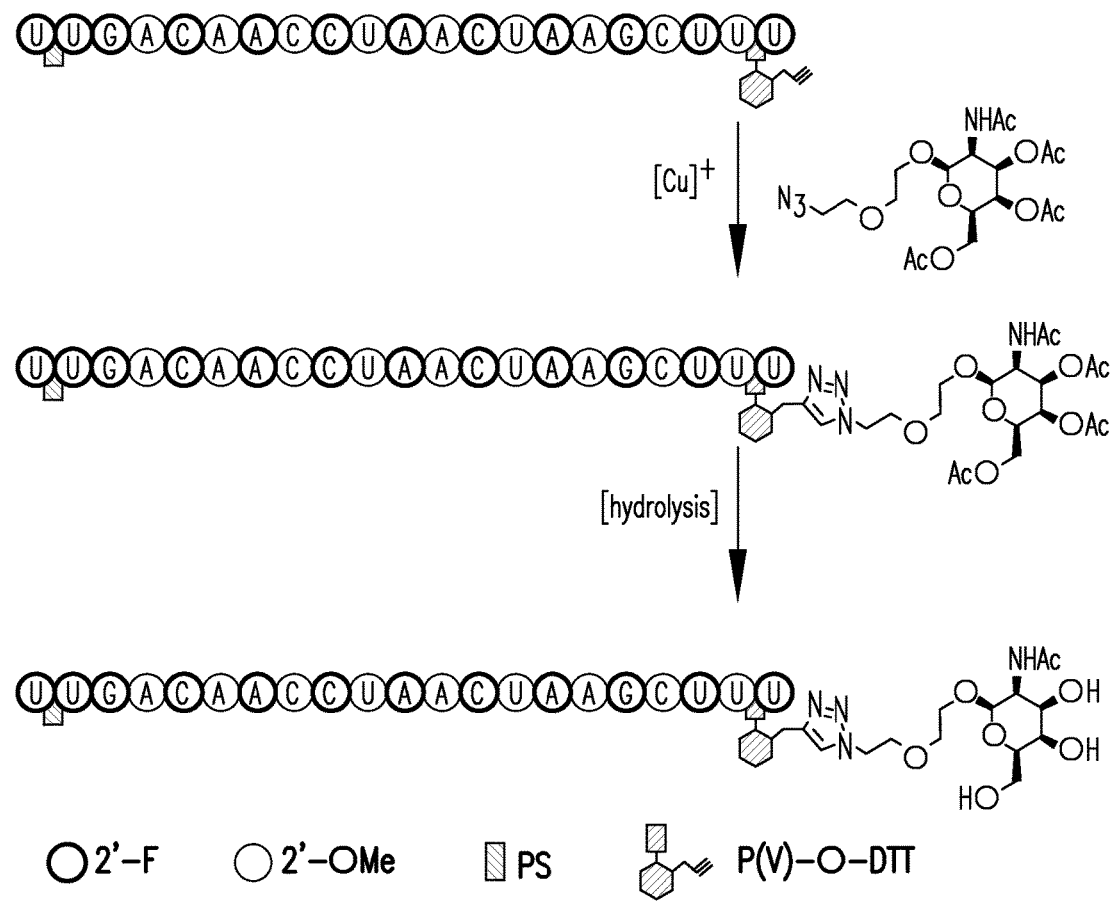
FIG. 6 shows a post synthetic incorporation of a targeting group to an siRNA prodrug.

The propargyl group present in the prodrug is well suited for attachment of targeting, immunossupressing or other groups designed to aid the therapeutic utility of oligomers. For example, N-acetylgalactosamine can bind to the asialo-glycoprotein receptor (ASGPR), a membrane protein present in hepatic cells. Reversible attachment of the N-acetyl-galactosamine group to a therapeutic oligomer can be used to target hepatocytes and the release mechanism described in this invention is uniquely suited to exploit this property. A post synthetic incorporation of this targeting group is shown in FIG. 6. An azide connected to the N,O-peracetylgalactosamine via a short PEG spacer is reacted with the acetylene group present in the linker. The O-acetyl groups are then removed by mild hydrolysis.

This construct provides protection against RNAase mediated RNA cleavage while the oligomer is protected as a prodrug ("extracellular space", "in transit"), and after the ASPGR mediated hepatocyte uptake the targeting group is jettisoned in a glutathione-mediated event and the active oligomer is released at its site of action. Using this mechanism, attachment of multiple targeting ligands or immuno-supressing groups is possible.

Figure 7:
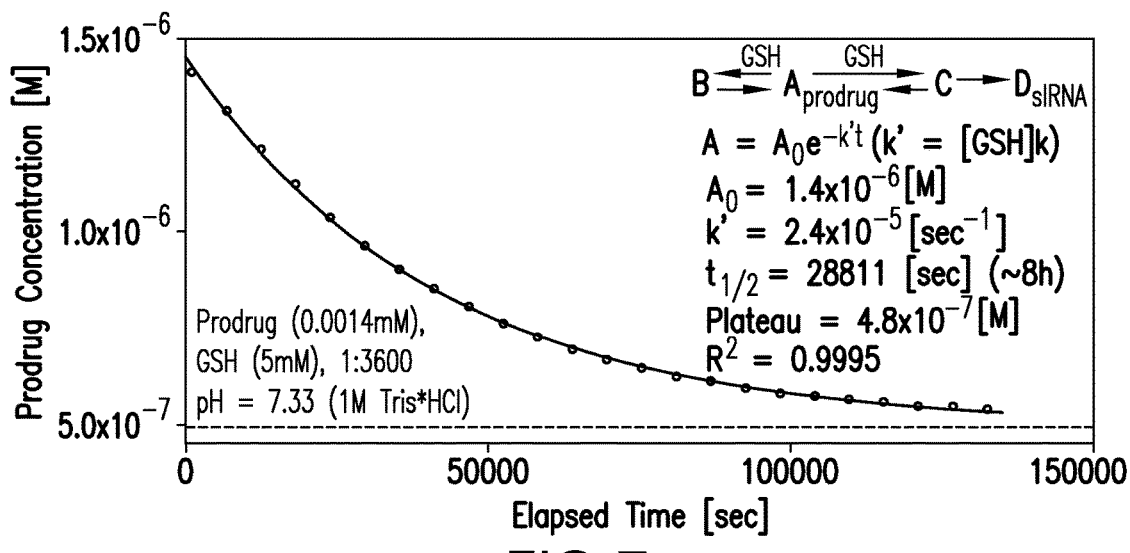
FIG. 7 shows the kinetic behavior of a prodrug construct containing the N-acetyl galactosamine targeting agent upon exposure to glutathione.

To assess the ability of the prodrug construct containing the N-acetyl galactosamine targeting agent (FIG. 6) to eject the active RNA oligomer, the N-acetyl galactosamine prodrug (0.0014 mM concentration) was subjected to gluta-thione (5 mM, prodrug to GSH ratio of 1:3600) at pH of 7.30. The release of the siRNA was monitored using an LCMS and the data are summarized in FIG. 7. In this instance, the half life of the ejection was found to be approximately 8 hours.

Figure 8:
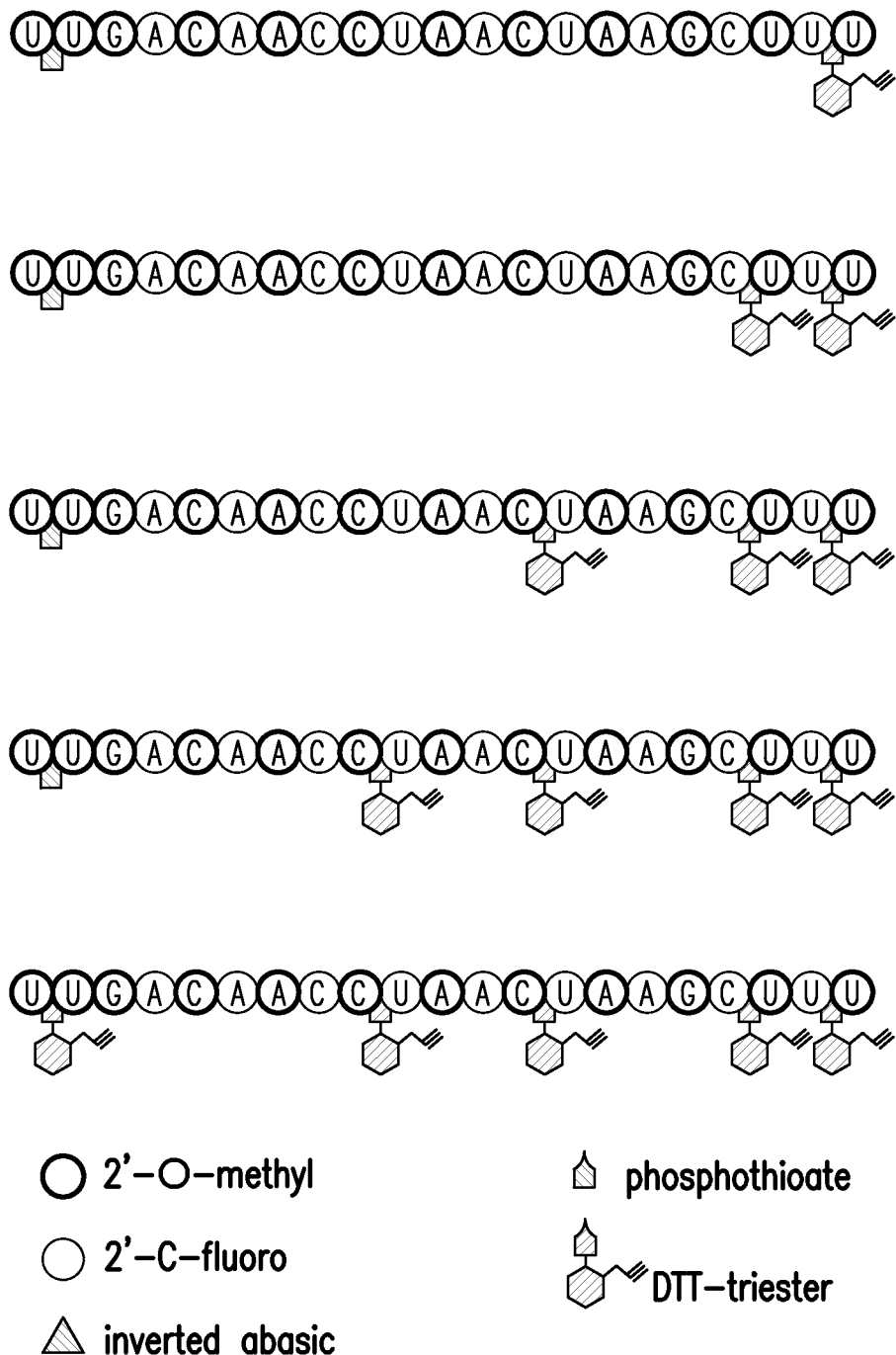
FIG. 8 shows the incorporation of up to five cyclic disulfide prodruging groups onto single strand RNA.

Oligonucleotides containing more than one incorporation of the cyclic disulfide linking group were synthesized using procedures analogous to those used for preparation of oligonucleotides containing only one proudrging group. In this instance, the regular cyanoethyl group containing phosphoramidite was replaced with the phosphoramidite containing the cyclic disulfide at the desired position of the sequence. The efficacy of this synthetic protocol was demonstrated by incorporation of as many as five cyclic disulfide prodruging groups per strand, FIG. 8.

Figure 9:
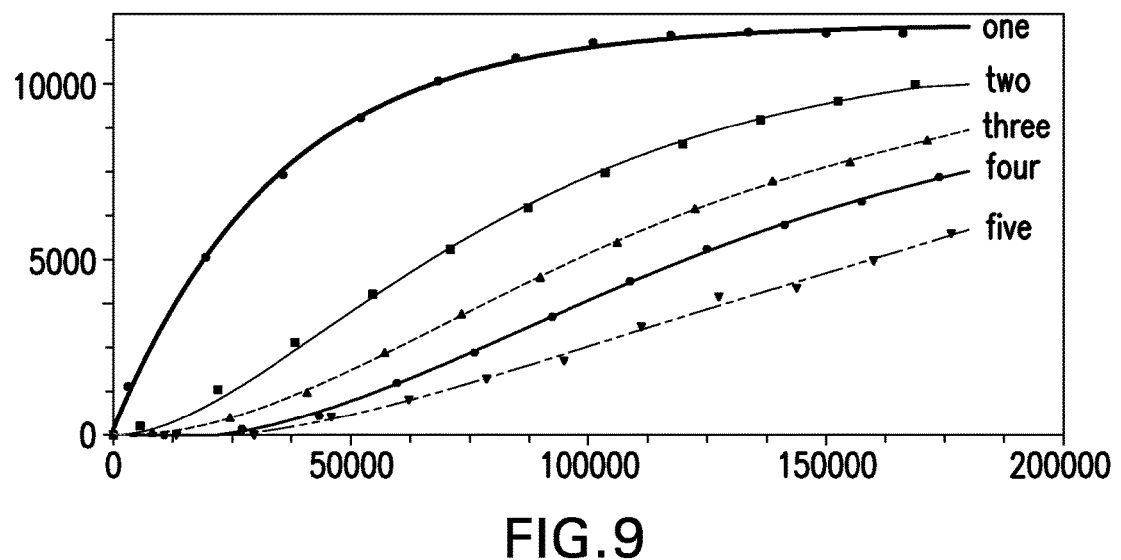
FIG. 9 shows a time course of siRNA releases from prodrug RNAs upon exposure to glutathione.

Exposure of these sequences (15 μM) to 5 mM concentration of glutathione at pH 7.3 (aqueous TRIS.HCl buffer) led to gradual ejection of the parent RNAs. Time course of this release was monitored using an LC/MS and the respective release-curves (x-axis: time in seconds, and the y-axis: area peak) are shown in FIG. 9.

Biology

Figure 10:
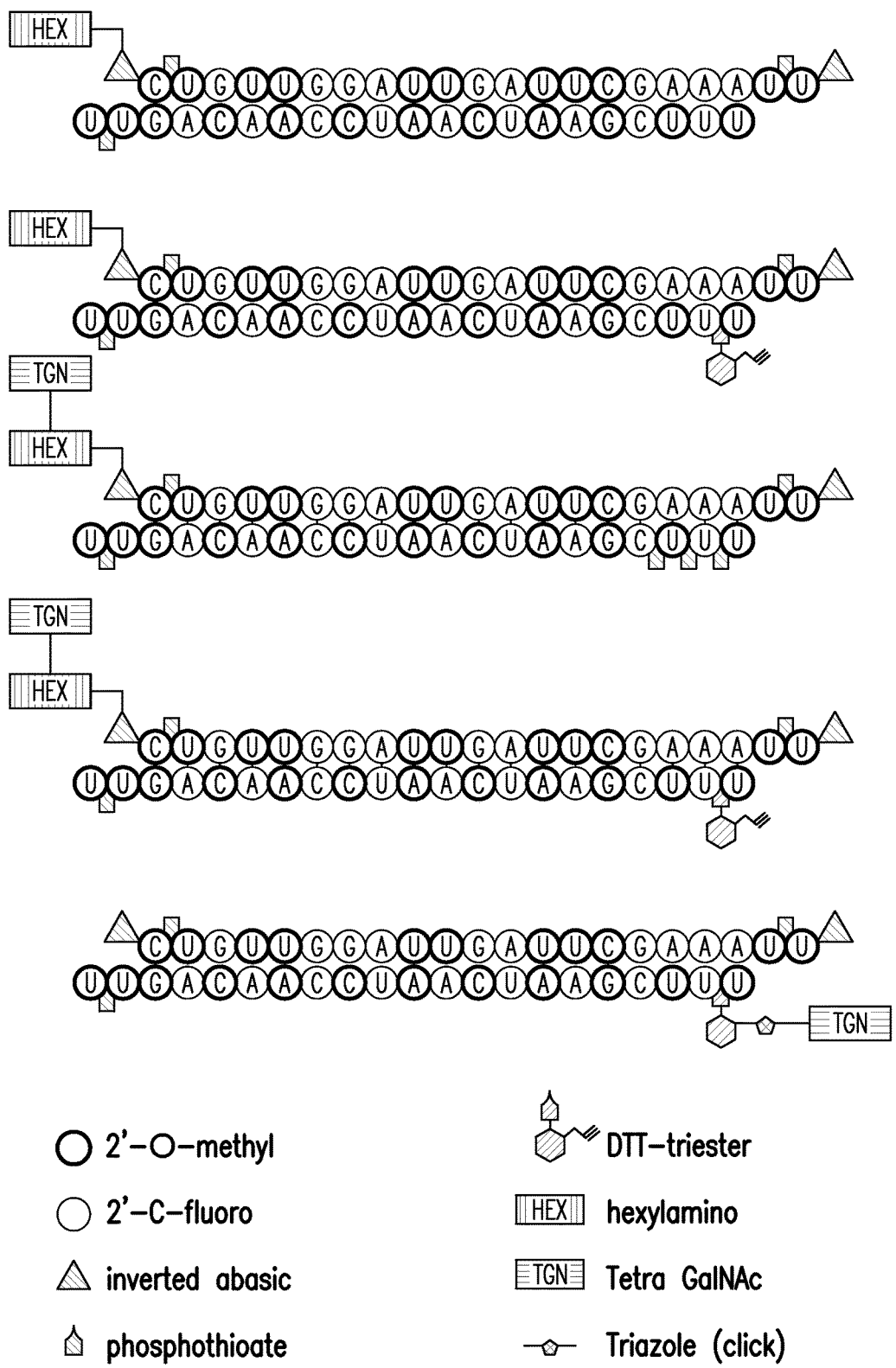
FIG. 10 shows triester prodrugs of siRNA from prodrug RNAs upon exposure to glutathione designed to target the CTNNB1 gene.

To investigate the biological significance of the present invention, we have incorporated the triester-prodrug into siRNA molecules designed to target the CTNNB1 gene, which encodes the β-catenin protein and corresponds to a twenty one nucleotide sequence beginning at nucleotide 1797 (for structures see FIG. 10). The triester-prodrug (DTT) moiety was incorporated between the first and second uridine nucleotides at the 5'-terminus of the guide strand of the siRNA duplex. The nucleosides included within the RNA oligomer were 2'-modified (F, or OMe) to impart stability. The first and last nucleosides of the passenger strand were protected by 5'-phosphodiester containing anhydroribitols (iB). In addition, the iB at the 5'-end of the passenger strand carried a hexylamino group for conjugation to targeting groups, FIG. 10.

Negative charges present along the phosphodiester backbone of oligonucleotides represent an important recognition element of nucleolytic enzymes. Incorporation of phosphotriester-based prodrugs is therefore expected to confer metabolic stability to oligomers. This represents an important use of the instant invention as temporary (extracytoplasmic) protection of oligomers is an important condition for their successful therapeutic use. Data demonstrating this behavior are summarized in Table 1. At 60 and 120 minutes, the prodrug-triester containing duplexes (CTNNB1(1797) 13bDTT, for structures see FIG. 10) showed comparable stability in mouse S9 homogenates (pH 7.5) as well as mouse serum to those with a phosphodiester bond between nucleosides 1 and 2 of the guide strand. However, under conditions mimicking that of rat lysosomes (pH 5.5), the prodrug triester containing siRNAs (R-008522970-000C) proved to be completely stable, while the 1,2-phosphodiesters (R-008428355-000S) were completely hydrolyzed.

TABLE 1

| | | Time Point 60 mins | Standard Deviation | Time Point 120 mins | Standard Deviation |
|---|---|---|---|---|---|
| Rat Lysosome (pH 5.5) | | | | | |
| CTNNB1(1797)13b | PS | 100 | 0 | 100 | 0 |
| (R-008428355-000S) | GS | 1 | 1 | 0 | 0 |
| CTNNB1(1797)13bDTT | PS | 100 | 0 | 100 | 0 |
| (R-008522970-000C) | GS | 99 | 1 | 97 | 4 |
| Mouse S9 (pH 7.5) | | | | | |
| CTNNB1(1797)13b | PS | 99 | 1 | 96 | 2 |
| (R-008428355-000S) | GS | 95 | 4 | 93 | 1 |
| CTNNB1(1797)13bDTT | PS | 100 | 0 | 99 | 5 |
| (R-008522970-000C) | GS | 89 | 4 | 83 | 5 |
| Mouse Serum | | | | | |
| CTNNB1(1797)13b | PS | 100 | 0 | 100 | 0 |
| (R-008428355-000S) | GS | 95 | 1 | 92 | 2 |
| CTNNB1(1797)13bDTT | PS | 100 | 0 | 100 | 0 |
| (R-008522970-000C) | GS | 92 | 0 | 85 | 6 |

Figure 11:
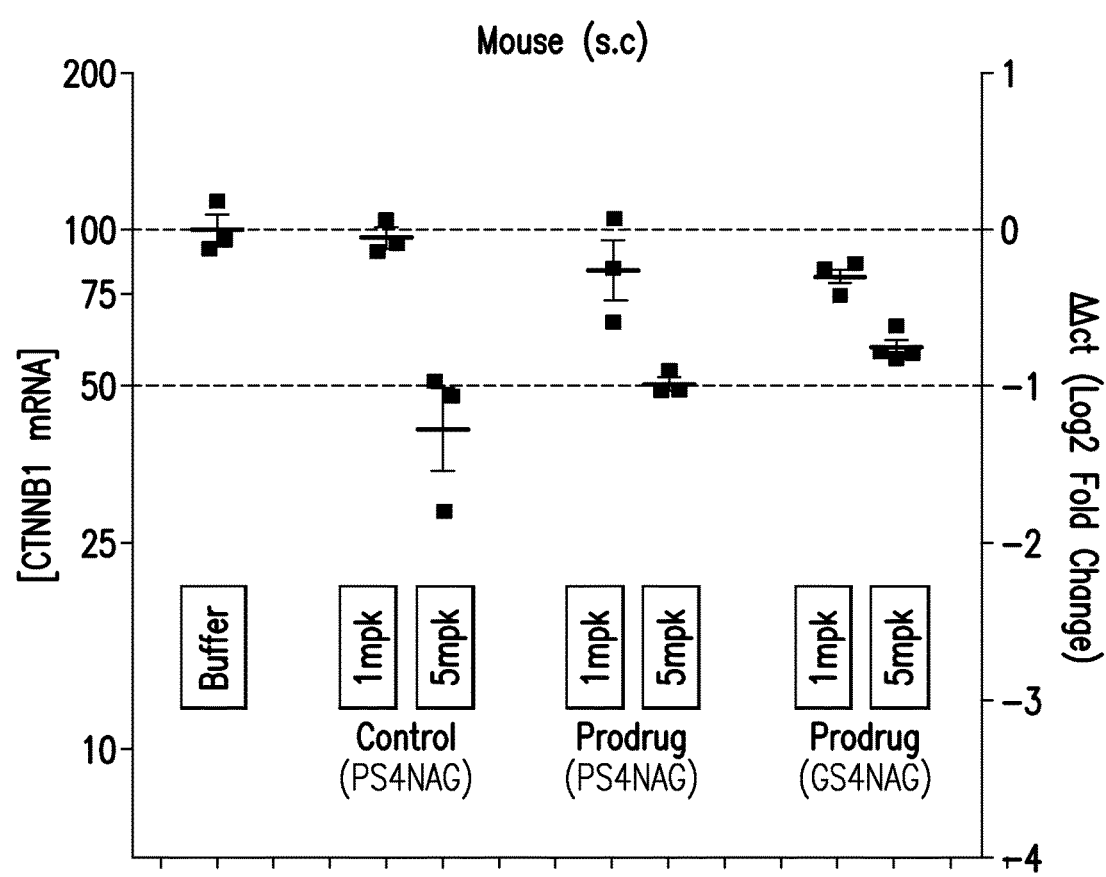
FIG. 11 shows in vivo efficacy of siRNA prodrugs.

The in vivo efficacy of these siRNA prodrugs, structures of which are indicated in FIG. 10, was demonstrated at doses of 1 and 5 mpk in mouse, FIG. 11. The duplexes counting the the DTT-triester prodrug between the first and second nucleoside of the guide strand were shown to be as efficacious as those containing phosphothioate between nucleosides 1,2 and 3,4. Under these conditions, duplexes containing no triester prodrug or thioate modification at these positions were inactive.

Figure 12:
FIG. 12 shows the in vitro and in vivo data for one through five prodrug incorporations.
Figure 13:
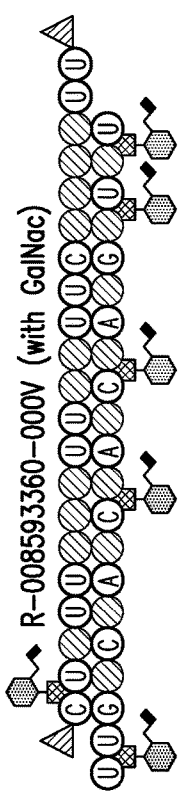
FIG. 13 shows the in vitro and in vivo data for six through ten prodrug incorporations.

The in vitro cell-based potency of duplexes containing multiple prodrug incorporations was evaluated using Hepa 1-6 cells ($IC_{50}$, at 24 h). The respective in vivo activity was assessed by subcutaneous injection of 1 and 5 mpk in mice and the degradation of target RNA (percent KD, "knockdown") was measured after 72 h. Data are summarized in FIGS. 12 (one through five incorporations) and 13 (six through ten incorporations).

Solid-Phase Synthesis of Oligonucleotides

Synthesis of oligonucleotides from natural or chemically modified nucleoside phosphoramidites (phosphoramidites) proceeds in a synthesis cycle where a series of 4 chemical steps is repeated, varying the nature of the phosphoramidite, to obtain the requisite oligonucleotide sequence. The synthesis is carried out on an automated synthesizer from the 3'- to 5'-end on a solid support, typically controlled pore glass (CPG) or polymer bead, where the first 3' protected nucleoside is attached to the support via a suitable linker, often comprising a succinyl linkage.

The first step in the synthesis cycle is removal of a 5'-hydroxyl dimethoxytrityl (DMT) protecting group by treatment with a suitable acid, such as trichloroacetic acid or dichloroacetic acid. Following deprotection, the second step is chain elongation by coupling with a suitably protected phosphoramidite in the presence of an activator, such as 5-ethylthio-1H-tetrazole. The third step in the synthesis cycle is oxidation of phosphorous using an oxidizer, such as tert-butyl hydroperoxide, or iodine in pyridine. Finally, the fourth step is capping any remaining uncoupled 5'-hydroxyl groups with a suitable agent, such as acetic anhydride. This synthesis cycle is repeated; varying the nature of the phosphoramidite, until the desired chain length and composition has been prepared.

The protected oligonucleotide is then liberated from the solid phase support by treatment with a suitable base, such as methylamine in water, which can affect both the cleavage of the oligonucleotide chain from the solid support, as well as remove any exocyclic amine protecting groups. If the oligonucleotide contains any 2'-O-silyl protecting groups, these may be removed by treatment with a suitable reagent, such as triethylamine trihydroflouride.

The crude 5'-DMT protected oligonucleotide is then purified on a suitable support, such as a C-18 resin, where deprotection by-products are removed by elution with aqueous solvents, short-chain capped oligonucleotides may be removed with buffer elution, and the final 5'-DMT protecting group is removed by treatment with an acid, such as trifluoroacetic acid. The purified oligonucleotide is then eluted using a suitable mixture of an organic solvent in water.

This process is repeated to prepare a suitably complimentary oligonucleotide strand.

The two complimentary strands are then mixed together in a 1:1 molar ratio to afford an siRNA duplex.

Intermediates and Compounds

All non-hydrolytic reactions, unless indicated otherwise were carried out in dry solvents purchased from Aldrich. HPLC analyses, except for the amidites, were performed at 60° C. using an Agilent Zorbax Eclipse Plus C18, 2.1×50 mm, 1.8 micron column, at 0.8 mL/min flow rate, eluted with a gradient (5 to 95%) of acetonitrile and water with formic acid (0.1%) as a modifier. The amidites were analyzed using a Supelco Ascentis C18, 100×4.6 mm, 2.7 micron column and ammonium formate (3 mM) as a modifier, under otherwise identical conditions. UV traces were recorded at 220 nm and mass spectra were obtained using an Agilent Technologies 6140 Quadrupole LC/MS mass spectrometer in both positive and negative ion mode. Preparative purifications were performed by gradient chromatography on a Teledyne Isco CombiFlash Rf using pre-packed columns. NMR spectra were recorded on a Varian Unity 600, 500, or 400 spectrometers.

Intermediate 1

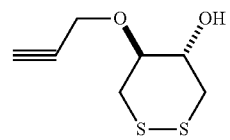

(4S/R,5R/S)-5-(prop-2-yn-1-yloxy)-1,2-dithian-4-ol

A 250 mL three neck flask, equipped with a condenser and overhead stirrer was charged with 5N KOH (100 mL, 500 mmol), followed by 80 mL of 2-methyl tetrahydrofurane, (4S/R, 5R/S)-1,2-dithian-4-ol (10 g, 65.7 mmol) and tetrabutylammonium hydrogen sulphate (4.46 g, 13.14 mmol). To this vigorously stirred mixture was added, via syringe pump, during a period of 12 h, a solution of propargyl bromide (9.38 g, 79 mmol) in 2-methyl tetrahydrofuran (20 mL). The stirring at ambient temperature was continued for additional 12 h. The organic layer was separated, and the aqueous was extracted with ethyl acetate (3×100 mL). The combined organic extracts were washed with water (1×100 mL), brine (1×100 mL) and dried over anhydrous sodium sulfate. Filtration and removal of the solvent in vacuo gave 10.4 g of crude product which was further purified by column chromatography (silica gel, 220 g, methanol-dichloromethane: 0% to 5% of methanol) to yield the pure product as a colorless solid. $^1$H NMR (600 MHz, $CD_3CN$) δ: 4.27 (d, J=2.3 Hz, 2H), 3.42 (ddd, J=11.9, 8.5, 3.7 Hz, 1H), 3.23 (dd, J=13.6, 3.6 Hz, 1H), 3.07 (bd, J=13.0 Hz, 1H), 2.88 (dd, J=13.0, 10.3 Hz, 1H), 2.80 (dd, J=13.5, 10.2 Hz, 1H), 2.73 (t, J=2.5 Hz, 1H). $^{13}$C NMR (600 MHz, $CD_3CN$) δ: 81.5 (br), 80.3, 75.1, 73.4 (br), 57.2, 40.6 (br), 37.6 (br).

Intermediate 2

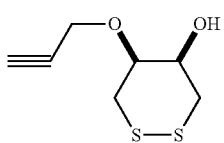

(4S/R,5S/R)-5-(prop-2-yn-1-yloxy)-1,2-dithian-4-ol

This compound was prepared from dithioerythritol disulfide and propargyl bromide using a procedure analogous to that described for Intermediate 1. $^1$H NMR (600 MHz, DMSO-D$_6$) δ: (bs, 1H), 4.25 (s, 2H), 3.7 (bm, 3H), 3.37 (t, J=2.40 Hz, 1H), 3.13 (m, 1H), 2.96 (dd, J=13.2, 8.1 Hz, 1H). $^{13}$C NMR (600 MHz, DMSO-D$_6$) δ: 81.23, 77.64, 75.92 (br), 70.43 (br), 65.48 (br), 56.33 (br.)

Intermediate 3

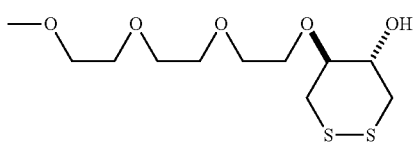

(4S/R,5R/S)-5-{2-[2-(2-methoxyethoxyl)ethoxy]ethoxy}-1,2-dithian-4-ol

This compound was prepared from dithioerythritol disulfide and 2-[2-(2-methoxyethoxy)ethoxy]ethyl 4-methylbenzenesulfonate using a procedure analogous to that described for Intermediate 1. $^1$H NMR (600 MHz, CD$_3$CN) δ: 3.92 (s, 1H), 3.79 (ddd, J=11.3, 6.0, 2.7 Hz, 1H), 3.60 (m, 2H), 3.54 (m, 8H), 3.45 (m, 2H), 3.28 (s, 3H), 3.17 (dd, J=8.5, 4.8 Hz, 1H), 3.05 (dd, J=13.3, 3.6 Hz, 1H), 2.87 (dd, J=13.3, 10.4 Hz, 1H), 2.77 (dd, J=13.3, 10.3 Hz, 1H). $^{13}$C NMR (600 MHz, CD$_3$CN) δ: 83.5, 73.5, 71.8, 70.35, 70.33, 70.30, 70.25, 58.2, 69.3, 40.8, 37.9.

Intermediate 4

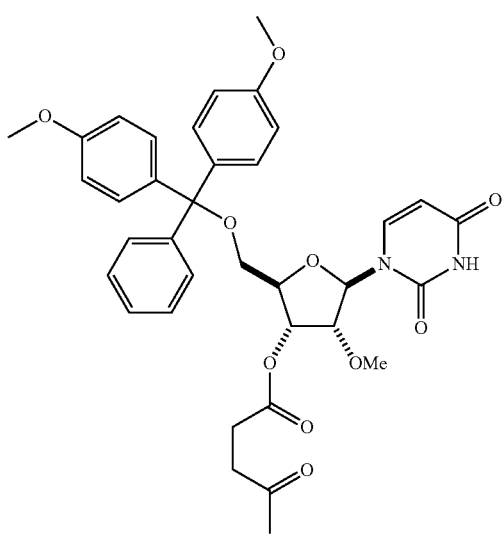 [SMILES: COc1ccc(C(OC[C@H]2O[C@@H](n3ccc(=O)[nH]c3=O)[C@H](OC)[C@@H]2OC(=O)CCC(C)=O)(c2ccccc2)c2ccc(OC)cc2)cc1]

5'-O-[bis(4-methoxyphenyl)(phenyl)methyl]-2'-O-methyl-3'-O-(4-oxopentanoyl)uridine A solution of 5'-dimethoxytrityl-2'-)-methyl uridine (21.25 g, 37.89 mmol) and levulinic acid (6.60 g, 56.9 mmol) in dichloromethane (80 mL) was treated with 1-ethyl-3-[3-dimethylaminopropyl]carbodiimide hydrochloride (21.80 g, 114 mmol) and 4-dimethylaminopyridine (4.63 g, 37.89 mmol) and stirring at ambient temperature was continued for 24 h. The reaction mixture was diluted with dichloromethane (500 mL), washed with water (3×200 mL), brine (1×200 mL) and dried with anhydrous sodium sulfate. The drying agent was filtered off, and the solvent was removed in vacuo. The residue was purified by column chromatography (silica gel, 330 g, methanol-dichloromethane: 0% to 10% of methanol) to yield the pure product. $^1$H NMR (600 MHz, CD$_3$CN) δ: 8.13 (bs, 1H), 7.67 (d, J=8.1 Hz, 1H), 7.42 (d, J=7.7 Hz, 2H), 7.32 (m, 6H), 7.25 (t, J=7.3 Hz, 1H), 6.90 (d, (J=8.0 Hz, 1H), 5.90 (d, J=4.7 Hz, 1H), 5.40 (d, J=8.1 Hz, 1H), 5.29 (t, J=5.4 Hz, 1H), 4.17 (m, 1H), 4.10 (t, J=5.1 Hz, 1H), 3.77 (s, 6), 3.39 (s, 3H), 2.98 (s, 3H), 2.75 (t, J=6.2 Hz, 2H), 2.55 (t, J=6.5 Hz, 2H), 2.12 (s, 3H). $^{13}$C NMR (600 MHz, CD$_3$CN) δ: 207.10, 172.24, 163.46, 159.01, 150.77, 148.37, 144.93, 140.30, 135.71, 135.58, 130.33, 130.30, 128.25, 128.24, 127.29, 117.66, 113.46, 113.44, 102.35, 87.53, 87.04, 81.65, 81.37, 70.53, 62.48, 58.52, 55.20, 38.62, 37.64, 29.15, 27.89, 26.49. LCMS: for C$_{36}$H$_{38}$N$_2$O$_{10}$ calculated 658.3. found 657.2 [M−H]$^-$ (negative).

Intermediate 5

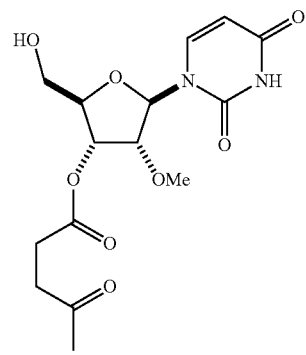

2'-O-methyl-3'-O-(4-oxopentanoyl)uridine

A solution of 5'-O-[bis(4-methoxyphenyl)(phenyl)methyl]-2'-O-methyl-3'-O-(4-oxopentanoyl)uridine (Intermediate 4, 2.11 g, 3.20 mmol) in dichloromethane (30 mL) was treated with 1-dodecanethiol (1 g, 4.94 mmol) and trichloroacetic acid (1.7 g, 0.32 mmol) and stirred at ambient temperature for 1 h. The reaction mixture was neutralized with 30 g of solid sodium bicarbonate and dried with anhydrous sodium sulfate. The solid was filtered off, and the solvent was concentrated to about 10 mL in vacuo. This was loaded onto a silica gel column (80 g, methanol-dichloromethane: 0% to 20% of methanol) to yield the pure product. $^1$H NMR (600 MHz, CD$_3$CN) δ: 9.6 (s, 1H), 8.6 (bs, 1H), 7.9 (d, J=8.1 Hz, 1H), 7.40 (t, J=7.3 Hz, 1H), 5.92 (d, J=5.9 Hz, 1H), 5.69 (d, J=8.2 Hz, 1H), 5.25 (dd, J=5.1, 3.8 Hz, 1H), 4.11 (dd, J=6.0, 2.3 Hz, 1H), 4.06 (t, J=5.6 Hz, 1H), 3.76 (dd, 12.3, 2.5 Hz, 1H), 3.69 (dd, J=12.4, 2.6 Hz, 1H), 3.30 (s, 3H), 2.78 (t, J=6.2 Hz, 2H), 2.58 (t, J=6.5 Hz, 2H), 2.15 (s, 3H). $^{13}$C NMR (600 MHz, CD$_3$CN) δ: 229.78, 207.33, 163.63, 172.38, 163.63, 151.04, 140.83, 117.69, 115.29, 102.57, 87.19, 83.46, 81.63, 71.03, 61.20, 58.38, 37.71, 29.15, 27.94. LCMS: for $C_{15}H_{20}N_2O_8$ calculated 356.1. found 355.0 [M−H]$^-$ (negative).

Compound 1

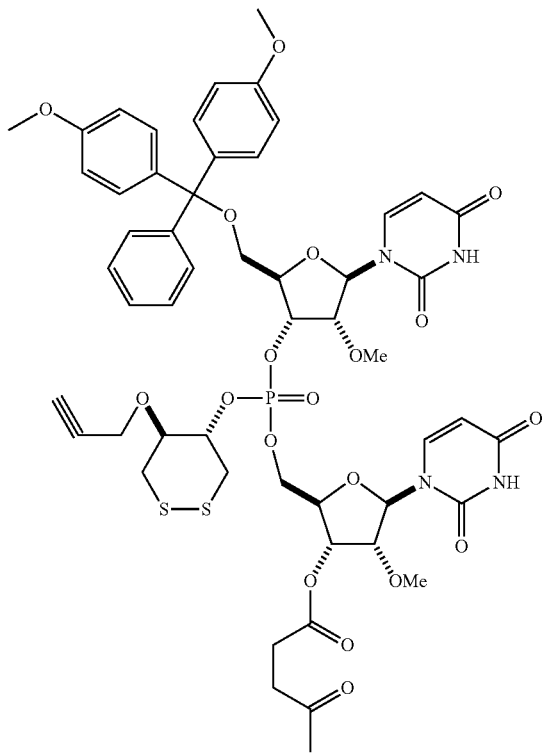

(2R,3R,4R,5R)-2-{[({[(2R,3R,4R,5R)-2-{[bis(4-methoxyphenyl)(phenyl)methoxy]methyl}-5-(2,4-dioxo-3,4-dihydropyrimidin-1(2H)-yl)-4-methoxytetrahydrofuran-3-yl]oxy}{[(4S,5S)-5-(prop-2-yn-1-yloxy)-1,2-dithian-4-yl]oxy}phosphoryl)oxy]methyl}-5-(2,4-dioxo-3,4-dihydropyrimidin-1(2H)-yl)-4-methoxytetrahydrofuran-3-yl 4-oxopentanoate A mixture of 5′-O-[bis(4-methoxyphenyl)(phenyl)methyl]-3′-O-[(dipropan-2-ylamino){[(4S/R,5S/R)-5-(prop-2-yn-1-yloxy)-1,2-dithian-4-yl]oxy}phosphanyl]-2′-O-methyluridine (1.21 g, 1.387 mmol) and 2′-O-methyl-3′-O-(4-oxopentanoyl)uridine (Intermediate 5, 0.535 g, 1.50 mmol) were co-distilled with toluene (3×150 mL) and dissolved in acetonitrile (20 mL). The solution was cooled to 0° C. and treated with 5-ethylthiotetrazole (195 mg, 1.50 mmol). Cooling was removed and the reaction mixture was stirred at ambient temperature for 90 minutes after which time HPLC analysis confirmed disappearance of the starting materials and formation of the P(III)dimer intermediate. Solution of tert-butyl hydroperoxide (5.5M in decane, 50 μL, 2.55 mmol) and stirring was continued for another 3 h, after which time HPLC analysis confirmed completion of the oxidation. The reaction mixture was poured onto 100 mL of 10% sodium thiosulfate and extracted with dichloromethane (3×150 mL). Combined organic extracts were back washed with water (1×150 mL) and brine (1×150 mL), dried (anhydrous sodium sulfate) and the solvent was removed in vacuo to yield the desired product as a mixture of four isomers. The single isomers were obtained by preparative mass-triggered HPLC (Waters XBridge C18, 5 mm, 30×250 mm, 50 ml/min, mobile phase: A=water w/ 3 mM ammonium formate, B=MeCN, gradient 30% to 70% of acetonitrile in 26 minutes).

Isomer A1: $^1$H NMR (600 MHz, CD$_3$CN) δ: $^{13}$C NMR (600 MHz, CD$_3$CN) δ:

Isomer A2: $^1$H NMR (600 MHz, CD$_3$CN) δ: $^{13}$C NMR (600 MHz, CD$_3$CN) δ:

Isomer B1: $^1$H NMR (600 MHz, CD$_3$CN) δ: 9.18 (s, 1H), 9.16 (s, 1H), 7.59 (d, J=8.2 Hz, 1H), 7.51 (d, J=8.1 Hz, 1H), 7.43 (s, 1H), 7.41 (s, 1H), 7.32 (m, 6H), 7.25 (t, J=7.30 Hz, 1H), 6.99 (s, 1H), 6.89 (s, 1H), 5.85 (m, 2H), 5.62 (dd, J=8.1, 2.0 Hz, 1H), 5.34 (dd, J=8.1, 2.1 Hz, 1H), 5.20 (t, J=5.35 Hz, 1H), 4.97 (dd, J=11.6, 5.5 Hz, 1H), 4.30 (m, 5H), 4.22 (bs, 2H), 4.09 (t, J=4.8 Hz, 1H), 3.99 (t, J=5.6 Hz, 1H), 3.76 (s, 6H), 3.59 (m, 1H), 3.47 (s, 3H), 3.42 (dd, J=11.4, 2.5 Hz, 1H), 3.37 (dd, J=11.3, 4.0 Hz, 1H), 3.31 (m, 4H), 3.26 (dd, J=13.5, 3.6 Hz, 1H), 2.94 (dd, J=13.0, 10.4 Hz, 1H), 2.83 (dd, J=13.6, 10.0 Hz, 1H), 2.74 (t, J=6.3 Hz, 2H), 2.56 (t, J=6.6 Hz, 2H), 2.14 (s, 3H), 2.10 (s, 3H). $^{13}$C NMR (600 MHz, CD$_3$CN) δ: 206.90, 172.20, 162.97, 162.93, 159.06, 150.64, 150.57, 144.81, 140.28, 140.21, 135.59, 135.51, 130.35, 130.31, 128.29, 128.36, 127.35, 113.48, 113.46, 102.82, 102.28, 87.73, 87.46, 87.07, 81.78, 81.73, 81.62, 80.89, 80.59, 80.54, 79.79, 75.85, 73.99, 70.37, 67.50, 67.31, 62.35, 58.50, 58.39, 57.23, 55.19, 37.86, 29.11, 27.88. LCMS: for $C_{53}H_{59}N_4O_{19}PS_2$ calculated 1150.3. found 1174.10 [M+Na]$^+$.

Isomer B2: $^1$H NMR (600 MHz, CD$_3$CN) δ: 9.20 (bs, 2H), 7.57 (d, J=8.2 Hz, 1H), 7.50 (d, J=8.1 Hz, 1H), 7.42 (d, J=8.10 Hz, 2H), 7.30 (m, 6H), 7.25 (t, J=7.3 Hz, 1H), 6.88 (dd, J=8.9, 1.4 Hz, 4H), 5.95 (d, J=0.4.9 Hz, 1H), 5.84 (d, J=5.5 Hz, 1H), 5.63 (dd, J=8.1, 2.1 Hz, 1H), 5.32 (dd, J=8.1, 1.9 Hz, 1H), 5.20 (t, J=5.4 Hz, 1H), 4.3 (m, 5H), 4.20 (bs, 2H), 4.07 (t, 4.9 Hz, 1H), 4.02 (t, J=5.6 Hz, 1H), 3.76 (bs, 6H), 3.62 (m, 1H), 3.40 (m, 5H), 3.30 (m, 5H), 3.05 (bt, J=11.5 Hz, 1H), 2.82 (dd, J=13.6, 9.8 Hz, 1H), 2.74 (bt, 6.2 Hz, 2H), 2.56 (bt, J=6.6 Hz, 2H), 2.14 (s, 3H), 2.00 (s, 3H). $^{13}$C NMR (600 MHz, CD$_3$CN) δ: 206.90, 172.22, 162.95, 159.04, 150.62, 144.84, 140.40, 140.16, 135.61, 135.51, 130.38, 130.34, 128.30, 128.25, 127.32, 113.47, 113.45, 102.79, 102.35, 88.00, 87.12, 86.89, 81.94, 81.89, 81.54, 80.80, 80.49, 80.44, 79.83, 75.72, 74.68, 70.34, 67.15, 62.37, 58.49, 58.46, 57.35, 55.19, 37.66, 29.11, 27.88. LCMS: for $C_{53}H_{59}N_4O_{19}PS_2$ calculated 1150.3. found 1174.20 [M+Na]$^+$.

Compound 2

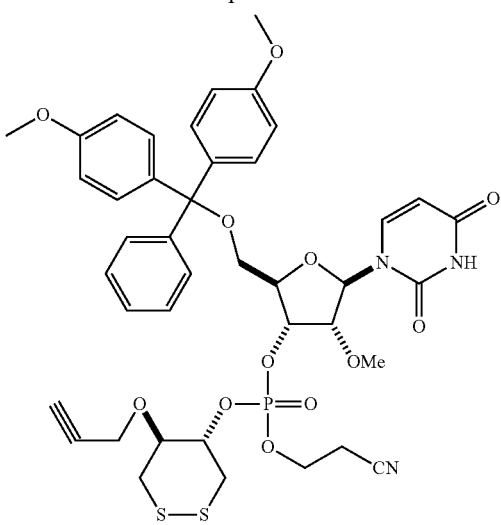

5'-O-[bis(4-methoxyphenyl)(phenyl)methyl]-3'-O-[(2-cyanoethoxy) {[(4S/R,5R/S)-5-(prop-2-yn-1-yloxy)-1,2-dithian-4-yl]oxy}phosphoryl]-2'-O-methyluridine A mixture of 5'-O-[bis(4-methoxyphenyl)(phenyl)methyl]-3'-O-[(2-cyanoethoxy)(dipropan-2-ylamino)phosphanyl]-2'-O-methyluridine (2.74 g, 3.60 mmol) and (4S/R, 5R/S)-5-(prop-2-yn-1-yloxy)-1,2-dithian-4-ol (Intermediate 1, 0.685 g, 3.60 mmol) was co-evaporated with toluene (3×200 mL) and dissolved in acetonitrile (20 mL). Solid thioethyl tetrazole (0.47 g, 3.60 mmol) was added and the solution was stirred at ambient temperature for 1 h. A solution of tert-butyl hydroperoxide (800 μL, 4.40 mmol, 5.5M in decane) was added and stirring continued for additional 3 hours. The reaction mixture was poured onto 100 mL of 10% sodium thiosulfate and extracted with dichloromethane (3×100 mL). Combined organic extracts were back washed with water (1×100 mL) and brine (1×100 mL), dried (anhydrous sodium sulfate) and the solvent was removed in vacuo to yield the desired product as a mixture of four isomeres. LCMS: for $C_{41}H_{44}N_3O_{12}PS_2$ calculated 865.21. found 888.1 [M+Na]$^+$. $^{31}$P NMR (600 MHz, CD$_3$CN) δ: −2.47, −2.66, −2.70, −3.06.

Compound 3

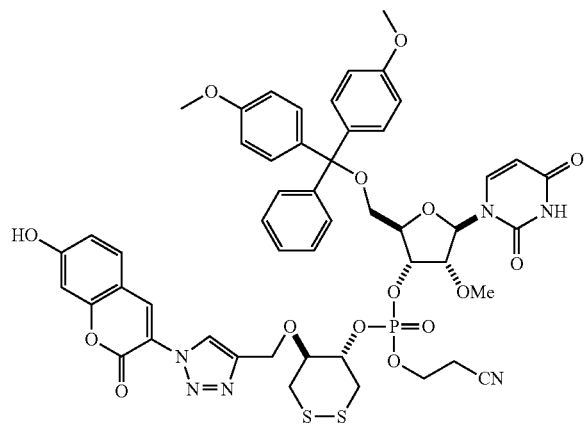

5'-O-[bis(4-methoxyphenyl)(phenyl)methyl]-3'-O-[(2-cyanoethoxy) {[(4S/R,5R/S)-5-{[1-(7-hydroxy-2-oxo-2H-chromen-3-yl)-1H-1,2,3-triazol-4-yl]methoxy}-1,2-dithian-4-yl]oxy}phosphoryl]-2'-O-methyluridine A solution of 5'-O-[bis(4-methoxyphenyl)(phenyl)methyl]-3'-O-[(2-cyanoethoxy){[(4S/R,5R/S)-5-(prop-2-yn-1-yloxy)-1,2-dithian-4-yl]oxy}phosphoryl]-2'-O-methyluridine (Compound 2, 3.00 g, 3.46 mmol) and 3-azido-7-hydroxy-2H-chromen-2-one (0.704 g, 3.46 mmol) in a mixture of acetonitrile (10 mL) and dimethylformamide (10 mL) was degassed with a stream of nitrogen. Solid copper (II) sulfate monohydrate (1.23 g, 6.93 mmol) followed by ascorbic acid (1.373 g, 6.93 mmol) was added and stirring at ambient temperature was continued for 3 hrs. The reaction mixture was filtered through celite, evaporated to dryness (temperature of bath kept under 30° C.). The residue was disproportionated between water (100 mL) and dichloromethane (100 mL). The aqueous phase was washed with additional dichloromethane (3×150 mL). The combined organic extracts were washed with water (1×100 mL), brine (1×100 mL), dried (anhydrous sodium sulfate). The drying agent was filtered off, and the solvent was removed in vacuo to yield the desired product as a mixture of four isomeres. LCMS: for $C_{50}H_{49}N_6O_{15}PS_2$ calculated 1068.24. found 1091.2 [M+Na]$^+$. $^{31}$P NMR (600 MHz, CD$_3$CN) δ: −1.98, −2.36, −2.72, −3.09.

Compound 4

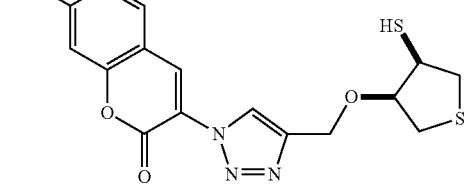

A solution of 5'-O-[bis(4-methoxyphenyl)(phenyl)methyl]-3'-O-[(2-cyanoethoxy){[(4S/R,5R/S)-5-{[1-(7-hydroxy-2-oxo-2H-chromen-3-yl)-1H-1,2,3-triazol-4-yl]methoxy}-1,2-dithian-4-yl]oxy}phosphoryl]-2'-O-methyluridine (Compound 3, 450 mg, 0.421 mmol) in acetonitrile (10 mL) and water (1 mL) was treated with tri-n-butylphosphine (125 μL, 0.505 mmol). HPLC analysis confirmed complete dimer ejection in less than 30 minutes. The reaction mixture was purified by mass-directed preparative HPLC (Waters XBridge C18, 5 mm, 30×250 mm, 50 ml/min, mobile phase: A=water w/ 3 mM ammonium formate, B=MeCN, gradient 30% to 70% of acetonitrile in 26 minutes) to yield the desired product. Analysis of its 1H-, 13C-, HSQC and HMBC spectra confirmed the presence of a tetrahydrothiophene ring. $^1$H NMR (600 MHz, CD$_3$CN) δ: 10.93 (bs, 1H), 8.59 (s, 2H), 7.73 (d, J=8.5 Hz, 1H), 6.90 (d, J=8.6 Hz, 1H), 6.84 (s, 1H), 4.78 (d, J=12.1 Hz, 1H), 4.69 (d, J=12.2 Hz, 1H), 4.19 (dd, J=7.1, 3.6 Hz, 1H), 3.46 (m, 1H), 3.07 (dd, J=10.3, 6.6 Hz, 1H), 3.00 (dd, J=11.3, 3.0 Hz, 1H), 2.96 (dd, J=11.3, 4.4 Hz, 1H), 2.71 (t, J=9.6 Hz, 1H). 2.57 (d, J=8.2 Hz, 1H, exchangeable). $^{13}$C NMR (600 MHz, CD$_3$CN) δ: 162.47, 156.32, 154.64, 143.99, 136.34, 130.94, 125.00, 119.30, 114.28, 110.31, 102.15, 82.59, 62.16, 44.01, 36.09, 32.67. LCMS: for $C_{16}H_{15}N_3O_4S_2$ calculated 377.05. found 378.10 [M+H]$^+$.

Example 1

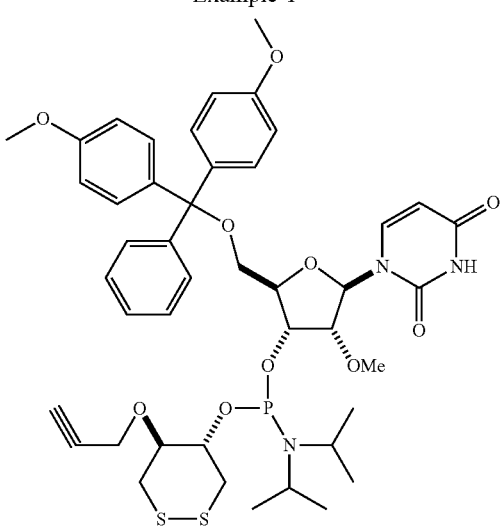

5'-O-[bis(4-methoxyphenyl)(phenyl)methyl]-3'-O-[(dipropan-2-ylamino){[(4S/R,5S/R)-5-(prop-2-yn-1-yloxy)-1,2-dithian-4-yl]oxy}phosphanyl]-2'-O-methyluridine A solution of 5'-O-dimethoxytrityl-2'-O-methyl uridine (1.80 g, 3.21 mmol) and N,N-diisopropylethylamine (1.25 g, 9.63 mmol) in dichloromethane (15 mL) was cooled to 0° C. and bis(diisopropylamino)chlorophophine (1.71 g, 6.42 mmol) and 1-methylimidazole (132 mg, 1.605 mmol) was added. Cooling was removed and the reaction mixture was stirred at ambient temperature for 90 minutes. After this time the formation of the bis-diisopropylamino intermediate was complete and (4S/R, 5R/S)-5-(prop-2-yn-1-yloxy)-1,2-dithian-4-ol (Intermediate 1, 1.22 g, 6.42 mmol) was added. The reaction mixture was stirred an additional 16 h, after which time the solvent was removed in vacuo and the residue was purified by column chromatography (silica gel, 120 g, ethyl acetate-hexane: 45%) to yield the pure product as a colorless viscous liquid. LCMS: for $C_{43}H_{51}N_3O_{10}PS_2$ calculated 879.3. found 880.4. $^{31}$P NMR (600 MHz, $CD_3CN$) δ: 150.70, 149.87.

Example 2

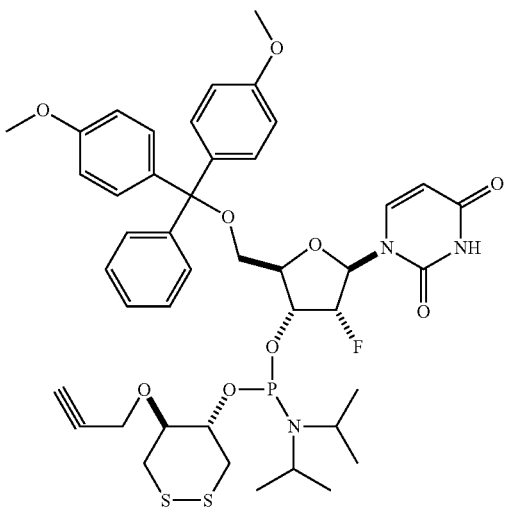

5'-O-[bis(4-methoxyphenyl)(phenyl)methyl]-3'-O-[(dipropan-2-ylamino){[(4S/R,5S/R)-5-(prop-2-yn-1-yloxy)-1,2-dithian-4-yl]oxy}phosphanyl]-2-fluoro-b-D-arabinofuranosyl}pyrimidine-2,4(1H,3H)-dione A solution of (4S/R, 5R/S)-5-(prop-2-yn-1-yloxy)-1,2-dithian-4-ol (Intermediate 1, 5.00 g, 26.3 mmol) was cooled to 0° C. and N,N-diisopropylamine (10.19 g, 79 mmol) followed by Bis(diisopropylamino)chlorophophine (7.71 g, 28.9 mmol) and 1-methylimidazole (1.08 g, 13.14 mmol) was added. Cooling was removed, and the stirring was continued at ambient temperature for 90 minutes. After this time the formation of the bis-diisopropylamino P(III) intermediate was complete and the 5'-O-dimethoxytrityl-2'-deoxy-2'-fluoro uridine was added. Stirring at ambient temperature was continued for additional 16 h, after which time the solvent was removed in vacuo. The oily residue was purified by column chromatography chromatography (silica gel, 220 g, ethyl acetate-hexane: 0 to 30%) to yield the pure product as a colorless viscous liquid. LCMS: for $C_{43}H_{51}FN_3O_9PS_2$ calculated 867.28. found 868.3. $^{31}$P NMR (600 MHz, $CD_3CN$) δ: 151.46, 150.81, 150.61, 150.57.

LCMS: for $C_{24}H_{31}O_4Si$ calculated 411.2. found 411.2 $[M+H-H_2O]^+$ and 427.2 $[M-H]^-$.

Example 3

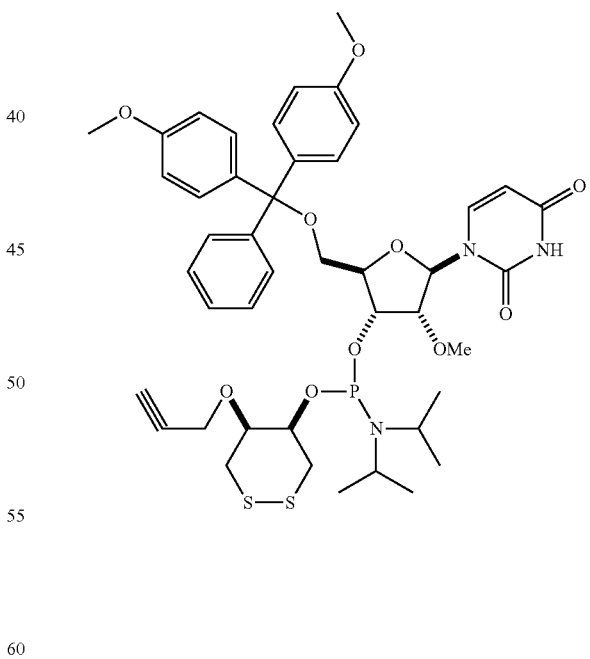

This compound was prepared from 5'-O-dimethoxytrityl-2'-deoxy-2'-O-methyl uridine and (4S/R,5S/R)-5-{2-[2-(2-methoxyethoxy)ethoxy]ethoxy}-1,2-dithian-4-ol. using a procedure analogous to that described for example 2. LCMS: $C_{44}H_{54}N_3O_{10}PS_2$ calculated: 879.30. found 880.3. $^{31}$P NMR (600 MHz, $CD_3CN$) δ: 151.96, 151.20.

Example 4

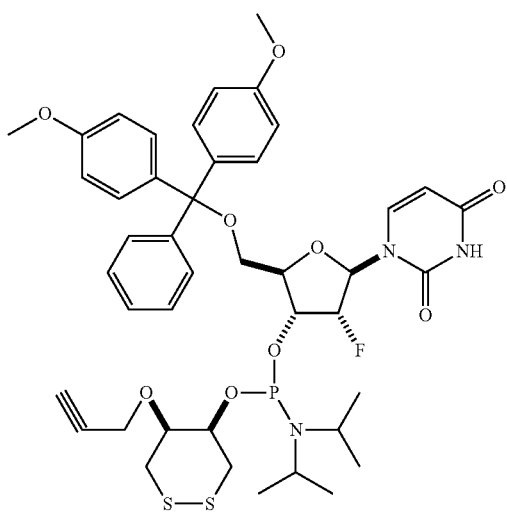

This compound was prepared from 5'-O-dimethoxytrityl-2'-deoxy-2'-fluoro uridine and (4S/R,5S/R)-5-{2-[2-(2-methoxyethoxyl)ethoxy]ethoxy}-1,2-dithian-4-ol. using a procedure analogous to that described for example 2.

Example 5

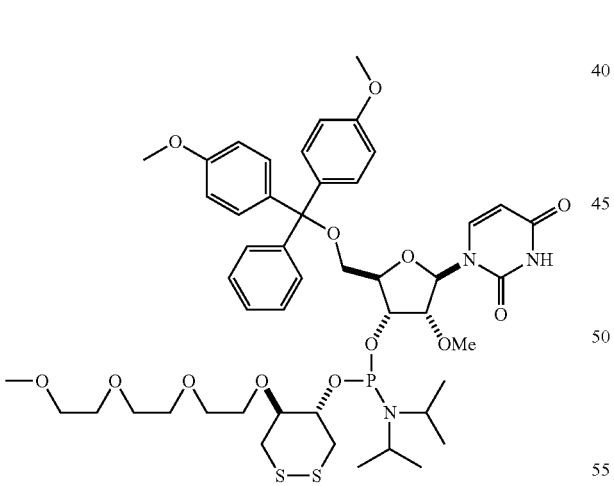

This compound was prepared from 5'-O-dimethoxytrityl-2'-deoxy-2'-O-methyl uridine and (4S/R,5R/S)-5-{2-[2-(2-methoxyethoxyl)ethoxy]ethoxy}-1,2-dithian-4-ol. using a procedure analogous to that described for example 2. $^{31}$P NMR (600 MHz, CD$_3$CN) δ: 150.08, 149.46.

Example 6

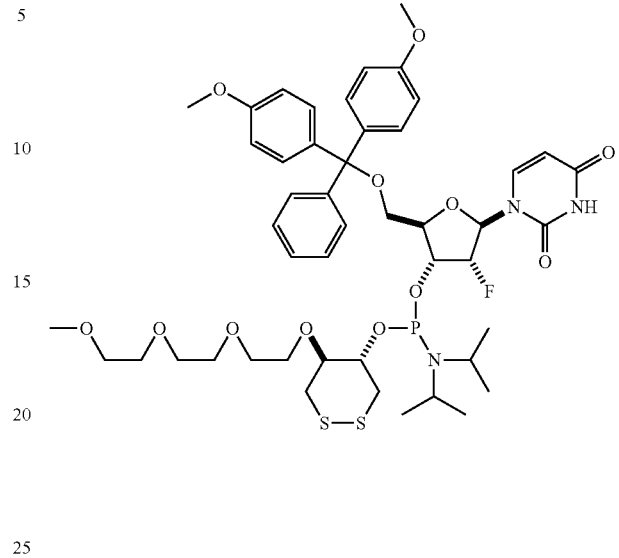

This compound was prepared from 5'-O-dimethoxytrityl-2'-deoxy-2'-fluoro uridine and (4S/R,5R/S)-5-{2-[2-(2-methoxyethoxyl)ethoxy]ethoxy}-1,2-dithian-4-ol. using a procedure analogous to that described for example 2. $^{31}$P NMR (600 MHz, CD$_3$CN) δ: 150.81, 150.68, 149.98, 149.93.

Example 7

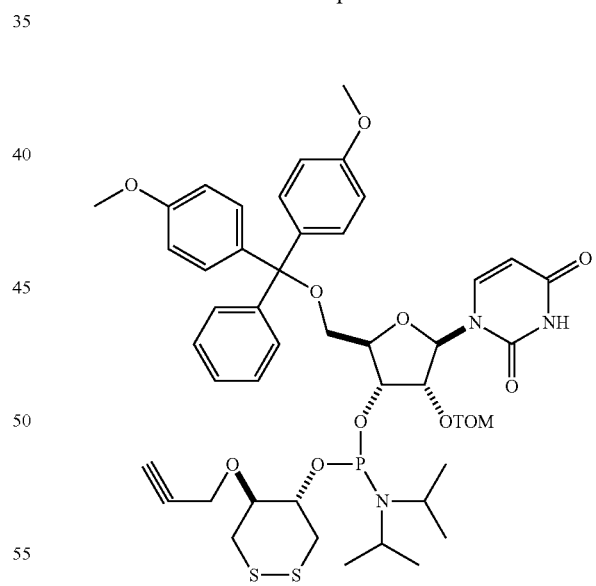

This compound was prepared from commercially available 5'-O-dimethoxytrityl-2'-deoxy-2'-O-triisopropylsilyloxymethyl uridine and (4S/R,5R/S)-5-{2-[2-(2-methoxyethoxyl)ethoxy]ethoxy}-1,2-dithian-4-ol using a procedure analogous to that described for Example 2.

Example 8

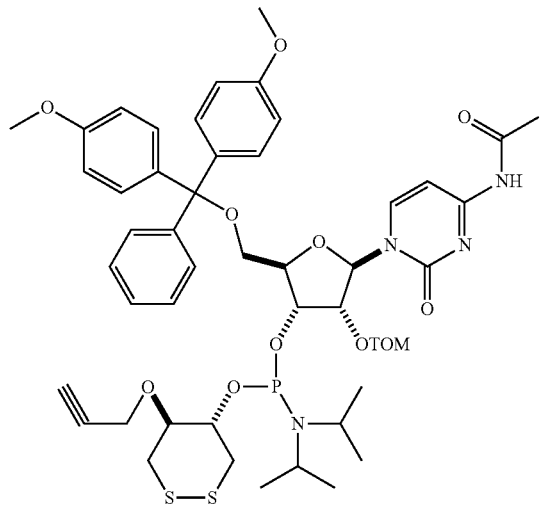

This compound was prepared from commercially available 5'-O-dimethoxytrityl-2'-deoxy-2'-O-triisopropylsilyloxymethyl cytidine and (4S/R,5R/S)-5-{2-[2-(2-methoxyethoxyl)ethoxy]ethoxy}-1,2-dithian-4-ol using a procedure analogous to that described for Example 2.

Example 9

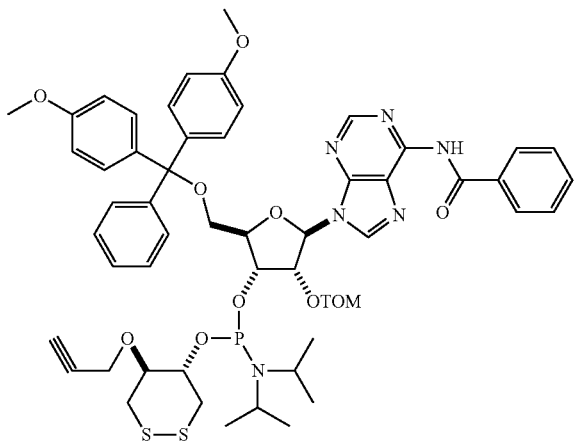

This compound was prepared from commercially available 5'-O-dimethoxytrityl-2'-deoxy-2'-O-triisopropylsilyloxymethyl cytidine and (4S/R,5R/S)-5-{2-[2-(2-methoxyethoxyl)ethoxy]ethoxy}-1,2-dithian-4-ol using a procedure analogous to that described for Example 2.

Example 10

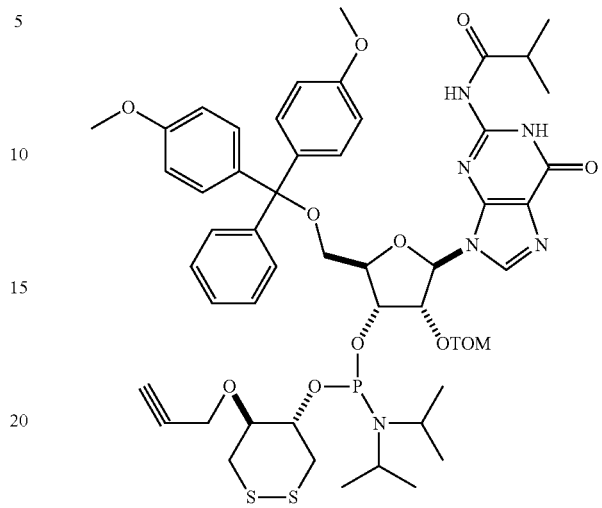

This compound was prepared from commercially available 5'-O-dimethoxytrityl-2'-deoxy-2'-O-triisopropylsilyloxymethyl cytidine and (4S/R,5R/S)-5-{2-[2-(2-methoxyethoxyl)ethoxy]ethoxy}-1,2-dithian-4-ol using a procedure analogous to that described for Example 2.

One skilled in the art would readily appreciate that the present invention is well adapted to carry out the objects and obtain the ends and advantages mentioned, as well as those inherent therein. The methods and compositions described herein, as presently representative of preferred embodiments, are exemplary and are not intended as limitations on the scope of the invention. Changes therein and other uses will occur to those skilled in the art, which are encompassed within the spirit of the invention, are defined by the scope of the claims.

What is claimed is:

1. A compound comprising having the Formula III:

(Formula III)

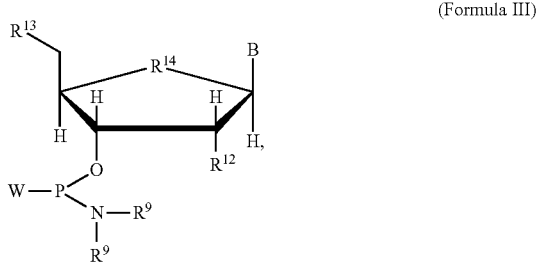

wherein,
W is:

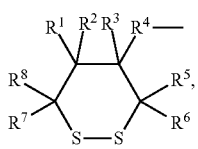

wherein
- $R^1$ is H, OH, $C_{1-6}$ alkyl, $C_{1-6}$ alkyl substituted with one or more hydroxyl groups, or $C_{1-6}$ alkyl substituted with one or more halo groups;
- $R^4$ is S or O covalently attached to P;
- each $R^2$, $R^3$, $R^5$, $R^6$, $R^7$ and $R^8$ are independently halo or hydrogen;
- each $R^9$ is individually $C_{1-6}$ alkyl;
- $R^{12}$ is H, halo, $C_{1-6}$alkoxyl, $C_{1-6}$ alkenyl, $C_{1-6}$ alkenyl substituted with one or more hydroxyl groups, $C_{1-6}$ alkenyl substituted with one or more halo groups, or —$OR^{15}$;
- $R^{13}$ is H, —O-trityl, —O-trityl substituted with one or more hydroxyl or —O—$C_{1-6}$ alkyl groups, —O-pixyl (9-phenylxanthenyl), —O-pixyl (9-phenylxanthenyl) substituted with one or more hydroxyl or —O—$C_{1-6}$ alkyl groups, S-pixyl (9-phenylxanthenyl), S-pixyl (9-phenylxanthenyl) substituted with one or more hydroxyl or —O—$C_{1-6}$ alkyl groups, halo, $C_{1-6}$alkoxyl, $C_{1-6}$ alkenyl, $C_{1-6}$ alkenyl substituted with one or more hydroxyl groups, $C_{1-6}$ alkenyl substituted with one or more halo groups, a phosphate group, a phosphodiester, or —$OR^{15}$;
- $R^{14}$ is O, S, $CH_2$, S=O, CHF, or $CF_2$;
- $R^{15}$ is H, triisopropylsilylO$CH_2$—, tert-butyldimethylsilylO$CH_2$—, triethylsilylO$CH_2$—, trimethylsilylethylO$CH_2$—, triisopropylsilyl-, tert-butyldimethylsilyl-, trimethylsilylethyl-, triethylsilyl-, trimethylsilyl-, or trimethylsilylO$CH_2$—; and
- B is H, 9-adeninyl, 9-guaninyl, 1-uracilyl, 1-cytosinyl, 1-thyminyl, inosinyl, xanthinyl, hypoxanthinyl, isocytosinyl, isoguaninyl, 2-amino-9-adeninyl, 5-methylcytosinyl, 2,6-diaminopurinyl, phenyl, naphthyl, 3-nitropyrrolyl, 5-nitroindolyl, nebularinyl, pyridonyl, or difluorotolyl.

2. The compound of claim 1, wherein $R^1$ and $R^4$ of W are in trans as shown in Formula Wt:

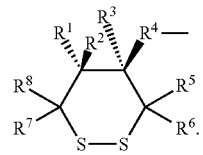

(Formula Wt)

3. The compound of claim 1 having the following formula:

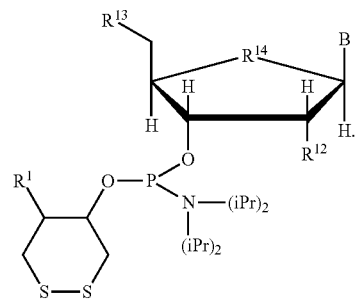

4. The compound of claim 3, wherein $R^1$ is O-propargyl or S-propargyl.

5. The compound of claim 3, wherein $R^{12}$ is H, halo, $C_{1-6}$alkoxyl, or —$OR^{15}$; wherein $R^{15}$ is H, triisopropylsilylO$CH_2$, tert-butyldimethylsilylO$CH_2$O, triethylsilylO-$CH_2$, trimethylsilylethylO-$CH_2$, triisopropylsilyl, tert-butyldimethylsilyl, trimethylsilylethyl or triethylsilyl.

6. The compound of claim 3, wherein $R^{13}$ is H, —O—trityl or substituted —O-trityl.

7. The compound of claim 3, wherein $R^{14}$ is O or S.

8. A composition comprising a compound of claim 1, or a pharmaceutically acceptable salt thereof, and a pharmaceutically acceptable carrier or diluent.

* * * * *